US009333611B2

(12) United States Patent
Dotan et al.

(10) Patent No.: US 9,333,611 B2
(45) Date of Patent: May 10, 2016

(54) FLUID POWERED SPINDLE

(71) Applicant: Colibri Spindles, Ltd., Lavon Industrial Park (IL)

(72) Inventors: Aviad Dotan, Koranit (IL); Tanya Frumson, Maalot (IL); Avigdor Angel, Akko (IL); Baruch Books, Kfar Vradim (IL); Oren Harpaz, Kfar Vradim (IL); Gil Perlberg, Zichron Yaakov (IL)

(73) Assignee: Colibri Spindles, Ltd., Lavon Industrial Park (IL)

( * ) Notice: Subject to any disclaimer, the term of this patent is extended or adjusted under 35 U.S.C. 154(b) by 131 days.

(21) Appl. No.: 14/461,006

(22) Filed: Aug. 15, 2014

(65) Prior Publication Data
US 2015/0075833 A1    Mar. 19, 2015

Related U.S. Application Data

(60) Provisional application No. 61/877,453, filed on Sep. 13, 2013.

(51) Int. Cl.
*E21B 3/00* (2006.01)
*E21B 17/22* (2006.01)
(Continued)

(52) U.S. Cl.
CPC ... *B23Q 5/06* (2013.01); *A61C 1/05* (2013.01); *B23Q 2705/04* (2013.01)

(58) Field of Classification Search
CPC ........... B23Q 11/0046; B23Q 11/0071; B23Q 11/1023; B23Q 2705/04; B23Q 5/06; E21B 4/003; E21B 33/1285; B25B 21/00

USPC ............. 173/1–2, 13–17, 100–115, 124–129, 173/131–138, 141, 170, 184, 189, 193, 173/200–201, 204, 207, 218
See application file for complete search history.

(56) References Cited

U.S. PATENT DOCUMENTS 2,799,934 A     7/1957  Kern
3,058,218 A     10/1962 Kleesattel et al.
(Continued)

FOREIGN PATENT DOCUMENTS

DE    3246111 A1    8/1983
DE    38 19 799     2/1989
(Continued)

OTHER PUBLICATIONS

International Search report issued in PCT counterpart application (No. PCT/IB2014/001795) on Apr. 22, 2015.
(Continued)

*Primary Examiner* — Robert Long
(74) *Attorney, Agent, or Firm* — Womble Carlyle

(57) ABSTRACT

A fluid-powered high-speed spindle (100) having a longitudinal axis (A) defining an upper end defined by a shank and a lower end accepting a tool. The spindle includes a body (120), a rotatable shaft (530) supported by at least one bearing (508) within the body (120), a seal housing (150) connected to the body (120) at the lower end thereof, a cover (180) connected to the seal housing (150) at the lower end thereof, a fluid channel system for directing fluid from an entry port (102) to a nozzle (576) for turning a turbine (570) attached to the shaft (530); and a flinger (660) attached to the shaft (530) and positioned above the turbine (570). The flinger (660) and the seal housing (150) combine to form a non-contact seal (900) configured to impede the flow of fluid toward the at least one bearing (508).

21 Claims, 28 Drawing Sheets

(51) Int. Cl.
    *E21B 19/16*     (2006.01)
    *E21B 19/18*     (2006.01)
    *B23Q 5/06*     (2006.01)
    *A61C 1/05*     (2006.01)

(56) References Cited

U.S. PATENT DOCUMENTS

| | | | |
|---|---|---|---|
| 3,383,805 A | 5/1968 | Powell | |
| 3,707,336 A | 12/1972 | Theis, Jr. et al. | |
| 3,733,143 A | 5/1973 | Theis, Jr. | |
| 3,930,744 A | 1/1976 | Theis, Jr. | |
| 3,976,389 A | 8/1976 | Theis, Jr. | |
| 4,060,336 A | 11/1977 | Theis, Jr. et al. | |
| 4,229,139 A | 10/1980 | Marantette et al. | |
| 4,566,849 A | 1/1986 | Flink | |
| 4,776,752 A | 10/1988 | Davis | |
| 4,941,828 A | 7/1990 | Kimura | |
| 5,020,968 A | 6/1991 | Yamada et al. | |
| 5,228,700 A | 7/1993 | Biesold et al. | |
| 5,293,747 A * | 3/1994 | Geiger | B25F 5/001 60/493 |
| 5,328,271 A | 7/1994 | Titcomb | |
| 5,348,430 A * | 9/1994 | Metz | C21B 7/12 266/271 |
| 5,364,227 A | 11/1994 | Franetzki et al. | |
| 5,419,661 A | 5/1995 | Meachum | |
| 5,439,346 A | 8/1995 | Bowser et al. | |
| 5,507,642 A | 4/1996 | Wohlgemuth | |
| 5,566,770 A | 10/1996 | Bowser | |
| 5,659,205 A * | 8/1997 | Weisser | F03B 13/10 290/43 |
| 5,674,032 A | 10/1997 | Slocum et al. | |
| 5,807,108 A | 9/1998 | Schwenoha et al. | |
| D409,466 S | 5/1999 | Bowser | |
| 6,254,321 B1 | 7/2001 | Lind | |
| 6,318,937 B1 | 11/2001 | Lind | |
| 6,328,509 B1 | 12/2001 | Lind | |
| 6,368,052 B2 | 4/2002 | Uesugi et al. | |
| 6,413,025 B1 | 7/2002 | Lind | |
| 6,413,026 B1 | 7/2002 | Lind | |
| 6,413,027 B1 | 7/2002 | Lind | |
| 6,413,028 B1 | 7/2002 | Lind | |
| 6,497,538 B1 | 12/2002 | Lind | |
| 6,568,886 B1 | 5/2003 | Lind | |
| 6,579,093 B2 | 6/2003 | Bailey et al. | |
| 6,840,723 B2 | 1/2005 | Jacobsson | |
| 7,077,732 B2 | 7/2006 | Dodds | |
| 7,223,069 B2 | 5/2007 | Dodds | |
| D612,406 S | 3/2010 | Jackson et al. | |
| 7,967,552 B2 | 6/2011 | Brett et al. | |
| 8,128,323 B2 | 3/2012 | Conroy et al. | |
| 8,297,949 B1 * | 10/2012 | Mancl | F04D 17/164 417/423.11 |
| 8,382,426 B2 | 2/2013 | Itoh et al. | |
| 2004/0112678 A1 | 6/2004 | Lind | |
| 2005/0019123 A1 * | 1/2005 | Lawson | B23B 31/08 409/140 |
| 2005/0167131 A1 * | 8/2005 | Hurskainen | B25D 9/145 173/206 |
| 2006/0153721 A1 | 7/2006 | Dodds | |
| 2009/0060673 A1 | 3/2009 | Mace | |
| 2009/0123247 A1 | 5/2009 | Clark | |
| 2009/0199591 A1 | 8/2009 | Lee et al. | |
| 2009/0223691 A1 * | 9/2009 | Ikuta | B25D 17/24 173/117 |
| 2009/0301744 A1 * | 12/2009 | Swinford | E21B 4/14 173/200 |
| 2012/0018657 A1 * | 1/2012 | Keskiniva | B25D 9/22 251/314 |
| 2012/0111590 A1 | 5/2012 | Rothenwaender et al. | |
| 2012/0138328 A1 * | 6/2012 | Teipel | B25D 9/12 173/207 |
| 2013/0195576 A1 * | 8/2013 | Jaffe | B23Q 11/1023 409/231 |
| 2014/0054092 A1 * | 2/2014 | Buckman, Sr. | E21B 7/18 175/107 |
| 2014/0083540 A1 * | 3/2014 | Colussi | B60C 23/001 137/625.11 |

FOREIGN PATENT DOCUMENTS

| | | |
|---|---|---|
| DE | 199 17 693 | 10/2000 |
| DE | 20218632 U1 | 2/2003 |
| DE | 10 2009 012 805 | 10/2009 |
| FR | 2 688 731 | 9/1993 |
| WO | WO 99/58984 A1 | 11/1999 |
| WO | 03/019753 | 3/2003 |
| WO | 2008/139472 | 11/2008 |
| WO | WO 2011/001421 A1 | 1/2011 |

OTHER PUBLICATIONS

Written Opinion issued in PCT counterpart application (No. PCT/IB2014/001795) on Apr. 22, 2015.

* cited by examiner

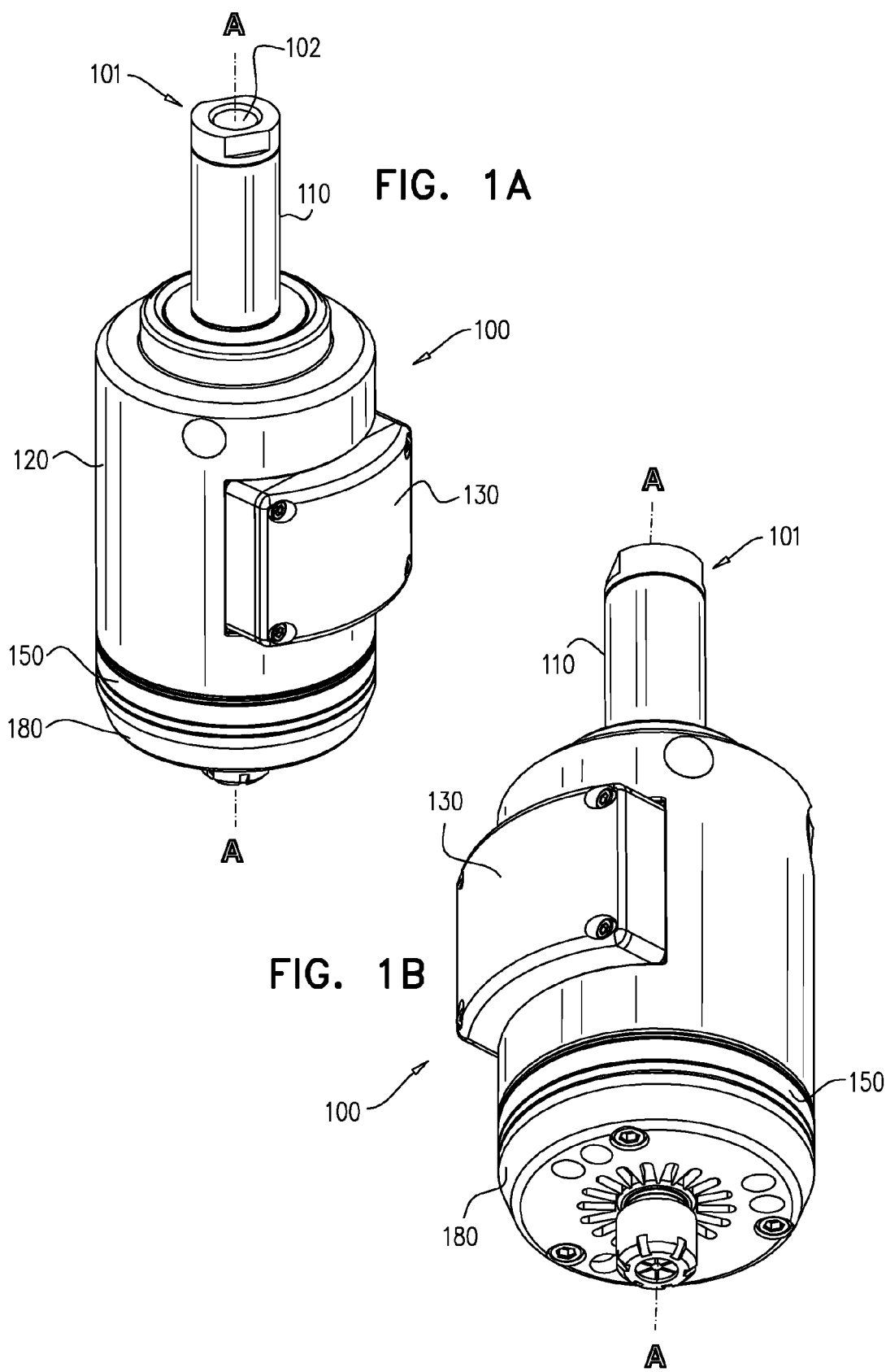

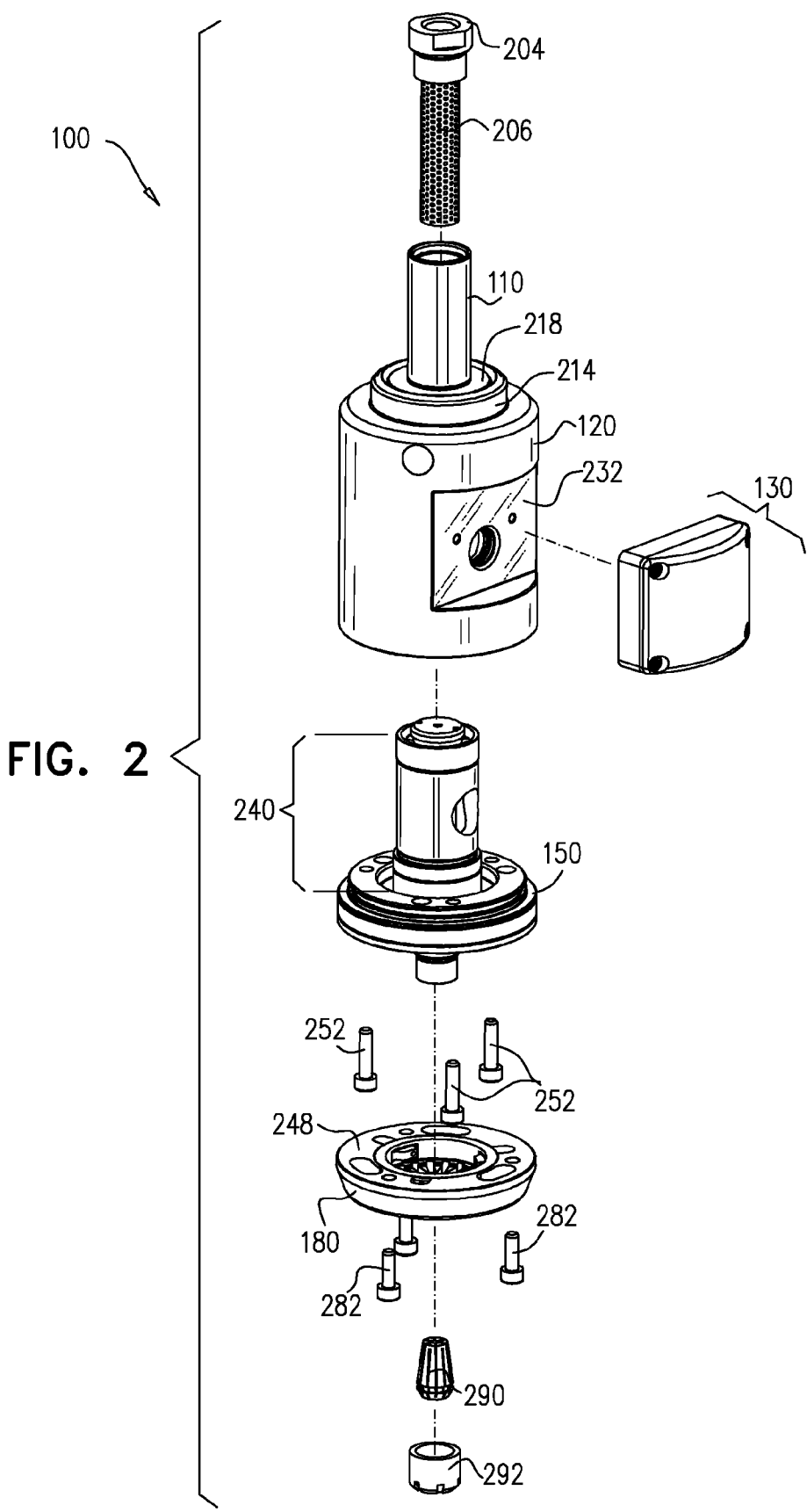

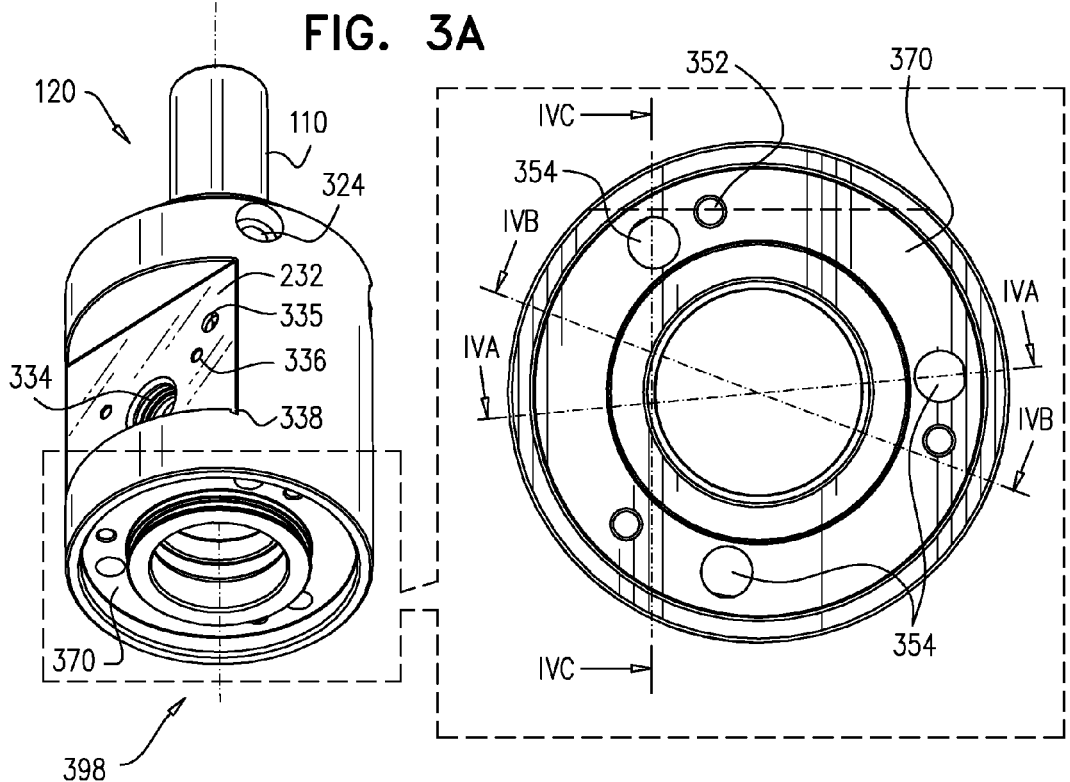
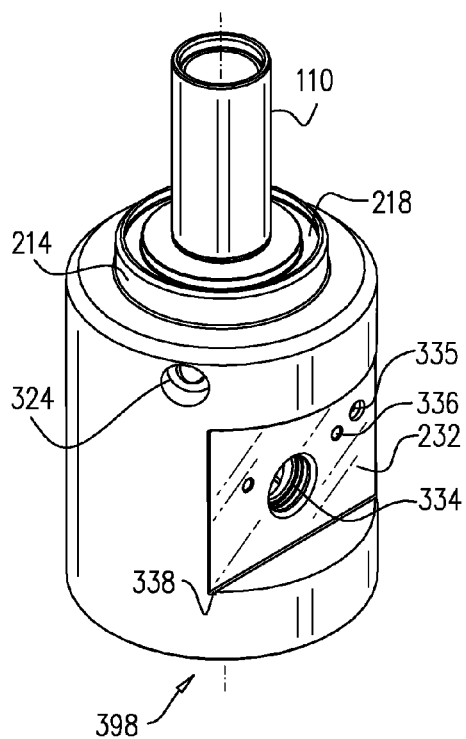
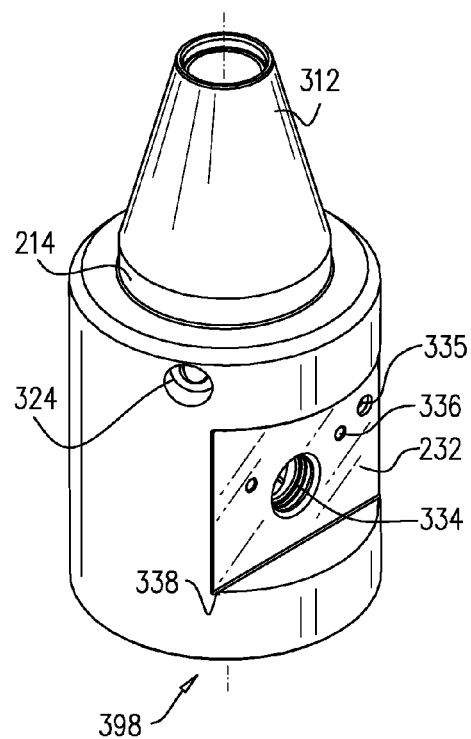

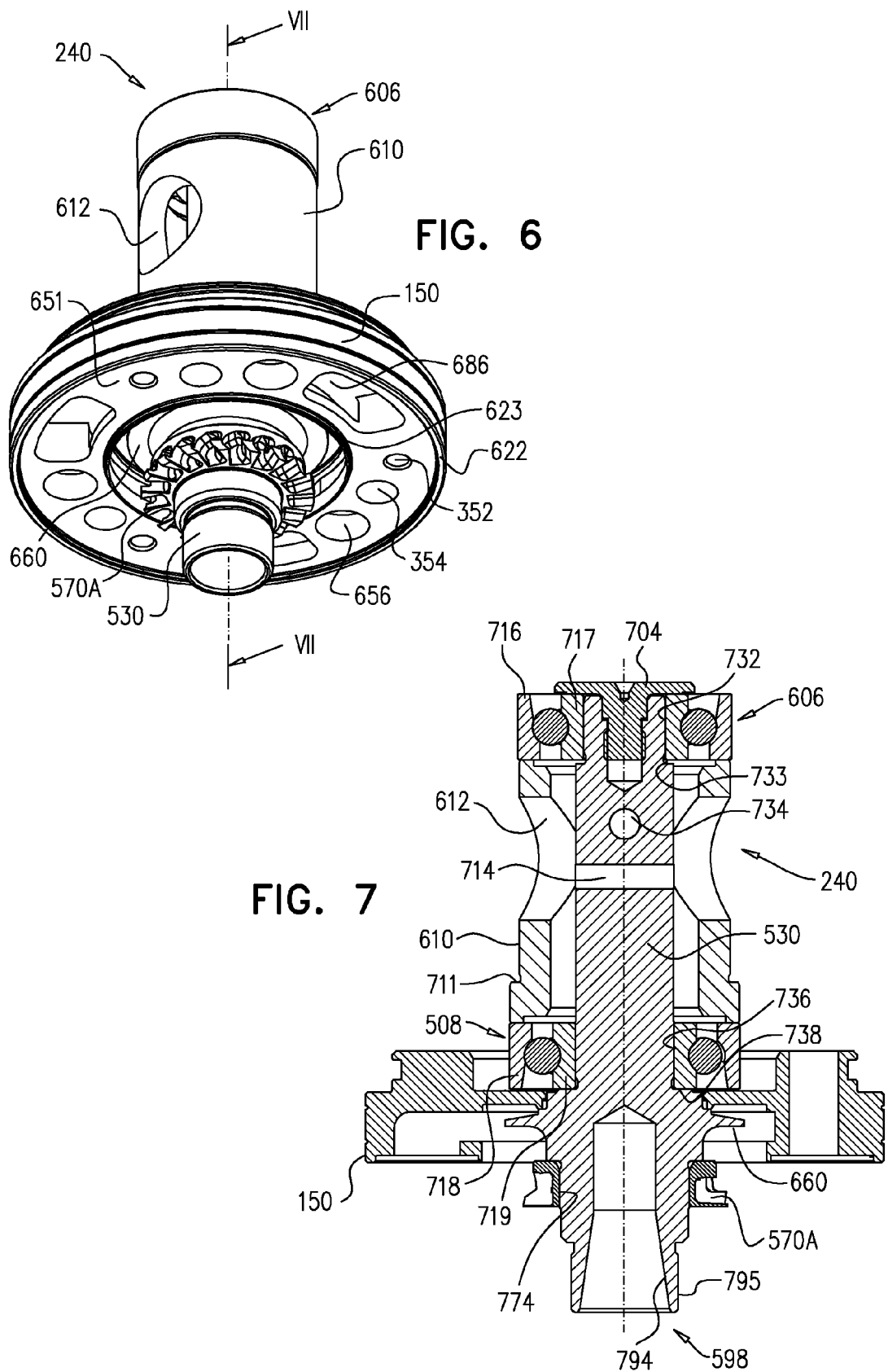

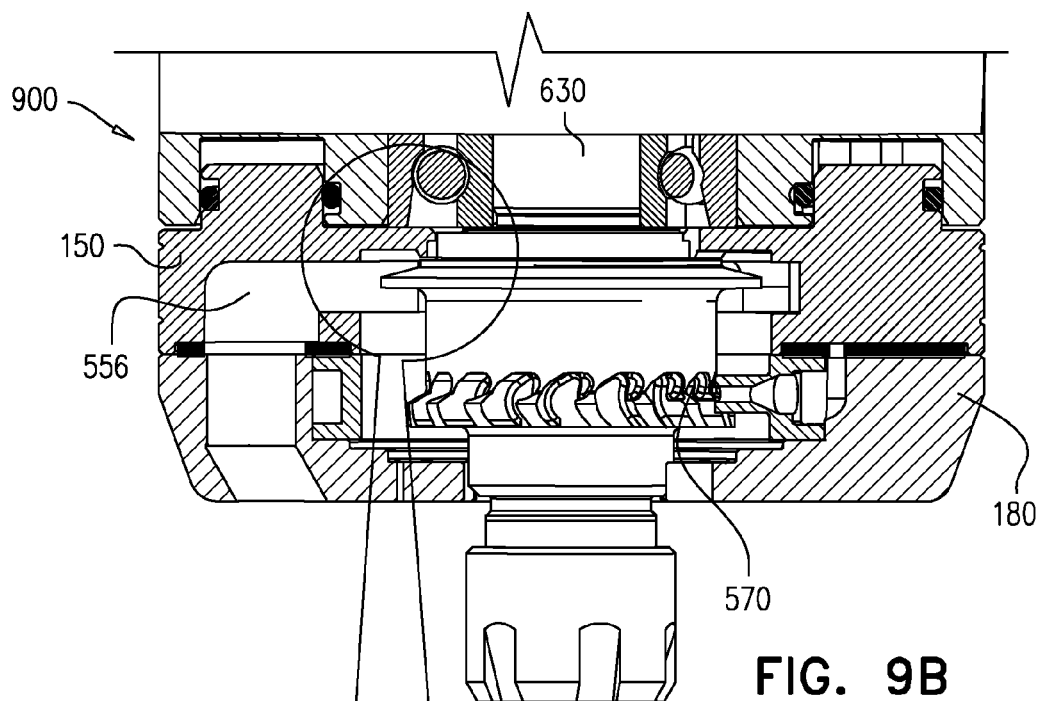
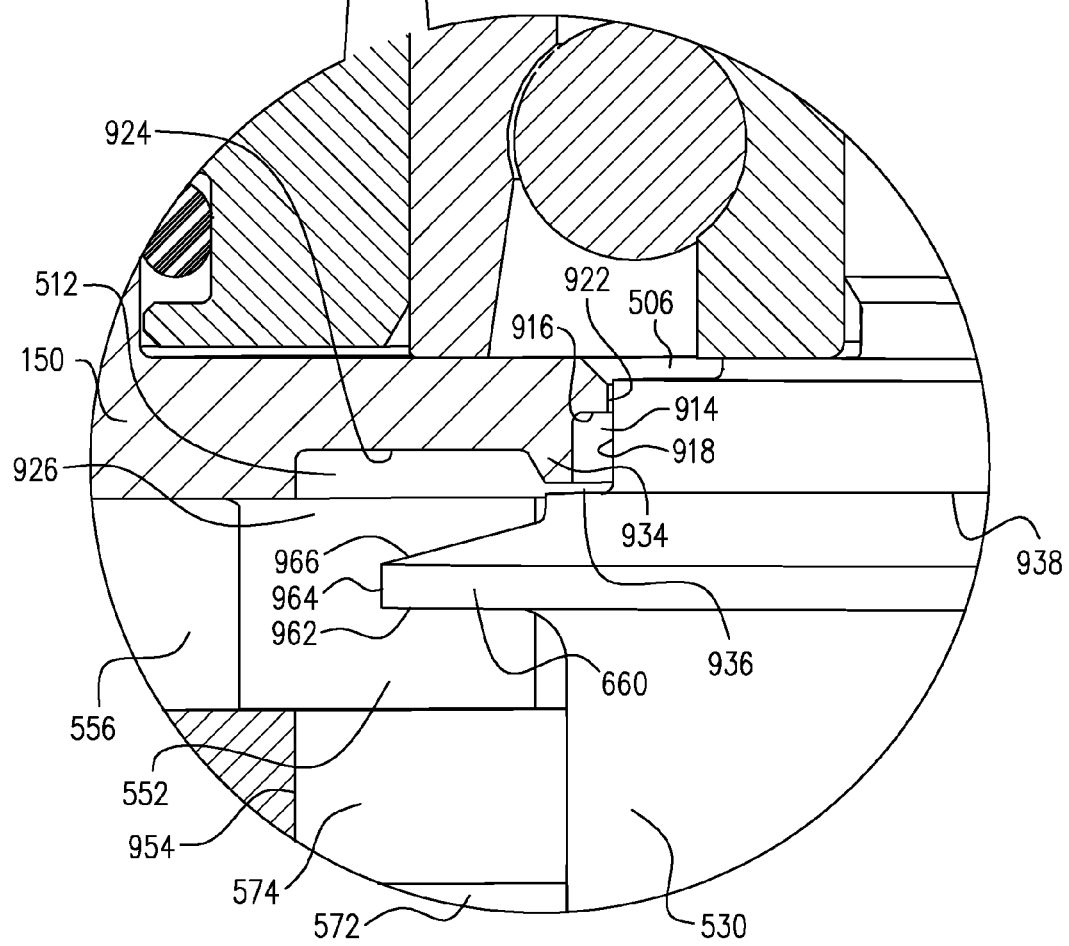

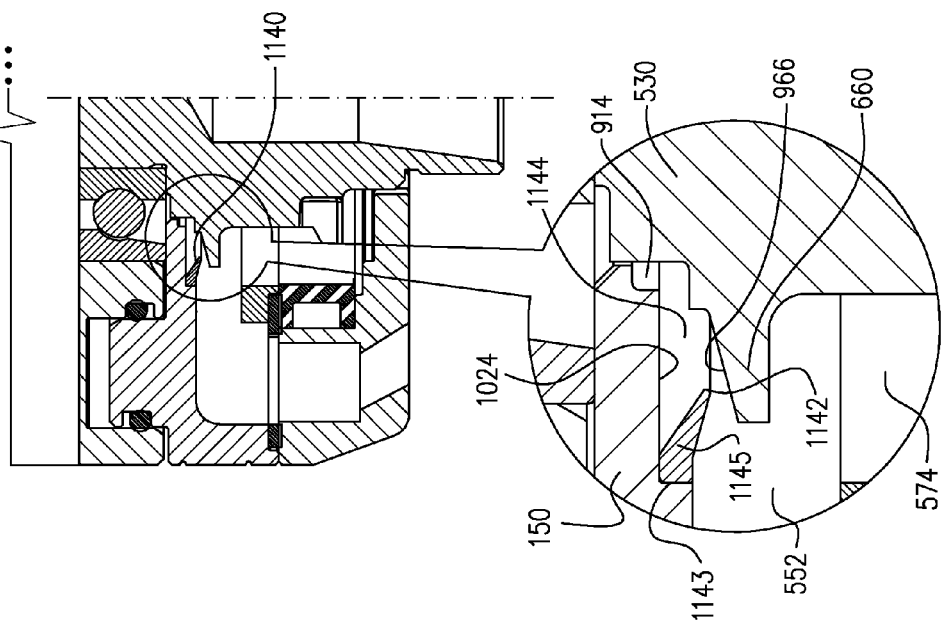
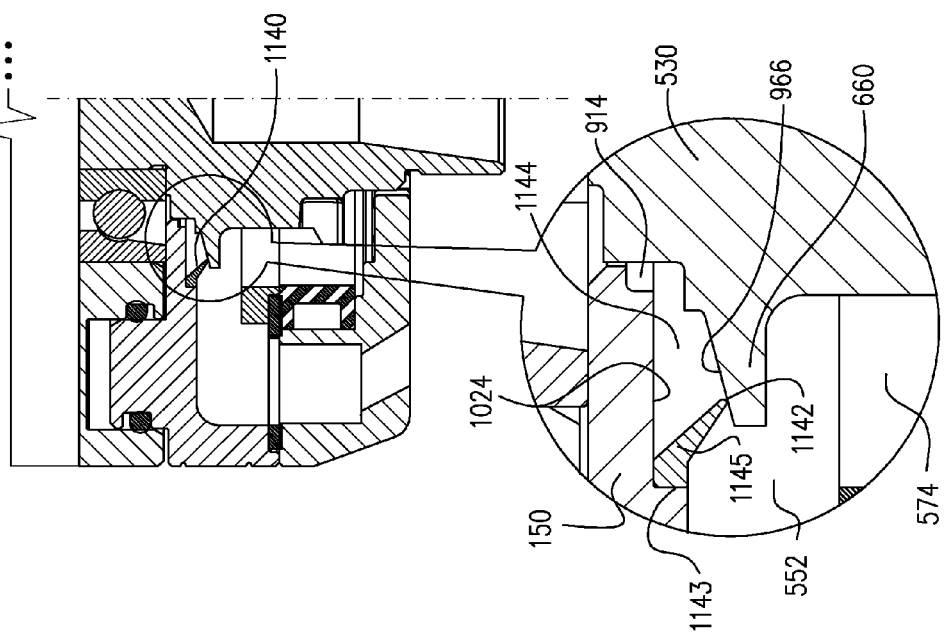

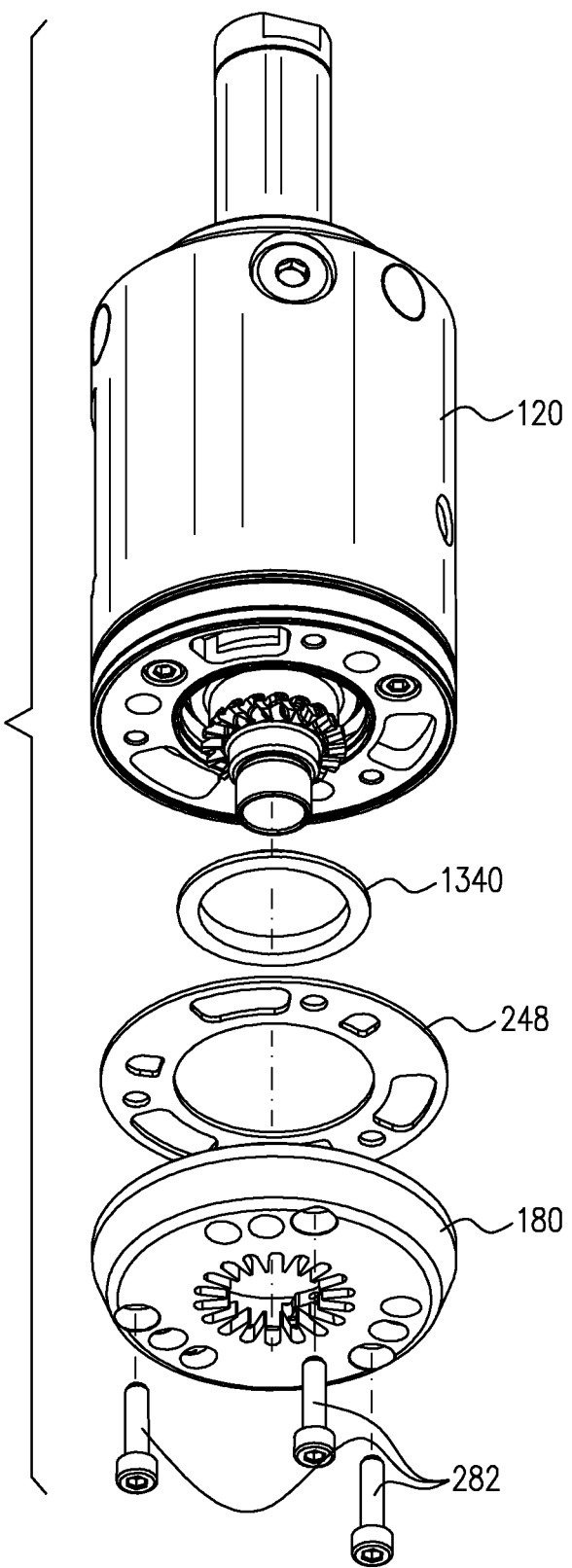

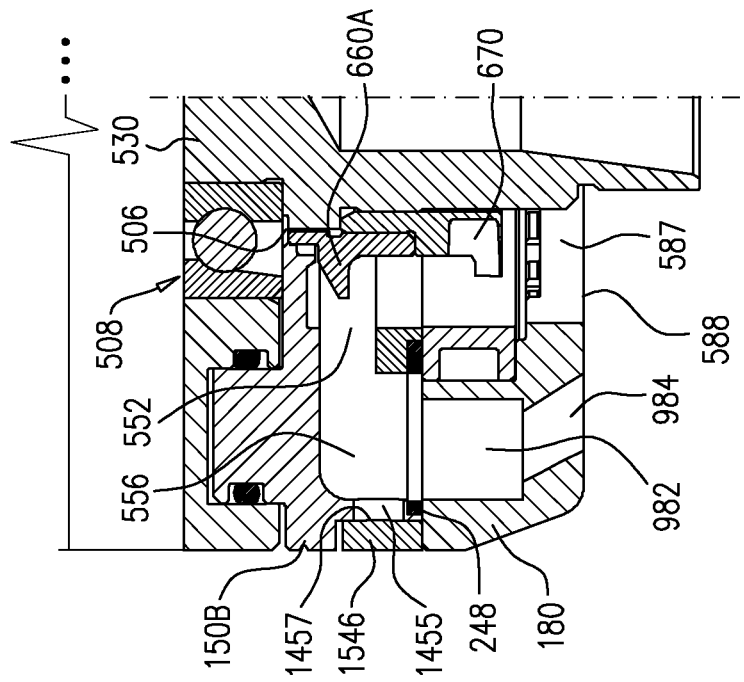
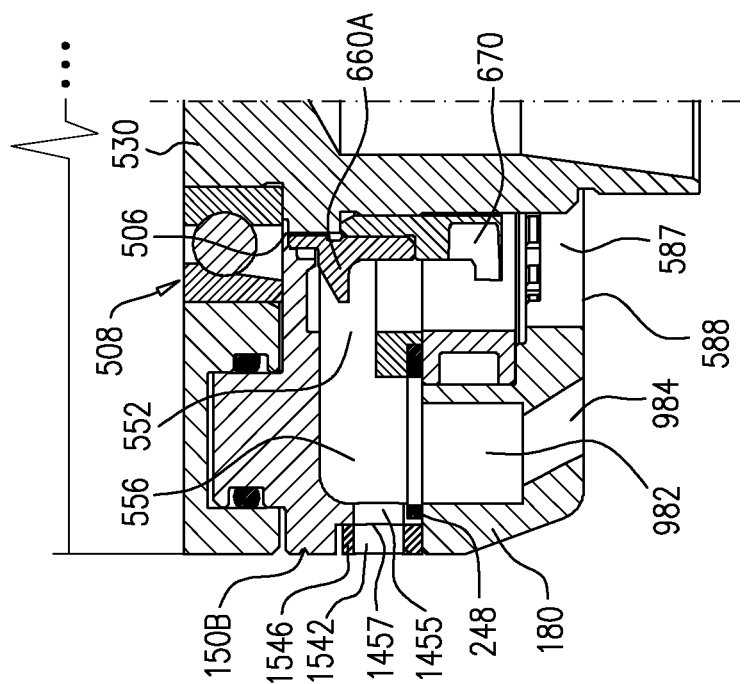

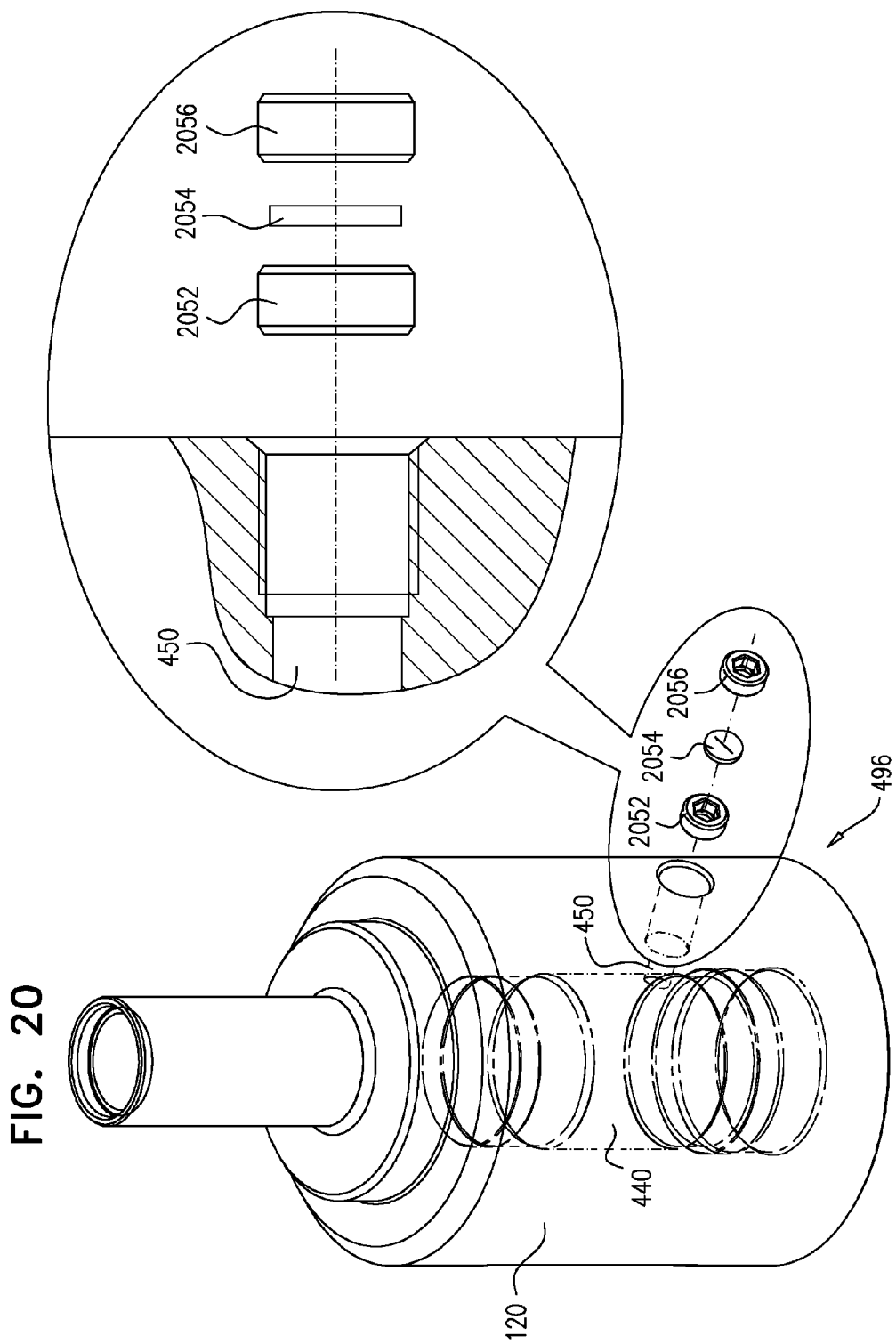

VIEW XXIIC

FLUID POWERED SPINDLE

RELATED APPLICATIONS

Priority is claimed to U.S. Provisional Patent Application No. 61/877,453, filed Sep. 13, 2013, the contents of which are incorporated by reference in their entirety.

FIELD OF THE INVENTION

This disclosure is directed to machine spindles used for rotating a tool and removing material from a work piece. Particularly, this disclosure is directed to high speed spindles to be used in combination with small diameter tools, the high speed spindles being driven by fluid, particularly liquid.

BACKGROUND

Machining with small diameter tools, for example less than 8 mm diameter, requires high speed machining capability in the range of 20,000, 30,000, 50,000 and in some cases over 100,000 RPM. Small diameter tools are typically used for applications requiring small geometries as well as general purposes applications in the semi finish and finish processes of most manufactured parts. Machining with small diameter tools is also referred to as micro machining.

In micro machining, the required rotation speeds are higher while the power requirements are relatively low compared to non-micro machining. High speed machining for semi finish and finish processes requires effective cutting tool and cutting location cooling as well as effective chip removal.

Computerized machining centers typically include an Automatic Tool Changer (ATC), such that multiple machining operations can be performed on the same part, i.e. using different tools that are changed automatically by the ATC, without removing the part. This capability provides significant cost savings, reduces manpower requirements and improves manufacturing quality and yield.

Most machining centers use electrical motor driven spindles to rotate the machining tools. General purpose machining spindles rotate at speeds of a few thousands RPM. Spindles capable of higher RPM are expensive and often used on dedicated equipment. The result is that many smaller diameter cutting tools are used at suboptimal machining conditions or that parts requiring semi finishing and or finishing operations have to be moved to other machine centers, with higher speed spindles. Both options are problematic.

Present solutions such as speed increasers and other non-electric spindles are often susceptible to problems.

SUMMARY

In a typical fluid driven high speed spindle, pressurized fluid is imparted onto turbine blades. The turbine, which is comprised of turbine blades and a central ring to which the blades are attached to, is mounted on the rotating shaft. In some cases, the shaft and central ring to which the blades are attached to, are integrated, i.e. the shaft and turbine blades are machined from one metal bar such that the central ring is part of the shaft.

The turbine blades are designed such that pressurized fluid that is imparted on at least one blade will cause the turbine and the shaft to rotate and that the fluid will deflect off the blade in a preferred direction.

Bearing lubrication is a critical factor affecting the reliability of high speed spindles. Contamination of the bearing lubricant by fluid, debris or moisture is one of the main reasons for bearing failure. Similarly, removal of a significant portion of the original bearing grease caused by fluid flow in the vicinity and/or through the bearings must be prevented in that it will affect the reliability and working life of the high speed spindle.

All rotating systems have a gap between the rotating parts and the stationary parts. In some systems, a seal is incorporated to prevent fluid from traversing the gap. Contact seals including a flexible contact component and/or a sacrificial friction surface are most common but their effectiveness is significantly reduced by high speeds and more so, in smaller diameter systems. Non-contact seal are typically expensive and bulky.

There are cases in which a portion of the fluid, does not exit the turbine in the preferred direction. In such an event, fluid may seep into the bearing cavity via the gap between the stationary body of the high speed spindle and the rotating parts, e.g. the shaft.

In some other cases, the high pressure fluid retains small particles of solid debris even after being filtered.

In yet other cases, fluid may seep into the bearing cavity when the high speed spindle is stored in an automatic tool changer (ATC) or in storage in a horizontal or upside down (cutting tool up) position, after a machining session. In such an occurrence, residual fluid that is on the turbine blades, shaft and other parts of the system, may seep into the bearing cavity via the gap between the stationary body of the high speed spindle and the rotating parts.

The phenomenon described herein is problematic in that bearing's performance degrades rapidly when the bearing comes in contact with debris and fluids, including droplets, spray, humidity etc. Performance degradation includes a reduction in stiffness which will lead to a reduction in machining accuracy. It will also reduce the bearing life span due to damage to the bearing rolling elements and or to the bearing races.

Causes for bearing damage include: changes in the lubricant properties caused by the fluid; and/or a reduction in the amount of lubricant available in the bearing because a portion of it has been washed of by the fluid; small solid debris particles that enter spaces between the bearing rolling elements and bearing races; change to the surface properties of the bearing rolling elements and or to the bearing races due for example to oxidation and/or contamination.

Reducing the gap distance between the stationary parts and the rotating parts is part of the solution. However, reducing the gap to a distance small enough such that high pressure fluid will not seep through while preventing friction contact between the parts is neither practical nor economical.

Friction components such as flexible contact seals that can prevent fluid seepage, or sealed bearings that insulate the bearing components, are used in larger and slower systems. However, they are not practical in small diameter systems designed for high speed and high fluid pressure. The seals tend to wear rapidly at the contact point (or contact line), resulting in reduced efficacy of the seal and introduction of debris into the system. Furthermore the friction caused by the seals reduces the amount of power available to the cutting process and the heat generated by the friction may require a cooling system.

Thus there is a need for sealing solutions that are economically effective for small high speed rotational systems and in particularly in systems incorporating high pressure fluid in the vicinity of the bearings.

The present invention may be cast in the form of the following paragraphs.

Paragraph 1. A liquid powered spindle (100) having a longitudinal axis (A) defining an upper end and a lower, shaft-tool end (598), comprising:
  a) a body (120) having a spindle cavity (440);
  b) at least one bearing (508) disposed in the cavity (440);
  c) a shaft (530) supported by the at least one bearing (508) within the cavity (440);
  d) a seal housing (150) connected to the body (120) at the lower end thereof;
  e) a cover (180) connected to the seal housing (150) at the lower end thereof;
  f) a fluid channel system for directing liquid from an entry port (102) to a nozzle (576);
  g) a turbine (570) attached to the shaft (530), the turbine in fluid communication with the at least one nozzle for rotating the shaft; and
  h) a flinger (660) attached to the shaft (530) and positioned above the turbine (570);
wherein the seal housing (150) defines an annular fluid manifold (552) surrounding the shaft (530) for distributing liquid, deflected upward by the turbine (570), into a plurality of stationary fluid exit channels (556);
wherein the flinger (660) and the seal housing (150) combine to form a non-contact seal (900) configured to impede the flow of liquid toward the at least one bearing (508).

Paragraph 2. The spindle of Paragraph 1, wherein the seal housing (150) further defines:
  a major turbulence pocket (512) is defined by a recess (924) within the seal housing, and positioned adjacent to the shaft (530), the major turbulence pocket being disposed above the annular fluid manifold (552) and the flinger (660).

Paragraph 3. The spindle of Paragraph 2, wherein the recess (924) has a shoulder (934) extending from the radial inner portion thereof such that the recess is capable of retaining liquid when the spindle is inverted.

Paragraph 4. The spindle of Paragraph 2, wherein the major turbulence pocket (512) includes a large opening (926) facing the annular fluid manifold (552) and a small opening (936) defined by a gap between the seal housing (150) and the flinger (660), wherein turbulence within the liquid, impedes flow of the liquid into the small opening (936).

Paragraph 5. The spindle of Paragraph 4, wherein the seal housing (150) further defines a minor turbulence pocket (914), the minor turbulence pocket (914) in communication with the small opening (936), the minor turbulence pocket (914) defined by a step-like feature (916) adjacent to the inner diameter of the seal housing (150), wherein the minor turbulence pocket (914) further impedes flow of the liquid through a vertical gap (922) between the seal housing (150) and the shaft (530).

Paragraph 6. The spindle of Paragraph 5, wherein the minor turbulence pocket (914) has a slot wall (925) extending downward from an inner diameter of a flat upper surface (923) of the minor turbulence (914).

Paragraph 7. The spindle of Paragraph 1, wherein the body (120) further comprises a vent (450) between the spindle cavity (440) and the exterior of the body, wherein the vent is sealed with a vent gasket (2054) capable of allowing flow in both directions.

Paragraph 8. The spindle of Paragraph 1, wherein the at least one bearing (508) is lubricated with grease or oil, different from the fluid.

Paragraph 9. The spindle of Paragraph 1, further comprising a sensor module (130) in communication with at least one aperture (334, 335) formed in the body (120), wherein the at least one aperture allows the sensor module to sense at least one internal characteristic of the spindle.

Paragraph 10. The spindle of Paragraph 1, wherein the at least one bearing (508) is a shielded bearing.

Paragraph 11. The spindle of Paragraph 1, wherein the fluid channel system comprises:
  i) the entry port (102) associated with a shank (110);
  ii) a shank channel (416);
  iii) at least one primarily horizontal fluid channel (422) extending from the end of the shank channel;
  iv) at least one primary vertical fluid channel (426) extending from the at least one primary horizontal fluid channel through the body; and
  v) the at least one nozzle (576) in fluid communication with the at least one primary vertical fluid channel.

Paragraph 12. The spindle of Paragraph 1, wherein the spindle comprises a wrench grip (214) positioned between the body (120) and a shank (110) to accept a wrench and assist with mounting the spindle to a chuck.

Paragraph 13. The spindle of Paragraph 1, wherein the at least one bearing (508) includes at least a pair of angular bearings (2308, 2309) contacting one another.

Paragraph 14. The spindle of Paragraph 1, wherein the cover (180) comprises at least one first axial exit opening (588) at the bottom thereof, the at least one first axial exit opening (588) provides an exit for the liquid directed downward by the turbine (570).

Paragraph 15. The spindle of Paragraph 14, wherein the cover (180) comprises at least one second axial exit opening (586) disposed radially outward with respect to the at least one first axial exit opening (588), the at least one second axial exit opening in fluid communication with the annular fluid manifold (552) in order to discharge the liquid deflected upward by the turbine (570).

Paragraph 16. The spindle of Paragraph 15, wherein the cover (180) comprises at least one axial fluid exit channel (982, 984) communicating with the at least one second axial exit opening (586), the axis of the axial fluid exit channel being angled with respect to the shaft (530) such that liquid exiting the at least one second axial exit opening (586) will be directed toward the longitudinal axis (A).

Paragraph 17. The spindle of Paragraph 1, wherein the at least one bearing is a plurality of bearings, and the plurality of bearings are of different types or dimensions.

Paragraph 18. The spindle of Paragraph 1, further comprising a stationary ring (1340) disposed within the seal housing (150), the stationary ring (1340) configured to impinge upon a seal annular gap (574) positioned below the flinger (660).

Paragraph 19. The spindle of the Paragraph 1, wherein the at least one nozzle (576) is formed along the inner diameter of a nozzle ring (977), the nozzle ring (977) is disposed within the cover (180) to define a nozzle fluid manifold (578),
wherein the at least one nozzle (576) is angled relative to the radial direction of the shaft (530) in order to impact with maximum force of the fluid on the turbine (570).

Paragraph 20. The spindle of Paragraph 1, wherein the shaft and the flinger are integrally formed.

Paragraph 21. The spindle of Paragraph 1, wherein the shaft (530) comprises a plurality of axially spaced flingers (660, 961).

Paragraph 22. The spindle of Paragraph 1, further comprising a filter mesh (206).

Paragraph 23. The spindle of Paragraph 1, wherein the body (102) comprises:
a) a shell (2120); and
b) a core (2130), the core comprising:
  i) a bearing housing cavity (2142) surrounding the spindle cavity (440); and
  ii) a shank (110); and wherein the fluid channel system further comprises:
  i) the entry port (102) associated with the shank (110);
  ii) a shank channel (216);
  iii) at least one primary horizontal fluid channel (422) extending from the end of the shank channel through the bearing housing cavity (2142);
  iv) at least one primary vertical fluid channel (426) in the shell, the at least one primary vertical fluid channel (426) in fluid communication with the at least one horizontal fluid channel through bearing housing cavity; and
  v) the at least one nozzle (576) in fluid communication with the at least one primary vertical fluid channel.

Paragraph 24. The spindle of Paragraph 23, wherein the shell (2120) has a first material having a first density and a first hardness and the core (2130) has a second material having a second density and second hardness, wherein the first density is less than the second density and the first hardness is less than the second hardness.

Paragraph 25. The spindle of Paragraph 1, wherein:
the flinger (660) is a spring flinger (1040), the spring flinger (1040) having a flexible section (1044), the spring flinger attached to the shaft (530) and positioned above the turbine (570);
wherein:
when the shaft (530) is idle the flexible section (1044) has a first position relatively close to the shaft such that the flexible section contacts and seals with a portion of the seal housing (150), and
when the shaft is rotating, the centrifugal forces generated by the rotating shaft cause the flexible section (1044) to flex away from the shaft, providing a flinger surface for deflecting the liquid, and removing contact with the seal housing (150).

Paragraph 26. The spindle of Paragraph 1, further comprising:
a flexible flap (1140) mounted within the seal housing (150);
wherein: when pressurized liquid is not present in the spindle, the flexible flap forms a contact seal between the flinger (660) and the seal housing (150) to prevent residual liquid from contaminating the at least one bearing (508), and
when pressurized liquid is present within the spindle, the flexible flap (1140) is deflected away from the flinger (660) to eliminate contact therewith.

Paragraph 27. The spindle of Paragraph 26, wherein the flexible flap (1140) is deflected by pressurized liquid within the annular fluid manifold (552).

Paragraph 28. The spindle of Paragraph 26, wherein the flexible flap (1140A) includes an internal cavity (1147A) in fluid communication with the fluid channel system such that fluid pressure within the fluid channel system causes the flexible flap (1140A) to flex away from the flinger (660).

Spindles with Two-Part Bodies

Paragraph 29. A liquid powered spindle (100) having a longitudinal axis (A) defining an upper end and a lower, shaft-tool end (598), comprising:
  a) a shell (2120);
  b) a core (2130), the core comprising:
    i) a cavity housing (2142) disposed within the core; and
    ii) a shank (110);
  c) at least one bearing (508) disposed in the cavity housing; and
  d) a shaft (530) supported by the at least one bearing (508) within the cavity housing for rotating a tool;
wherein the shell and core collectively define a fluid channel system comprising:
  i) an entry port (102) associated with the shank (110);
  ii) a shank channel (216);
  iii) at least one primary horizontal fluid channel (422) extending from the end of the shank channel through the bearing housing cavity (2142);
  iv) at least one primary vertical fluid channel (426) in the shell, the at least one primary vertical fluid channel (426) in fluid communication with the at least one horizontal fluid channel through bearing housing cavity; and
  v) at least one nozzle (576) in fluid communication with the at least one primary vertical fluid channel;
wherein the shaft comprises at least one turbine (570) in fluid communication with the at least one nozzle for rotating the shaft using pressurized liquid;
  e) a flinger (660) attached to the shaft (530) and positioned above the turbine (570);
  f) a seal housing (150) connected to the core (2130) at the lower end thereof; and
  g) a cover (180) connected to the seal housing (150) at the lower end thereof;
wherein the seal housing (150) defines an annular fluid manifold (552) surrounding the shaft (530) for distributing liquid, deflected upward by the turbine (570), into a plurality of stationary fluid exit channels (556);
wherein the flinger (660) and the seal housing (150) combine to form a non-contact seal (900) configured to impede the flow of liquid toward the at least one bearing (508).

Paragraph 30. The spindle of Paragraph 29, wherein the shell (2120) has a first material having a first density and a first hardness and the core (2130) has a second material having a second density and second hardness, wherein the first density is less than the second density and the first hardness is less than the second hardness.

Paragraph 31. The spindle of Paragraph 29, wherein the seal housing (150) further defines:
a major turbulence pocket (512) is defined by a recess (924) within the seal housing, and positioned adjacent to the shaft (530), the major turbulence pocket being disposed above the annular fluid manifold (552) and the flinger (660).

Paragraph 32. The spindle of Paragraph 31, wherein the recess (924) has a shoulder (934) extending from the radial inner portion thereof such that the recess is capable of retaining liquid when the spindle is inverted.

Paragraph 33. The spindle of Paragraph 31, wherein the major turbulence pocket (512) includes a large opening (926) facing the annular fluid manifold (552) and a small opening (936) defined by a gap between the seal housing (150) and the flinger (660), wherein turbulence within the liquid, impedes flow of the liquid into the small opening (936).

Paragraph 34. The spindle of Paragraph 33, wherein the seal housing (150) further defines a minor turbulence pocket (914) radially inward of the major turbulence pocket (512), the minor turbulence pocket (914) in communication with the small opening (936), the minor turbulence pocket (914) defined by a step-like feature (916) adjacent to the inner diameter of the seal housing (150), wherein the minor turbulence pocket (914) further impedes flow of the liquid through a vertical gap (922) between the seal housing (150) and the shaft (530).

Paragraph 35. The spindle of Paragraph 34, wherein the minor turbulence pocket (914) has a slot wall (925) extending downward from an inner diameter of a flat upper surface (923) of the minor turbulence (914).

Paragraph 36. The spindle of Paragraph 29, wherein the shell and core further comprise a vent (450) between the spindle cavity (440) and the exterior of the shell, wherein the vent is sealed with a vent gasket (2054) capable of allowing flow in both directions.

Paragraph 37. The spindle of Paragraph 29, wherein the at least one bearing (508) is lubricated with grease or oil, different from the fluid.

Paragraph 38. The spindle of Paragraph 29, further comprising a sensor module (130) in communication with at least one aperture (334, 335) formed in the shell and the core, wherein the at least one aperture allows the sensor module to sense at least one internal characteristic of the spindle.

Paragraph 39. The spindle of Paragraph 29, wherein the at least one bearing (508) is a shielded bearing.

Paragraph 40. The spindle of Paragraph 29, wherein the spindle comprises a wrench grip (214) positioned between the shell and a shank (110) to accept a wrench and assist with mounting the spindle to a chuck.

Paragraph 41. The spindle of Paragraph 29, wherein the at least one bearing (508) includes at least a pair of angular bearings (2308, 2309) contacting one another.

Paragraph 42. The spindle of Paragraph 29, wherein the cover (180) comprises at least one first axial exit opening (588) at the bottom thereof, the at least one first axial exit opening (588) provides an exit for the liquid directed downward by the turbine (570).

Paragraph 43. The spindle of Paragraph 42, wherein the cover (180) comprises at least one second axial exit opening (586) disposed radially outward with respect to the at least one first axial exit opening (588), the at least one second axial exit opening in fluid communication with the annular fluid manifold (552) in order to discharge the liquid deflected upward by the turbine (570).

Paragraph 44. The spindle of Paragraph 43, wherein the cover (180) comprises at least one axial fluid exit channel (982, 984) communicating with the at least one second axial exit opening (586), the axis of the axial fluid exit channel being angled with respect to the shaft (530) such that liquid exiting the at least one second axial exit opening (586) will be directed toward the longitudinal axis (A).

Paragraph 45. The spindle of Paragraph 30, wherein the at least one bearing is a plurality of bearings, and the plurality of bearings are of different types or dimensions.

Paragraph 46. The spindle of Paragraph 29, further comprising a stationary ring (1340) disposed within the seal housing (150), the stationary ring (1340) configured to impinge upon a seal annular gap (574) positioned below the flinger (660).

Paragraph 47. The spindle of the Paragraph 29, wherein the at least one nozzle (576) is formed along the inner diameter of a nozzle ring (977), the nozzle ring (977) is disposed within the cover (180) to define a nozzle fluid manifold (578), wherein the at least one nozzle (576) is angled relative to the radial direction of the shaft (530) in order to impact with maximum force of the fluid on the turbine (570).

Paragraph 48. The spindle of Paragraph 29, wherein the shaft and the flinger are integrally formed.

Paragraph 49. The spindle of Paragraph 29, wherein the shaft (530) comprises a plurality of axially spaced flingers (660, 961).

Paragraph 50. The spindle of Paragraph 29, further comprising a filter mesh (206).

Paragraph 51. The spindle of Paragraph 29, wherein: the flinger (660) is a spring flinger (1040), the spring flinger (1040) having a flexible section (1044), the spring flinger attached to the shaft (530) and positioned above the turbine (570);

wherein:
when the shaft (530) is idle the flexible section (1044) has a first position relatively close to the shaft such that the flexible section contacts and seals with a portion of the seal housing (150), and
when the shaft is rotating, the centrifugal forces generated by the rotating shaft cause the flexible section (1044) to flex away from the shaft, providing a flinger surface for deflecting the liquid, and removing contact with the seal housing (150).

Paragraph 52. The spindle of Paragraph 29, further comprising:
a flexible flap (1140) mounted within the seal housing (150);
wherein: when pressurized liquid is not present in the spindle, the flexible flap forms a contact seal between the flinger (660) and the seal housing (150) to prevent residual liquid from contaminating the at least one bearing (508), and
when pressurized liquid is present within the spindle, the flexible flap (1140) is deflected away from the flinger (660) to eliminate contact therewith.

Paragraph 53. The spindle of Paragraph 52, wherein the flexible flap (1140) is deflected by pressurized liquid within the annular fluid manifold (552).

Paragraph 54. The spindle of Paragraph 52, wherein the flexible flap (1140A) includes an internal cavity (1147A) in fluid communication with the fluid channel system such that fluid pressure within the fluid channel system causes the flexible flap (1140A) to flex away from the flinger (660).

Spindles with Flexible Flingers

Paragraph 55. A liquid powered spindle (100) having a longitudinal axis (A) defining an upper end and a lower, shaft-tool end (598), comprising:
a) a body (120) having a spindle cavity (440);
b) at least one bearing (508) disposed in the cavity (440);
c) a shaft (530) supported by the at least one bearing (508) within the cavity (440);
d) a seal housing (150) connected to the body (120) at the lower end thereof, the seal housing defining an annular fluid manifold (552) surrounding the shaft (530) for distributing liquid, deflected upward by the turbine (570), into a plurality of stationary fluid exit channels (556);
e) a cover (180) connected to the seal housing (150) at the lower end thereof;
f) a fluid channel system for directing liquid from an entry port (102) to a nozzle (576);
g) a turbine (570) attached to the shaft (530), the turbine in fluid communication with the at least one nozzle for rotating the shaft; and
h) a spring flinger (1040) having a flexible section (1044), the spring flinger attached to the shaft (530) and positioned above the turbine (570);
wherein:
when the shaft (530) is idle the flexible section (1044) has a first position relatively close to the shaft such that the flexible section contacts and seals with a portion of the seal housing (150), and
when the shaft is rotating, the centrifugal forces generated by the rotating shaft cause the flexible section (1044) to flex away from the shaft, providing a flinger surface for deflecting the liquid, and removing contact with the seal housing (150).

Paragraph 56. The spindle of Paragraph 55, wherein the seal housing (150) further defines:
a major turbulence pocket (512) is defined by a recess (924) within the seal housing, and positioned adjacent to the shaft (530), the major turbulence pocket being disposed above the annular fluid manifold (552) and the flinger (660).

Paragraph 57. The spindle of Paragraph 56, wherein the recess (924) has a shoulder (934) extending from the radial inner portion thereof such that the recess is capable of retaining liquid when the spindle is inverted.

Paragraph 58. The spindle of Paragraph 56, wherein the major turbulence pocket (512) includes a large opening (926) facing the annular fluid manifold (552) and a small opening (936) defined by a gap between the seal housing (150) and the flinger (660), wherein turbulence within the liquid, impedes flow of the liquid into the small opening (936).

Paragraph 59. The spindle of Paragraph 58, wherein the seal housing (150) further defines a minor turbulence pocket (914) radially inward of the major turbulence pocket (512), the minor turbulence pocket (914) in communication with the small opening (936), the minor turbulence pocket (914) defined by a step-like feature (916) adjacent to the inner diameter of the seal housing (150), wherein the minor turbulence pocket (914) further impedes flow of the liquid through a vertical gap (922) between the seal housing (150) and the shaft (530).

Paragraph 60. The spindle of Paragraph 59, wherein the minor turbulence pocket (914) has a slot wall (925) extending downward from an inner diameter of a flat upper surface (923) of the minor turbulence (914).

Paragraph 61. The spindle of Paragraph 55, wherein the body (120) further comprises a vent (450) between the spindle cavity (440) and the exterior of the body, wherein the vent is sealed with a vent gasket (2054) capable of allowing flow in both directions.

Paragraph 62. The spindle of Paragraph 55, wherein the at least one bearing (508) is lubricated with grease or oil, different from the fluid.

Paragraph 63. The spindle of Paragraph 55, further comprising a sensor module (130) in communication with at least one aperture (334, 335) formed in the body (120), wherein the at least one aperture allows the sensor module to sense at least one internal characteristic of the spindle.

Paragraph 64. The spindle of Paragraph 55, wherein the at least one bearing (508) is a shielded bearing.

Paragraph 65. The spindle of Paragraph 55, wherein the fluid channel system comprises:
  i) the entry port (102) associated with a shank (110);
  ii) a shank channel (416);
  iii) at least one primarily horizontal fluid channel (422) extending from the end of the shank channel;
  iv) at least one primary vertical fluid channel (426) extending from the at least one primary horizontal fluid channel through the body; and
  v) the at least one nozzle (576) in fluid communication with the at least one primary vertical fluid channel.

Paragraph 66. The spindle of Paragraph 55, wherein the spindle comprises a wrench grip (214) positioned between the body (120) and a shank (110) to accept a wrench and assist with mounting the spindle to a chuck.

Paragraph 67. The spindle of Paragraph 55, wherein the at least one bearing (508) includes at least a pair of angular bearings (2308, 2309) contacting one another.

Paragraph 68. The spindle of Paragraph 57, wherein the cover (180) comprises at least one first axial exit opening (588) at the bottom thereof, the at least one first axial exit opening (588) provides an exit for the liquid directed downward by the turbine (570).

Paragraph 69. The spindle of Paragraph 68, wherein the cover (180) comprises at least one second axial exit opening (586) disposed radially outward with respect to the at least one first axial exit opening (588), the at least one second axial exit opening in fluid communication with the annular fluid manifold (552) in order to discharge the liquid deflected upward by the turbine (570).

Paragraph 70. The spindle of Paragraph 69, wherein the cover (180) comprises at least one axial fluid exit channel (982, 984) communicating with the at least one second axial exit opening (586), the axis of the axial fluid exit channel being angled with respect to the shaft (530) such that liquid exiting the at least one second axial exit opening (586) will be directed toward the longitudinal axis (A).

Paragraph 71. The spindle of Paragraph 55, wherein the at least one bearing is a plurality of bearings, and the plurality of bearings are of different types or dimensions.

Paragraph 72. The spindle of Paragraph 55, further comprising a stationary ring (1340) disposed within the seal housing (150), the stationary ring (1340) configured to impinge upon a seal annular gap (574) positioned below the flinger (660).

Paragraph 73. The spindle of the Paragraph 55, wherein the at least one nozzle (576) is formed along the inner diameter of a nozzle ring (977), the nozzle ring (977) is disposed within the cover (180) to define a nozzle fluid manifold (578), wherein the at least one nozzle (576) is angled relative to the radial direction of the shaft (530) in order to impact with maximum force of the fluid on the turbine (570).

Paragraph 74. The spindle of Paragraph 55, wherein the shaft and the flinger are adhered together.

Paragraph 75. The spindle of Paragraph 55, wherein the shaft (530) comprises a plurality of axially spaced flingers (660, 961).

Paragraph 76. The spindle of Paragraph 55, further comprising a filter mesh (206).

Paragraph 77. The spindle of Paragraph 55, wherein the body (102) comprises:
a) a shell (2120); and
b) a core (2130), the core comprising:
  i) a bearing housing cavity (2142) surrounding the spindle cavity (440); and
  ii) a shank (110); and
wherein the fluid channel system further comprises:
  i) the entry port (102) associated with the shank (110);
  ii) a shank channel (216);
  iii) at least one primary horizontal fluid channel (422) extending from the end of the shank channel through the bearing housing cavity (2142);
  iv) at least one primary vertical fluid channel (426) in the shell, the at least one primary vertical fluid channel (426) in fluid communication with the at least one horizontal fluid channel through bearing housing cavity; and
  v) the at least one nozzle (576) in fluid communication with the at least one primary vertical fluid channel.

Paragraph 78. The spindle of Paragraph 77, wherein the shell (2120) has a first material having a first density and a first hardness and the core (2130) has a second material having a second density and second hardness, wherein the first density is less than the second density and the first hardness is less than the second hardness.

Spindles with Flexible Flaps

Paragraph 79. A liquid powered spindle (100) having a longitudinal axis (A) defining an upper end and a lower, shaft-tool end (598), comprising:
  a) a body (120) having a spindle cavity (440);
  b) at least one bearing (508) disposed in the cavity (440);
  c) a shaft (530) supported by the at least one bearing (508) within the cavity (440);

d) a seal housing (150) connected to the body (120) at the lower end thereof, the seal housing defining an annular fluid manifold (552) surrounding the shaft (530) for distributing liquid, deflected upward by the turbine (570), into a plurality of stationary fluid exit channels (556);

e) a cover (180) connected to the seal housing (150) at the lower end thereof;

f) a fluid channel system for directing liquid from an entry port (102) to a nozzle (576);

g) a turbine (570) attached to the shaft (530), the turbine in fluid communication with the at least one nozzle for rotating the shaft; and h) a flinger (660) attached to the shaft (530) and positioned above the turbine (570); and i) a flexible flap (1140) mounted within the seal housing (150);

wherein: when pressurized liquid is not present in the spindle, the flexible flap forms a contact seal between the flinger (660) and the seal housing (150) to prevent residual liquid from contaminating the at least one bearing (508), and when pressurized liquid is present within the spindle, the flexible flap (1140) is deflected away from the flinger (660) to eliminate contact therewith.

Paragraph 80. The spindle of Paragraph 79, wherein the flexible flap (1140) is deflected by pressurized liquid within the annular fluid manifold (552).

Paragraph 81. The spindle of Paragraph 79, wherein the flexible flap (1140A) includes an internal cavity (1147A) in fluid communication with the fluid channel system such that fluid pressure within the fluid channel system causes the flexible flap (1140A) to flex away from the flinger (660).

Paragraph 82. The spindle of Paragraph 79, wherein the seal housing (150) further defines:

a major turbulence pocket (512) is defined by a recess (924) within the seal housing, and positioned adjacent to the shaft (530), the major turbulence pocket being disposed above the annular fluid manifold (552) and the flinger (660).

Paragraph 83. The spindle of Paragraph 82, wherein the recess (924) has a shoulder (934) extending from the radial inner portion thereof such that the recess is capable of retaining liquid when the spindle is inverted.

Paragraph 84. The spindle of Paragraph 82, wherein the major turbulence pocket (512) includes a large opening (926) facing the annular fluid manifold (552) and a small opening (936) defined by a gap between the seal housing (150) and the flinger (660), wherein turbulence within the liquid, impedes flow of the liquid into the small opening (936).

Paragraph 85. The spindle of Paragraph 84, wherein the seal housing (150) further defines a minor turbulence pocket (914) radially inward of the major turbulence pocket (512), the minor turbulence pocket (914) in communication with the small opening (936), the minor turbulence pocket (914) defined by a step-like feature (916) adjacent to the inner diameter of the seal housing (150), wherein the minor turbulence pocket (914) further impedes flow of the liquid through a vertical gap (922) between the seal housing (150) and the shaft (530).

Paragraph 86. The spindle of Paragraph 85, wherein the minor turbulence pocket (914) has a slot wall (925) extending downward from an inner diameter of a flat upper surface (923) of the minor turbulence (914).

Paragraph 87. The spindle of Paragraph 79, wherein the body (120) further comprises a vent (450) between the spindle cavity (440) and the exterior of the body, wherein the vent is sealed with a vent gasket (2054) capable of allowing flow in both directions.

Paragraph 88. The spindle of Paragraph 79, wherein the at least one bearing (508) is lubricated with grease or oil, different from the fluid.

Paragraph 89. The spindle of Paragraph 79, further comprising a sensor module (130) in communication with at least one aperture (334, 335) formed in the body (120), wherein the at least one aperture allows the sensor module to sense at least one internal characteristic of the spindle.

Paragraph 90. The spindle of Paragraph 79, wherein the at least one bearing (508) is a shielded bearing.

Paragraph 91. The spindle of Paragraph 79, wherein the fluid channel system comprises:

i) the entry port (102) associated with a shank (110);

ii) a shank channel (416);

iii) at least one primarily horizontal fluid channel (422) extending from the end of the shank channel;

iv) at least one primary vertical fluid channel (426) extending from the at least one primary horizontal fluid channel through the body; and v) the at least one nozzle (576) in fluid communication with the at least one primary vertical fluid channel.

Paragraph 92. The spindle of Paragraph 79, wherein the spindle comprises a wrench grip (214) positioned between the body (120) and a shank (110) to accept a wrench and assist with mounting the spindle to a chuck.

Paragraph 93. The spindle of Paragraph 79, wherein the at least one bearing (508) includes at least a pair of angular bearings (2308, 2309) contacting one another.

Paragraph 94. The spindle of Paragraph 79, wherein the cover (180) comprises at least one first axial exit opening (588) at the bottom thereof, the at least one first axial exit opening (588) provides an exit for the liquid directed downward by the turbine (570).

Paragraph 95. The spindle of Paragraph 94, wherein the cover (180) comprises at least one second axial exit opening (586) disposed radially outward with respect to the at least one first axial exit opening (588), the at least one second axial exit opening in fluid communication with the annular fluid manifold (552) in order to discharge the liquid deflected upward by the turbine (570).

Paragraph 96. The spindle of Paragraph 95, wherein the cover (180) comprises at least one axial fluid exit channel (982, 984) communicating with the at least one second axial exit opening (586), the axis of the axial fluid exit channel being angled with respect to the shaft (530) such that liquid exiting the at least one second axial exit opening (586) will be directed toward the longitudinal axis (A).

Paragraph 97. The spindle of Paragraph 79, wherein the at least one bearing is a plurality of bearings, and the plurality of bearings are of different types or dimensions.

Paragraph 98. The spindle of Paragraph 79, further comprising a stationary ring (1340) disposed within the seal housing (150), the stationary ring (1340) configured to impinge upon a seal annular gap (574) positioned below the flinger (660).

Paragraph 99. The spindle of the Paragraph 79, wherein the at least one nozzle (576) is formed along the inner diameter of a nozzle ring (977), the nozzle ring (977) is disposed within the cover (180) to define a nozzle fluid manifold (578), wherein the at least one nozzle (576) is angled relative to the radial direction of the shaft (530) in order to impact with maximum force of the fluid on the turbine (570).

Paragraph 100. The spindle of Paragraph 79, wherein the shaft and the flinger are integrally formed.

Paragraph 101. The spindle of Paragraph 79, wherein the shaft (530) comprises a plurality of axially spaced flingers (660, 961).

Paragraph 102. The spindle of Paragraph 79, further comprising a filter mesh (206).

Paragraph 103. The spindle of Paragraph 79, wherein the body (102) comprises:
a) a shell (2120); and
b) a core (2130), the core comprising:
  i) a bearing housing cavity (2142) surrounding the spindle cavity (440); and
  ii) a shank (110); and
wherein the fluid channel system further comprises:
  i) the entry port (102) associated with the shank (110);
  ii) a shank channel (216);
  iii) at least one primary horizontal fluid channel (422) extending from the end of the shank channel through the bearing housing cavity (2142);
  iv) at least one primary vertical fluid channel (426) in the shell, the at least one primary vertical fluid channel (426) in fluid communication with the at least one horizontal fluid channel through bearing housing cavity; and
  v) the at least one nozzle (576) in fluid communication with the at least one primary vertical fluid channel.

Paragraph 104. The spindle of Paragraph 103, wherein the shell (2120) has a first material having a first density and a first hardness and the core (2130) has a second material having a second density and second hardness, wherein the first density is less than the second density and the first hardness is less than the second hardness.

Spindles with Sensor Module

Paragraph 105. A fluid powered spindle (100) having a longitudinal axis (A) defining an upper end and a lower, shaft-tool end (598), comprising:
  a) a body (120) having a fluid channel system, a spindle cavity (440), and at least one aperture (334);
  b) a shaft (530) having a turbine (570), wherein the shaft is rotated by a pressurized fluid striking the turbine; and
  c) at least one sensor module (130) mounted to the body in association with the at least one aperture such that the at least one aperture allows the at least one sensor module to sense internal characteristics of the spindle.

Paragraph 106. The spindle of Paragraph 105, wherein the at least one aperture is a sensing aperture providing a path from the sensor module to the spindle cavity.

Paragraph 107. The spindle of Paragraph 106, wherein the shaft includes a rotational position reference (714) for detection by the sensor module.

Paragraph 108. The spindle of Paragraph 105, wherein the at least one aperture includes a fluid aperture (335) in fluid communication with the fluid channel system to sense fluid system properties thereof.

Paragraph 109. The spindle of Paragraph 108, wherein the fluid system properties include at least one of fluid pressure, fluid velocity and fluid viscosity.

Paragraph 110. The spindle of Paragraph 105, wherein the at least one sensor module is wireless.

Paragraph 111. The spindle of Paragraph 105, further comprising:
  a) at least one bearing (508) disposed in the spindle cavity (440);
  b) the shaft (530) supported by the at least one bearing (508) within the cavity (440);
  c) a seal housing (150) connected to the body (120) at the lower end thereof;
  d) a cover (180) connected to the seal housing (150) at the lower end thereof;
  e) the fluid channel system configured to direct liquid from an entry port (102) to a nozzle (576);
  g) the turbine in fluid communication with the at least one nozzle for rotating the shaft; and
  h) a flinger (660) attached to the shaft above the turbine;
  wherein the seal housing (150) defines an annular fluid manifold (552) surrounding the shaft (530) for distributing liquid, deflected upward by the turbine (570), into a plurality of stationary fluid exit channels (556);
  wherein the flinger (660) and the seal housing (150) combine to form a non-contact seal (900) configured to impede the flow of liquid toward the at least one bearing (508).

Paragraph 112. The spindle of Paragraph 111, wherein the seal housing (150) further defines:
a major turbulence pocket (512) is defined by a recess (924) within the seal housing, and positioned adjacent to the shaft (530), the major turbulence pocket being disposed above the annular fluid manifold (552) and the flinger (660).

Paragraph 113. The spindle of Paragraph 112, wherein the recess (924) has a shoulder (934) extending from the radial inner portion thereof such that the recess is capable of retaining liquid when the spindle is inverted.

Paragraph 114. The spindle of Paragraph 112, wherein the major turbulence pocket (512) includes a large opening (926) facing the annular fluid manifold (552) and a small opening (936) defined by a gap between the seal housing (150) and the flinger (660), wherein turbulence within the liquid, impedes flow of the liquid into the small opening (936).

Paragraph 115. The spindle of Paragraph 114, wherein the seal housing (150) further defines a minor turbulence pocket (914) radially inward of the major turbulence pocket (512), the minor turbulence pocket (914) in communication with the small opening (936), the minor turbulence pocket (914) defined by a step-like feature (916) adjacent to the inner diameter of the seal housing (150), wherein the minor turbulence pocket (914) further impedes flow of the liquid through a vertical gap (922) between the seal housing (150) and the shaft (530).

Paragraph 116. The spindle of Paragraph 115, wherein the minor turbulence pocket (914) has a slot wall (925) extending downward from an inner diameter of a flat upper surface (923) of the minor turbulence (914).

Paragraph 117. The spindle of Paragraph 111, wherein the body (120) further comprises a vent (450) between the spindle cavity (440) and the exterior of the body, wherein the vent is sealed with a vent gasket (2054) capable of allowing flow in both directions.

Paragraph 118. The spindle of Paragraph 111, wherein the at least one bearing (508) is lubricated with grease or oil, different from the fluid.

Paragraph 119. The spindle of Paragraph 111, wherein the at least one bearing (508) is a shielded bearing.

Paragraph 120. The spindle of Paragraph 111, wherein the fluid channel system comprises:
  i) the entry port (102) associated with a shank (110);
  ii) a shank channel (416);
  iii) at least one primarily horizontal fluid channel (422) extending from the end of the shank channel;
  iv) at least one primary vertical fluid channel (426) extending from the at least one primary horizontal fluid channel through the body; and
  v) the at least one nozzle (576) in fluid communication with the at least one primary vertical fluid channel.

Paragraph 121. The spindle of Paragraph 111, wherein the spindle comprises a wrench grip (214) positioned between the body (120) and a shank (110) to accept a wrench and assist with mounting the spindle to a chuck.

Paragraph 122. The spindle of Paragraph 111, wherein the at least one bearing (508) includes at least a pair of angular bearings (2308, 2309) contacting one another.

Paragraph 123. The spindle of Paragraph 111, wherein the cover (180) comprises at least one first axial exit opening (588) at the bottom thereof, the at least one first axial exit opening (588) provides an exit for the liquid directed downward by the turbine (570).

Paragraph 124. The spindle of Paragraph 123, wherein the cover (180) comprises at least one second axial exit opening (586) disposed radially outward with respect to the at least one first axial exit opening (588), the at least one second axial exit opening in fluid communication with the annular fluid manifold (552) in order to discharge the liquid deflected upward by the turbine (570).

Paragraph 125. The spindle of Paragraph 124, wherein the cover (180) comprises at least one axial fluid exit channel (982, 984) communicating with the at least one second axial exit opening (586), the axis of the axial fluid exit channel being angled with respect to the shaft (530) such that liquid exiting the at least one second axial exit opening (586) will be directed toward the longitudinal axis (A).

Paragraph 126. The spindle of Paragraph 111, wherein the at least one bearing is a plurality of bearings, and the plurality of bearings are of different types or dimensions.

Paragraph 127. The spindle of Paragraph 111, further comprising a stationary ring (1340) disposed within the seal housing (150), the stationary ring (1340) configured to impinge upon a seal annular gap (574) positioned below the flinger (660).

Paragraph 128. The spindle of the Paragraph 111, wherein the at least one nozzle (576) is formed along the inner diameter of a nozzle ring (977), the nozzle ring (977) is disposed within the cover (180) to define a nozzle fluid manifold (578), wherein the at least one nozzle (576) is angled relative to the radial direction of the shaft (530) in order to impact with maximum force of the fluid on the turbine (570).

Paragraph 129. The spindle of Paragraph 111, wherein the shaft and the flinger are integrally formed.

Paragraph 130. The spindle of Paragraph 111, wherein the shaft (530) comprises a plurality of axially spaced flingers (660, 961).

Paragraph 131. The spindle of Paragraph 111, further comprising a filter mesh (206).

Paragraph 132. The spindle of Paragraph 111, wherein the body (102) comprises:
a) a shell (2120); and
b) a core (2130), the core comprising:
 i) a bearing housing cavity (2142) surrounding the spindle cavity (440); and
 ii) a shank (110); and
 wherein the fluid channel system further comprises:
 i) the entry port (102) associated with the shank (110);
 ii) a shank channel (216);
 iii) at least one primary horizontal fluid channel (422) extending from the end of the shank channel through the bearing housing cavity (2142);
 iv) at least one primary vertical fluid channel (426) in the shell, the at least one primary vertical fluid channel (426) in fluid communication with the at least one horizontal fluid channel through bearing housing cavity; and
 v) the at least one nozzle (576) in fluid communication with the at least one primary vertical fluid channel.

Paragraph 133. The spindle of Paragraph 132, wherein the shell (2120) has a first material having a first density and a first hardness and the core (2130) has a second material having a second density and second hardness, wherein the first density is less than the second density and the first hardness is less than the second hardness.

Paragraph 134. The spindle of Paragraph 111, wherein:
the flinger (660) is a spring flinger (1040), the spring flinger (1040) having a flexible section (1044), the spring flinger attached to the shaft (530) and positioned above the turbine (570); wherein:
when the shaft (530) is idle the flexible section (1044) has a first position relatively close to the shaft such that the flexible section contacts and seals with a portion of the seal housing (150), and
when the shaft is rotating, the centrifugal forces generated by the rotating shaft cause the flexible section (1044) to flex away from the shaft, providing a flinger surface for deflecting the liquid, and removing contact with the seal housing (150).

Paragraph 135. The spindle of Paragraph 111, further comprising:
a flexible flap (1140) mounted within the seal housing (150); wherein:
when pressurized liquid is not present in the spindle, the flexible flap forms a contact seal between the flinger (660) and the seal housing (150) to prevent residual liquid from contaminating the at least one bearing (508), and
when pressurized liquid is present within the spindle, the flexible flap (1140) is deflected away from the flinger (660) to eliminate contact therewith.

Paragraph 136. The spindle of Paragraph 135, wherein the flexible flap (1140) is deflected by pressurized liquid within the annular fluid manifold (552).

Paragraph 137. The spindle of Paragraph 135, wherein the flexible flap (1140A) includes an internal cavity (1147A) in fluid communication with the fluid channel system such that fluid pressure within the fluid channel system causes the flexible flap (1140A) to flex away from the flinger (660).

BRIEF DESCRIPTION OF THE DRAWINGS

FIG. 1A is a top perspective view of a spindle according to embodiments of the present disclosure.

FIG. 1B is a bottom perspective view of the spindle shown in FIG. 1A.

FIG. 2 is an exploded view of the spindle shown in FIGS. 1A and 1B.

FIG. 3A shows a bottom perspective view (and bottom plan view), of the body (and shank) of the spindle from FIGS. 1A and 1B.

FIG. 3B shows a top perspective view of the body (and shank) of the spindle from FIGS. 1A and 1B.

FIG. 3C shows a top perspective view of the body of the spindle from FIGS. 1A and 1B with an alternative shank.

FIG. 6 shows a bottom perspective view of a first embodiment of the internal subsystem of the spindle from FIGS. 1A and 1B.

FIG. 7 shows a cross section of the internal subsystem shown in FIG. 6.

FIG. 9B shows a more detailed view of the non-contact seal of FIG. 9A.

FIG. 11A shows a detailed cross sectional view of a spindle having a contact seal in a first position, according to a second embodiment.

FIG. 11B shows a detailed cross sectional view of a spindle having a contact seal in a second position, according to the second embodiment.

FIG. 13A shows a partial bottom exploded view of the spindle of FIG. 1B according to another embodiment thereof.

FIG. 16A is a cross section of the spindle of FIG. 15 with the control ring in an open position.

FIG. 16B is a cross section of the spindle of FIG. 15 with the control ring in a closed position.

FIG. 20 shows a vent configuration as used in embodiments of the spindle of the present invention.

DETAILED DESCRIPTION OF THE DISCLOSURE

Figure 4A:
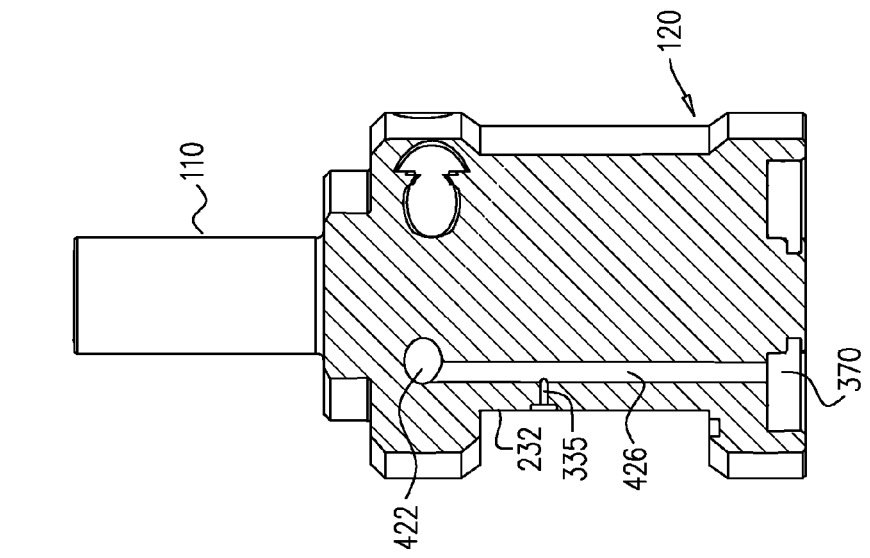
FIGS. 4A, 4B and 4C show cross sections through the body shown in FIG. 3A at planes IVA-IVA, IVB-IVB and IVC-IVC respectively.

Exemplary embodiments of this disclosure are described below and illustrated in the accompanying figures, in which like numerals refer to like parts throughout the several views. The embodiments described provide examples and should not be interpreted as limiting the scope of the invention. Other embodiments, and modifications and improvements of the described embodiments, will occur to those skilled in the art and all such other embodiments, modifications and improvements are within the scope of the present invention. Features from one embodiment or aspect may be combined with features from any other embodiment or aspect in any appropriate combination. For example, any individual or collective features of method aspects or embodiments may be applied to apparatus, product or component aspects or embodiments and vice versa.

Structure Substantially Consistent Among all Embodiments

Turning to FIGS. 1A and 1B, top and bottom perspective views of a high speed spindle (100) according to embodiments of the present disclosure is shown.

The high speed spindle (100) comprises a shank (110) by which the spindle (100) is mounted, typically to an electric spindle or other conventional machine. The shank (110) is connected to a high speed spindle body (120), which is further connected to a seal housing (150) and a cover (180). The high speed spindle (100) shown in FIGS. 1A and 1B includes an optional sensor module (130). In one embodiment, the sensor module is wireless.

In an embodiment the high speed spindle (100) is connected to the machine only at the shank (110). High pressure fluid is communicated to the high speed spindle (100), through a fluid entry port (102) that is at the shank's distal end or at the distal end of shank extensions (101).

In one embodiment, the high speed spindle body (120) does not rotate when the high speed spindle (100) is mounted to a machine; particularly the body (120) does not rotate when the high speed spindle (100) is in use, performing material removal, but can rotate during setup and/or before or after material removing operations.

In another embodiment, the spindle (100) is sufficiently balanced such that the high speed spindle body (120) may be rotated by an electric spindle at rates exceeding 500 RPM while the machine in performing material removal processes and during setup.

In an embodiment the shank (110) is held in a machine approximately on the spindle axis of rotation, corresponding to the longitudinal axis A of the high speed spindle (100). The longitudinal axis A is used to define relative positions of features within the spindle (100). The shank (110) is at the top or upper end, while the cover (180) is at the bottom or lower end. The longitudinal axis A, used interchangeably with the spindle axis or the shaft axis is also used to define the directional terms used herein. The terms horizontal and lateral are used herein or refer to elements or features that lie or extend generally perpendicular to the longitudinal axis. The terms vertical and axial are used herein to refer to elements or features that lie or extend generally parallel to the longitudinal axis.

In another embodiment the shank (110) is held in a machine at a vertical offset to the spindle axis of rotation. In another embodiment the shank (110) is held in a machine at an angle to the spindle axis of rotation. In another embodiment the shank (110) is held in a machine at a 90 degree angle to the spindle axis of rotation.

In an embodiment, the spindle (100) is shaped and sized to fit in a machining system Automatic Tool Changer (ATC). The ATC includes a robotic arm to extract the spindle (100) from a tool slot and position it in the machine as well as placing tools released from the machine in the ATC tool slots.

The ATC typically has slots for storing various tools. Different ATC's systems have varying slot configurations and sizes. In some embodiments, slots are designed to hold tools ranging in diameter from 100 to 30 mm.

The diameter of the high speed spindle body (120) can be less than 100 mm, less than 90 mm, less than 80 mm, less than 70 mm, less than 60 mm, or less than 50 mm. The maximum diameter of the high speed spindle body (120), including the sensor module (130), may be less than 120 mm, less than 100 mm, less than 90 mm, less than 80 mm, less than 70 mm, or even less than 60 mm.

Turning to FIG. 2, an exploded view of the high speed spindle (100) is shown. The high speed spindle (100) can include a filtration unit comprising a filter mesh (206) and a filtration unit nut (204) that secures the filtration system to the shank (110).

An internal subsystem (240) is assembled with the seal housing (150) to be inserted into the high speed spindle body (120) and secured to the body (120) with first screws (252) that connect the seal housing (150) with the high speed spindle body (120).

The cover (180), with gasket (248), is secured to the seal housing (150) with second screws (282). A cutting tool (not shown) is connected to a shaft (not shown) with a collet (290) which is connected to the shaft with a collet nut (292).

Securing or releasing a cutting tool from the spindle (100) can be done with a wrench that secures the collet nut (292) connecting the cutting tool and spindle (100). In an embodiment, the high speed spindle (100) connects to the machine in similar fashion. The wrench may be a spanner wrench or an ER wrench, wherein the wrench will include at least one pin, flat, tab or similar feature, that coincide with the slots or other features in the respective nut.

The high speed spindle may include a wrench grip (214) between the shank (110) and the high speed spindle body (120). The wrench grip (214) is provided to facilitate installation and removal of the fluid powered spindle (100) from a chuck of an electric spindle. The wrench grip (214) may be circular, hexagonal, or otherwise include flat portions for mating with a wrench. The wrench grip (214) is a larger diameter section at the bottom portion of the shank (110). The wrench grip (214) diameter is larger than the shank (110) diameter and smaller than the high speed spindle body (120) diameter. The wrench grip (214) height is larger than the thickness of a typical wrench including the wrench pin or tab that fits in a slotted nut.

A seal slot (218), on the horizontal ring surface of the wrench grip (214) seals the contacting surfaces of the high speed spindle (100) and the electric spindle in which it is held. In an embodiment, the seal slot (218) consists of at least one slot for an O-ring. In an embodiment, the seal slot is flat such that a flat ring seal or shaped seal can be positioned therein.

Further, the sensor module (130) is mounted at a mounting location (232). In an embodiment, the spindle may have a plurality of sensor modules (130) mounted to a plurality of mounting locations (232) around the body (120).

Turning to FIGS. 3A-3C, FIG. 3A shows a bottom perspective view (and bottom plan view), of the body (120) and shank 110 of the high speed spindle. FIG. 3B shows a top perspective view thereof. FIG. 3C shows a top perspective view of the body (120) with an additional cone shank (312) having a larger diameter that integrates with the wrench grip 214.

As seen in FIGS. 3A-3C, the high speed spindle body (120) may be integrated with the shank (110) by which the high speed spindle is held. The body (120) includes at least one mounting location (232) for a sensor module (130). The mounting location (232) may include a sensing aperture (334) in the high speed spindle body. The sensing aperture (334) provides a path for the sensor module sensors to sense elements within the body. In one embodiment, the sensing aperture (334) provides a path for the sensor module sensors to connect, without contact, with elements within the body. For example, aperture (334) provides a line of sight path for the sensor module sensors to sense elements within the body, or the sensing aperture (334) may be designed with materials that are optically opaque or translucent, but sufficiently transparent to specific frequencies of the electromagnetic spectrum for the operation of electromagnetic sensors.

A fluid aperture (335) in the mounting location (232) for a sensor module (130) may be fluidly connected to a high pressure fluid channel system within the high speed spindle body (120). The fluid aperture (335) provides a fluidic path for sensor module sensors to sense fluid system properties of the high pressure fluid system. Fluid system properties such as fluid pressure, fluid velocity and fluid viscosity.

Mounting threads (336) and one or more mounting slots (338) can be associated with the mounting location (232) with which the sensor module (130) can be secured to the high speed spindle body (120).

At the bottom end (398) of the high speed spindle body (120) there is a round slot that forms a first fluid manifold (370) when the high speed spindle body (120) is connected with the seal housing (150).

The bottom plan view of the high speed spindle body (120) shows bottom openings (354) for primary vertical fluid channels that fluidly communicate with the first fluid manifold (370). Threaded holes (352) are used to connect the seal housing (150) to the body (120).

An access opening (324) is provided in the high speed spindle body (120) from which at least one primary horizontal fluid channel is machined. The access opening (324) may include screw threads that are used to secure a plug or screw (not shown) that seals the opening.

Figure 4B:
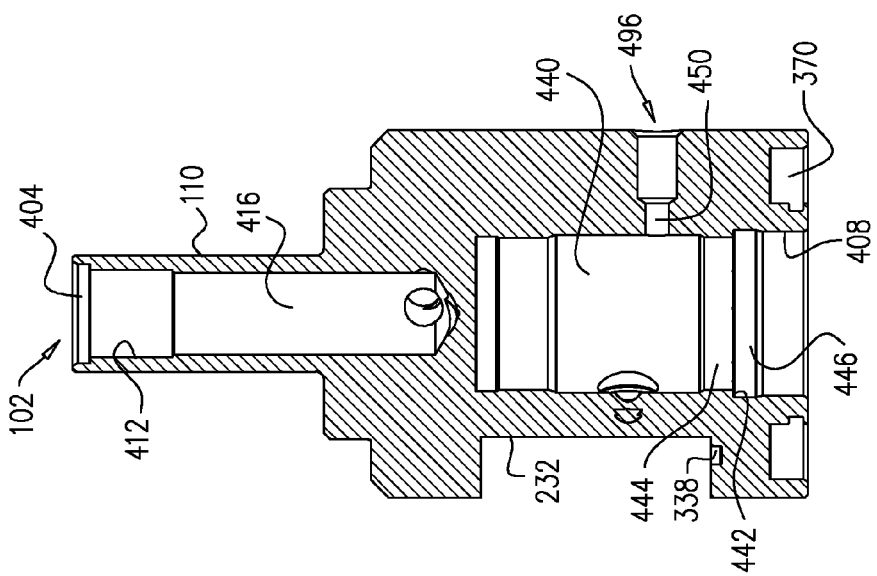
Figure 4C:
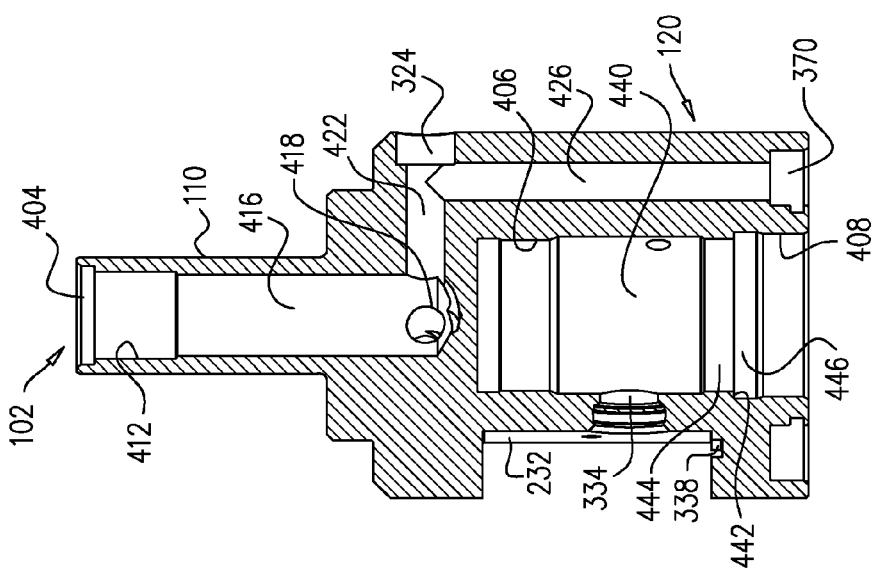

Turning to FIGS. 4A-4C, FIG. 4A is cross section IVA-IVA of the high speed spindle body, as seen in FIG. 3A. The shank thread (412) near the shank end (404) of the high speed spindle body is used to connect components such as components of a filtration unit or shank extenders.

FIG. 4A shows the fluid channel system within the high speed spindle body. The fluid channel system consists of the shank channel (416) within the shank (110) that fluidly connects the entry port (102) with the fluid channel junction (418). The fluid channel junction (418) fluidly connects with at least one primarily horizontal fluid channel (422). In the exemplified embodiment there are three primary horizontal fluid channels, spaced 120 degrees apart. The at least one primarily horizontal fluid channel (422) intersects with a respective primary vertical fluid channel (426), that spans the length of the high speed spindle body (120). In the exemplified embodiment, the primary vertical fluid channel (426) ends at the first fluid manifold (370).

In an embodiment the fluid channel system includes a pressure relief mechanism, such as a valve (not shown). In an embodiment the pressure relief mechanism is connected to the fluid channel system at the at least one access opening (324). In an embodiment the pressure relief mechanism is located in the high speed spindle cover (180).

Figure 5:
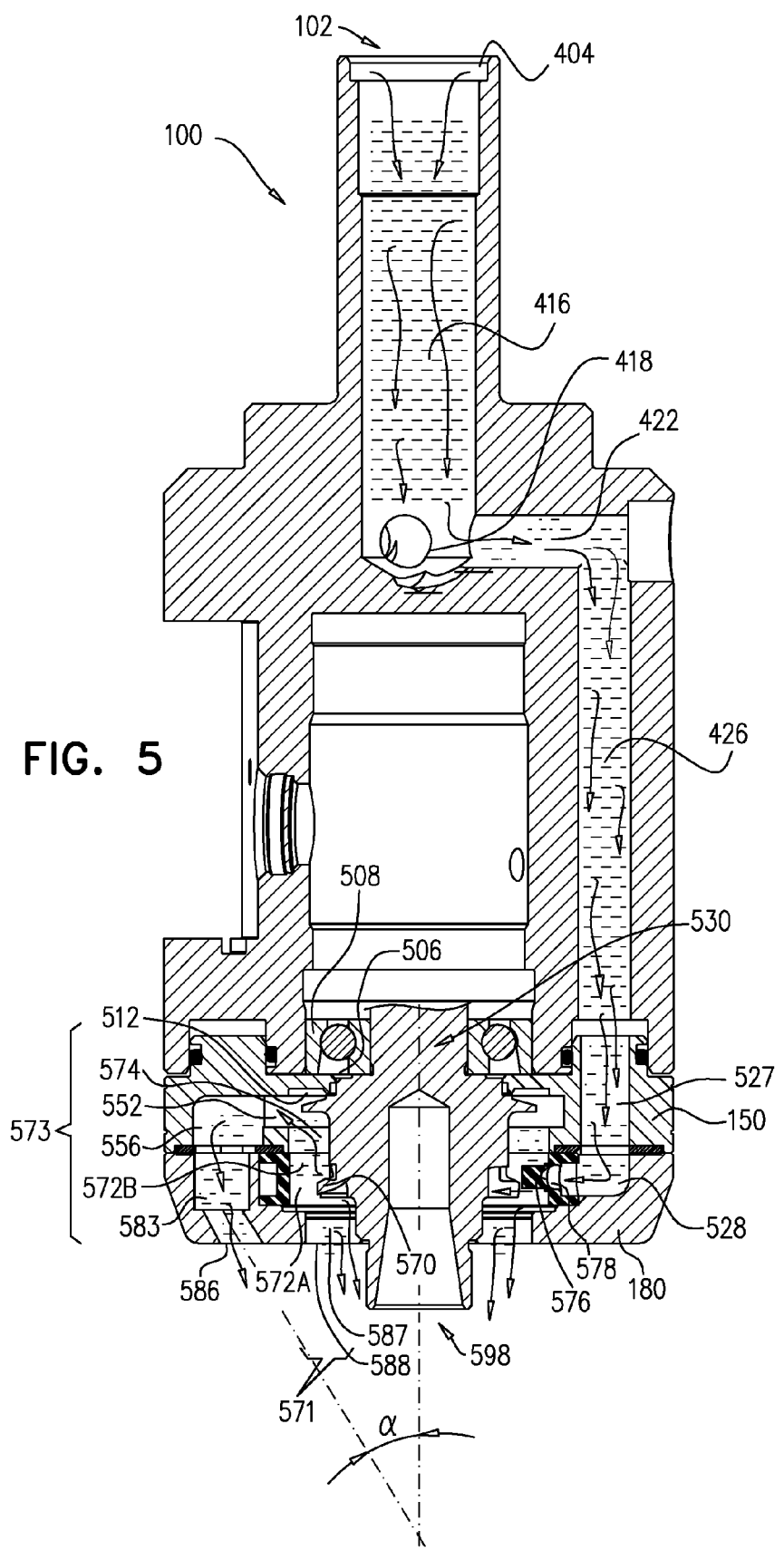
FIG. 5 shows a partial cross section of the spindle shown in FIGS. 1A and 1B, schematically showing the fluid flow therein.

The internal subsystem (240) is mounted with at least one bearing within the high speed spindle cavity (440). The external ring of the at least one bearing is positioned on a portion of the cavity surface (e.g. first bearing cavity-mounting surface 406 and second bearing cavity-mounting surface 408) whose properties and surface finish are suitable for mounting bearing ring's to provide a tight fit and high accuracy during high speed rotation and high speed machining as best seen in FIG. 5.

In an embodiment, the surface finish parameter, Ra, at the bearing mounting surfaces (406, 408) is less than 0.2 micron meter, i.e. N4 per ISO 1302. In an embodiment, the surface finish parameter, Ra, at the bearing mounting surfaces (406, 408) is less than 0.4 micron meter, i.e. N5 per ISO 1302. In an embodiment, the surface finish parameter, Ra, at the bearing mounting surfaces (406, 408) is less than 0.8 micron meter, i.e. N6 per ISO 1302. In an embodiment, the surface finish parameter, Ra, at the bearing mounting surfaces (406, 408) is less than 1.6 micron meter, i.e. N7 per ISO 1302.

In an embodiment, the concentricity tolerance at the bearing mounting surfaces (406, 408) is less than 2 micron meter. In an embodiment, the concentricity tolerance at the bearing mounting surfaces (406, 408) is less than 3 micron meter. In an embodiment, the concentricity tolerance at the bearing mounting surfaces (406, 408) is less than 4 micron meter. In an embodiment, the concentricity tolerance at the bearing mounting surfaces (406, 408) is less than 5 micron meter.

In an embodiment, the cylinder tolerance at the bearing mounting surfaces (406, 408) is less than 2 micron meter. In an embodiment, the cylinder tolerance at the bearing mounting surfaces (406, 408) is less than 3 micron meter. In an embodiment, the cylinder tolerance at the bearing mounting surfaces (406, 408) is less than 4 micron meter.

In the exemplified embodiment, there are two bearings that are mounted on bearing mounting surfaces: the first bearing cavity-mounting surface (406) and the second bearing cavity-mounting surface (408).

In the exemplified embodiment, there is a spacer shoulder (442) for positioning the bearing spacer (610, FIG. 6) above the second bearing cavity-mounting surface (408). The shoulder consists of two sections: the larger-diameter section (446) and the smaller-diameter section (444). Wherein the diameter of the larger-diameter section (446) is larger than the diameter of the smaller-diameter section (444).

Also shown is sensor module mounting location (232). In the exemplified embodiment, there is a mounting slot (338) with which the sensor module can be positioned and secured to the high speed spindle body.

The fluid used to rotate the high speed spindle turbine is communicated to the turbine through a channel and nozzle system that starts at the shank channel (416) and spans the high speed spindle body (120) through at least one primarily horizontal fluid channel (422), through at least one primary vertical fluid channel (426) and ends at the first fluid manifold (370).

FIG. 4B is cross section through plane IVB-IVB shown in FIG. 3A of the high speed spindle body (120). The vent (450) in the spindle body fluidly connects the high speed spindle cavity (440) with the exterior (496) of the high speed spindle.

Although shown in the cross section as a single material, the body (120) and the shank (110) may be formed from multiple parts that are mechanically connected. Further, the body (120) may include a cone according to the ER standard (not shown). Fluid may enter the high speed spindle via external channels in the cone, that communicate with openings in the cone envelop that are the start of a channel and nozzle system that spans the spindle body and ends in proximity to turbine blades.

FIG. 4C is cross section through plane IVC-IVC as seen in FIG. 3A. FIG. 4C shows a portion of the fluid channel system within the high speed spindle body. Specifically, FIG. 4C shows at least one primarily horizontal fluid channel (422) that intersects with a primary vertical fluid channel (426) that spans the length of the high speed spindle body (120). In the exemplified embodiment, the primary vertical fluid channel (426) ends at the first fluid manifold (370). In the exemplified embodiment, there is a fluid aperture (335) fluidly connecting the primary vertical fluid channel (426) with the sensor module mounting location (232). In an embodiment, the sensor module includes a fluid pressure sensor that measures high pressure fluid pressure. Monitoring the fluid pressure and/or velocity can provide indications of the system stability. In an embodiment, the measurements are used to close a control loop on the high speed spindle.

Fluid Flow within a Bottom-Discharge Spindle

Turning to FIG. 5, the fluid flow within the high speed spindle (100). In the preferred embodiment, the fluid is a liquid. Fluid enters the high speed spindle through entry port (102) in shank end (404). The fluid flows through the shank channel (416) to fluid channel junction (418). From the fluid channel junction (418) the fluid flows to at least one primarily horizontal fluid channel (422) and on to at least one primary vertical fluid channel (426) that spans the length of the high speed spindle body.

The fluid continues through secondary vertical fluid channel (527) in the seal housing (150) and through inlet channel (528) in the cover (180).

The fluid enters the seal housing (150) through secondary vertical fluid channel (527), continues to inlet channel (528) in the cover (180) to the nozzle fluid manifold (578) and to the at least one nozzle (576). The fluid exiting the at least one nozzle (576) is directed towards turbine (570) that causes a shaft (530) to rotate at high speed.

A portion of the fluid impacting the turbine (570) is diverted from the turbine to the central fluid exit (571) which is in proximity to the shaft (530) and towards the shaft tool end (598). In the exemplified embodiment, the central fluid exit (571) includes lower annular gap (572A), bottom annular cavity (587) and first axial exit opening (588) in the cover.

The remaining fluid is diverted from the turbine, to the second fluid exit (573). In the exemplified embodiment, the second fluid exit (573) includes upper annular gap (572B) between the rotating turbine and a nozzle ring; and a seal annular gap (574) under a rotating flinger, and second annular fluid manifold (552) both defined within in the seal housing (150).

In the exemplified embodiment, the second fluid exit (573) also includes a stationary fluid exit channel (556) which is fluidly connected to the cover exit channel (583) in the cover (180) and to at least one second axial exit opening (586). In the exemplified embodiment, fluid exiting the second fluid exit (573) is directed towards the shaft tool end (598). The fluid exiting the second fluid exit (573) is directed towards the shaft tool end (598) at an angle alpha. In one embodiment, alpha is greater than 10 degrees, in another embodiment alpha is greater than 20 degrees.

Due to fluid pressure fluctuations in the turbine (570) and lower and upper annular gaps (572A, 572B), a portion of the fluid in the seal annular gap (574) under the rotating flinger may continue above the flinger. In one embodiment, a major turbulence pocket (512) is created as a recess within the seal housing (150) above the second annular fluid manifold (552).

The objective of the sealing system is to prevent fluid exiting the turbine (570) from flowing to a gap (506) below a second bearing (508).

In some cases, the high speed spindle (100) is stored in an ATC, or other storage, after it has been used, and the storage position is vertical, wherein the cutting tool is facing up or horizontal or at any other angle. In such cases there is a concern that residual fluid that remains on the cutting tool, on the turbine (570) or in the seal housing (150), will traverse the non-contact seal and flow toward the second bearing (508). The major turbulence pocket (512) is configured to retain a portion, or all, of the residual fluid in a recess (924) when the spindle is in an inverted position.

Note that the direction of rotation of the shaft (530) is determined by the shape of the fins on turbine (570), those fins being symmetrical or non-symmetrical, and the nozzle direction. In one embodiment the turbine fins and nozzles are formed to rotate the shaft in a counter clock wise (CCW) direction. In another embodiment the turbine fins and nozzles are formed to rotate the shaft in a clock wise (CW) direction.

Internal Subsystem

Turning to FIG. 6, FIG. 6 shows a bottom perspective view of a first embodiment of the internal subsystem (240) and seal housing (150) of the spindle from FIGS. 1A and 1B.

The internal subsystem (240) includes: a shaft (530), a first bearing (606); a second bearing (not visible), a bearing spacer (610) that is positioned next to the first bearing (606) outer ring and second bearing out ring (not shown); a flinger (660) and the turbine (570A, where "A" is added to designate an alternative embodiment, in this case the turbine being separate as opposed to integral) attached to the shaft (530). The seal housing (150) is disposed around at least a portion of the internal subsystem (240) to provide a non-contact seal helping to impede fluid from reaching the second bearing (508, see FIG. 5).

In the bottom surface (651) of seal housing there are: counter bores (656) for bolts used to connect the internal subsystem (240) and the seal housing (150) to the spindle body (120), vertical fluid channel's bottom openings (354), threaded holes (352) for connecting the spindle cover (180) to the seal housing (150) and seal housing fluid exit holes (686), external shoulder (622) and internal shoulder (623) that bench a flat gasket (not shown) that is inserted between the bottom surface (651) of seal housing and the cover. Wherein the bottom surface (651) of seal housing is the surface closest to the cover (180).

The bearing spacer (610) can include a bearing spacer opening (612). In conjunction with the sensing aperture (334), the bearing spacer opening (612) can also provide a line of sight path for the sensor module sensors to sense rotation, or the bearing spacer opening (612) may be designed with materials that are optically opaque or translucent, but sufficiently transparent to specific frequencies of the electromagnetic spectrum for the operation of electromagnetic sensors.

Turning to FIG. 7, a cross-section through axis VII-VII of FIG. 6 is shown. The internal subsystem (240) includes: a shaft (530); first bearing (606) and second bearing (508); a bearing spacer (610) that is positioned next to the first and second bearing outer rings (716, 718); a flinger (660), at least one turbine (570A) attached to the shaft (530), collet mounting surface (794) and a thread (795) for the collet nut on the distal lower end of the shaft (530).

The shaft is symmetrical along its length axis and dynamically balanced for high speed rotation with minimal vibration.

In an embodiment, the bearings (606, 508) are angular contact bearings. In other embodiments the bearings (606, 508) are contact bearings such as deep groove, roller or needle. In other embodiments, the bearings (606, 508) have no rolling element, such as slip ring bearings, friction bearings, magnetic bearing, air or hydraulic bearings.

In some embodiments, in order to avoid excitation of bearings natural frequencies, the bearings (606, 508) are not of identical design, for example different diameters, widths and/or types.

In some embodiments, the bearings are integrated with the shaft such that the bearing inner race is integral to the shaft (not shown) and the bearing is assembled on the shaft. Integrated bearings enable smaller diameter and lighter weight systems.

In an example embodiment, the first and second bearings (606, 508) are mounted on the shaft (530) with an axial preload. The bearings may be preloaded during assembly with their respective first and second bearing inner rings (717, 719) glued to the shaft (530). The bearing preload can be defined by two factors: the dimensions and properties of the at least one bearing spacer (610) that is mounted between the bearing outer rings (716, 718); and the assembly process in which the bearings are loaded while the glue is setting. In an embodiment, the first bearing inner ring (717) is mounted against a shoulder or similar feature in the shaft, first bearing mounting shoulder (733). In an embodiment, the second bearing inner ring (719) is mounted against a shoulder or similar feature in the shaft, second bearing mounting shoulder (738). In an embodiment, the system is preloaded with a shaft top screw (704) that is threaded into the shaft and tightened against the first bearing inner ring (717). The shaft top screw (704) that is threaded into the shaft prevents rotation of the first bearing inner ring (717) such that the shaft top screw (704) is threaded into the shaft is tightened and locked such that it provides preload to the bearings.

The turbine (570A) with at least one turbine fin is positioned next to the non-contact seal housing, toward the shaft tool end (598). In an embodiment, a turbine ring (774) that supports at least one turbine fin is mounted on the shaft. This design enables using different types of turbines (570A) on the same shaft design.

In another embodiment the turbine (570) with at least one turbine fin is integrated with the shaft (530). That is, the shaft and turbine are machined together from one piece. Integrating the shaft and turbine simplifies assembly and provides precise axial symmetry.

In an embodiment, there is a shaft lock hole (734) in the shaft. The shaft lock hole (734) is used to secure the shaft with an external tool (not shown), when the collet is being tightened.

The external tool is inserted through a corresponding shaft lock hole in the high speed spindle body. In an embodiment, the corresponding shaft lock hole in the high speed spindle body is the vent (450) in the spindle body.

The bearing spacer (610) is designed to facilitate positioning of the at least one bearing and support the preload required. In the exemplified embodiment, the bearing spacer is positioned between the first bearing outer ring (716) and the second bearing outer ring (718). In this configuration, the bearing spacer (610) does not rotate with the shaft (530).

In an embodiment, the bearing spacer (610) will include a feature that will position it relative to the high speed body spindle (not shown). In the exemplified embodiment, the bearing spacer (610) includes a positioning shoulder (711) that is benched against a corresponding spacer shoulder (442) in the high speed spindle cavity (440).

As discussed above with respect to FIG. 6, a bearing spacer opening (612) can be provided in bearing spacer (610).

In an embodiment, the shaft includes a rotational position reference (714) by which the shafts rotation speed can be determined. The rotational position reference (714) is designed such that it does not affect the axial symmetry and balancing of the shaft (530). In one example, the rotational position reference is one or more through holes in the shaft along the shaft's radial axis. In another example, the position reference is defined by multiple holes that do not traverse the shaft diameter from side to side. In other embodiments the rotational position reference is a flat, a slot, a fin like protrusion, a cutout, a pin or a tab that extrudes from the shaft or placed within cavities within the shaft. In other embodiments, the reference is defined by a local change in shaft properties such as color, surface finish, electrical or magnetic properties. In other embodiments, the reference is defined by adding a ring or cover on the shaft, wherein the ring or cover has local features that can be identified by a sensor. In an embodiment, a magnet is placed in a through hole. In an embodiment, a material that is different than the shaft material is placed in a through, or non-through, hole.

In an embodiment, at least one bearing inner ring (717, 719) is mounted on the bearing shaft-mounting surface (732, 736). In the exemplified embodiment there are two shaft bearing mounting surfaces: the first bearing shaft-mounting surface (732) and the second bearing shaft-mounting surface (736). Both surfaces have similar surface properties as detailed for bearing mounting surfaces (406, 408) within the high speed spindle cavity (440).

Figure 8A:
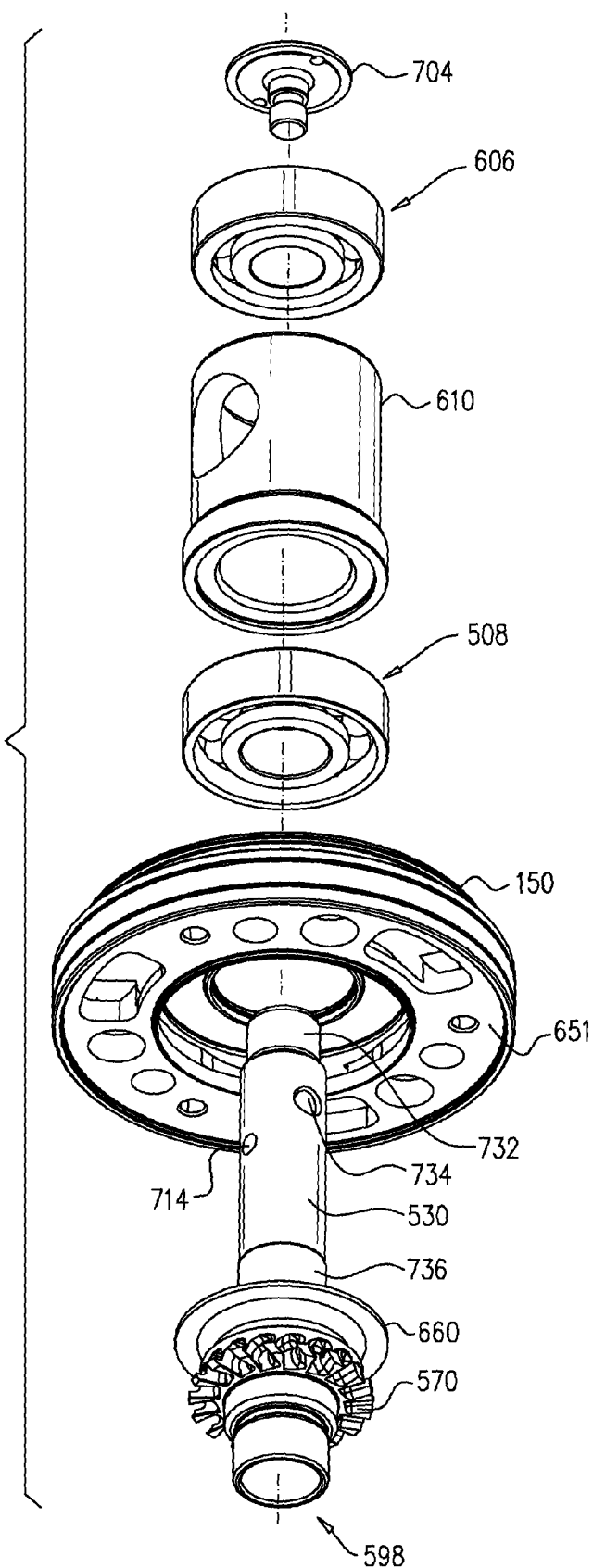
FIG. 8A shows an exploded view of the internal subsystem shown in FIGS. 6 and 7.

Turning to FIG. 8A, an exploded view of FIG. 6 is shown. In the exemplary embodiment the shaft (530) is integrated with the flinger (660) and turbine (570). The shaft is machined to include first bearing shaft-mounting surface (732) and second bearing shaft-mounting surface (736).

The seal housing (150) is positioned on the shaft, with the bottom surface (651) facing towards the shaft tool end (598). Once the seal housing (150) is in place, second bearing (508), bearing spacer (610) and first bearing (606) are assembled on the shaft. Closing the assembly is shaft top screw (704).

Figure 8B:
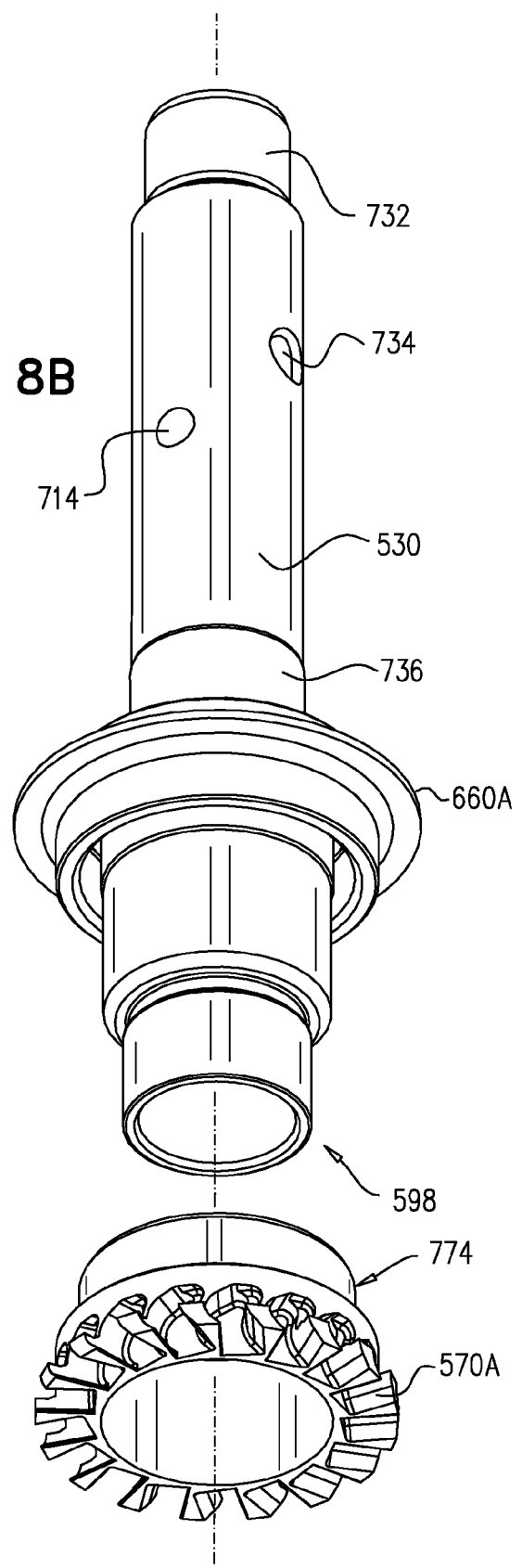
FIG. 8B shows a detailed exploded view of the shaft separate from the turbine.

Turning to FIG. 8B, the at least one turbine (570A) is connected to a turbine ring (774) which is assembled and connected on the shaft from the shaft tool end (598). The advantage of using a turbine ring is that it provides flexibility of assembling different turbine designs on to the same shaft and internal subsystems. In an embodiment, the flinger (660A) is mounted on a ring which is assembled and connected on the shaft from the shaft tool end (598). In an embodiment, the flinger is mounted on an elongated turbine ring (not shown) which is assembled and connected on the shaft from the shaft tool end (598).

The Non-Contact Seal (Shown in an Axial Discharge Spindle)

A non-contact seal is primarily provided by the combination of the seal housing (150) and the rotating flinger (660). The rotating flinger is attached to (660A) or integral with (660) the shaft (530), and impedes flow of fluid toward the second bearing (508).

The non-contact seal design is such that it will not create contact friction when the system is rotating. Similarly, there will be no contact friction wear and tear. In an embodiment, the non-contact seal is compact in length. In an embodiment, the length is less than twice the maximum shaft diameter. In another embodiment the length is less than the maximum shaft diameter. In another embodiment the length is less than one-half the maximum shaft diameter.

The seal system is comprised of a non-contact seal, and may or may not further include at least one contact seal. The seal system length compact. In an embodiment, the length is less than twice the maximum shaft diameter. In another embodiment the length is less than the maximum shaft diameter. In another embodiment the length is less than one-half the maximum shaft diameter.

If a contact seal is present, the contact seal maintains contact between the stationary elements and the rotating elements of the spindle (100) when the spindle is at rest or at low rotation speeds. Furthermore, when the spindle is at rest or at low rotation speeds, the contact seal maintains contact with both the stationary and rotation elements regardless of system orientation.

However, when the spindle is at high rotation speeds the contact seal maintains contact with only one of the stationary elements or the rotating elements, depending on contact seal type. Because the contact seal maintains contact with only the stationary elements or the rotating elements during high speed rotation, there is little wear and tear on the contact seal or to the components it comes in contact with. Similarly, there is a minimal amount of debris due to contact friction.

The non-contact seal is a friction free system wherein there is no friction between solid parts. The only friction in the system is caused by fluid and/or debris that is rotated between the stationary and rotating elements.

Figure 9A:
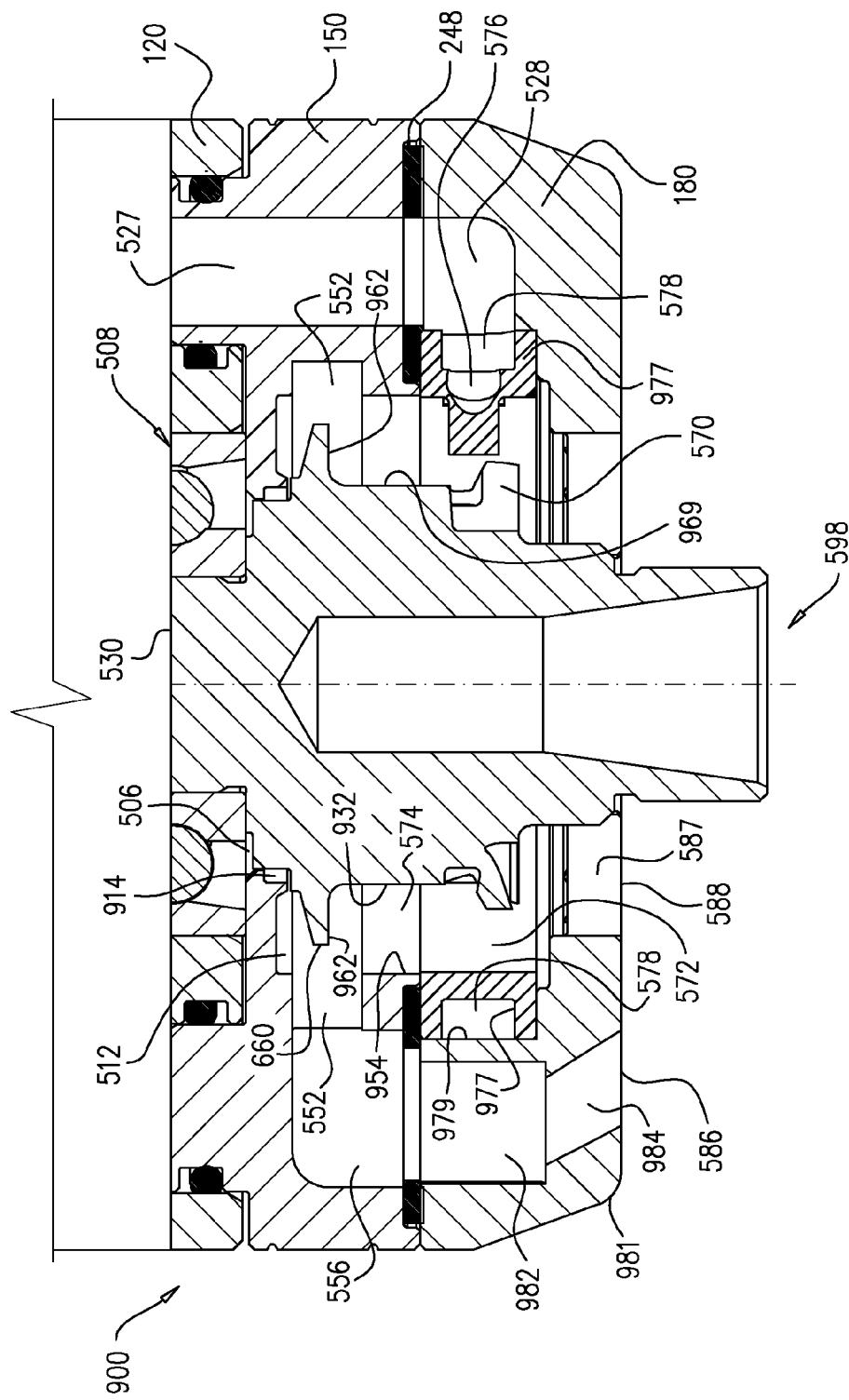
FIG. 9A shows a detailed view of the non-contact seal and cover portions of FIG. 5.

Turning to FIG. 9A, a partial cross section of the spindle from FIG. 1A is shown. The illustrated portion generally represents a non-contact seal (900). The non-contact seal (900) is designed to prevent fluid exiting the turbine (570) to flow to gap (506) below second bearing (508).

The non-contact seal (900) is comprised of two elements: a rotating element, particularly flinger (660), which is part of the shaft or connected to it, and a stationary element, particularly seal housing (150), secured to the high speed spindle body (120). In an embodiment (see FIGS. 13A and 13B), the stationary element is comprised of a first stationary element (seal housing 150) that is secured to the high speed spindle body (120) and a second stationary element (stationary ring 1340) that is connected to the seal housing (150).

The non-contact seal (900) is located between the second bearing (508) which is mounted on the shaft (530) and turbine (570). High pressure fluid enters the non-contact seal (900) through secondary vertical fluid channel (527) in the seal housing (150) and continues to inlet channel (528) in the cover (180), to the annular nozzle fluid manifold (578) and to the at least one nozzle (576)

In the exemplified embodiment, the nozzle fluid manifold (578) is defined by the nozzle ring (977) and the cover inner surface (979) of the cover (180).

The non-contact seal (900) includes the seal housing (150) which at least partially defines the second annular fluid manifold (552), and the stationary fluid exit channel (556). The stationary fluid exit channel (556) fluidly communicates with the axial fluid exit channels, both section one (982) and section two (984) in the cover (180). The seal housing (150) also at least partially defines the seal annular gap (574) under the rotating flinger (660) that fluidly communicates with upper cover annular gap (572) and bottom annular cavity (587). The non-contact seal (900) also includes the rotating flinger (660).

The seal housing (150) is connected on one side to the high speed spindle body (120) and on the other side to the cover (180). A gasket (248) between the seal housing (150) and the cover (180) provides a seal so that high-pressure fluid, flowing in channels that span both parts, does not leak.

The annular gap sections between the rotating components and the stationary components, through which, fluid flows, include: the upper cover annular gap (572) between the turbine and the nozzle ring, and the seal annular gap (574) under the rotating flinger (660).

The fluid exits through the cover (180) via the first axial exit opening (588) near the shaft (530) and through the second axial exit opening (586) which exits the cover (180) closer to the cover radial perimeter (981).

High pressure fluid flowing through the at least one nozzle (576) and directed at the at least one turbine (570) causes the turbine to rotate at high speed. A portion of the fluid impacting the turbine is diverted from the turbine towards the shaft tool end (598), i.e. the bottom of the spindle (100), into bottom annular cavity (587) and through first axial exit opening (588).

Due to the high centrifugal forces, the remaining fluid is diverted from the turbine, into the upper cover annular gap (572) between the rotating turbine and nozzle ring. From there, the fluid flows into the seal annular gap (574) under the rotating flinger (660).

The seal annular gap (574) under the rotating flinger is formed between a shaft first section (932), above the turbine area (969) and the seal housing inner surface (954). The seal annular gap (574) under the rotating flinger is fluidly connected to the second annular fluid manifold (552) in the seal housing (150).

From the seal annular gap (574), most of the fluid will flow toward the rotating flinger lower surface (962) and will be diverted towards the stationary fluid exit channel (556) which is fluidly connected to the second annular fluid manifold (552) on one side and further to the axial fluid exit channels in the cover (180), particularly axial fluid exit channel section one (982) which is fluidly connected to axial fluid exit channel section two (984). From axial fluid exit channel section two (984), the fluid exits the high speed spindle through at least one second axial exit opening (586).

As best seen in FIG. 9B, a portion of the fluid in the seal annular gap (574) under the rotating flinger that flows toward the rotating flinger lower surface (962), continues past the flinger edge surface (964) and above the flinger upper surface (966).

The flow of fluid above the flinger upper surface (966) is impeded primarily by two elements of the non-contact seal.

The first element is the major turbulence pocket (512) defined primarily by an annular recess (924) in the seal housing (150) and the rotating flinger upper surface (966). The major turbulence pocket (512) has two openings, a large opening (926) facing the second annular fluid manifold (552) from which fluid flows in to the major turbulence pocket and a small opening (936). A slot shoulder (934) forms the radially inner wall of the annular recess (924).

The relative motion between recess (924) in the seal housing (150) and the rotating flinger upper surface (966) creates fluid turbulence. Additional turbulence may be created due to the pocket shape. Most of the fluid entering the major turbulence pocket (512) from the large opening (926), flows towards recess (924). Most of the fluid cannot continue through the small opening (936) because its cross section is much smaller, the fluid flow is deflected toward the flinger upper surface (966) resulting in additional turbulence. The fluid turbulence imparted by the separate elements collectively impede the flow of fluid toward the small opening (936).

Fluid that does pass the major turbulence pocket (512) reaches the small opening (936) between the seal housing (150) and the shaft (530), in the exemplary, embodiment, between a slot shoulder (934) and a rotating ledge (938) above the rotating flinger (660).

The second element is the minor turbulence pocket (914) defined by a step-like feature (916) on the inner diameter of the seal housing (150) and the opposing shaft section (918). In an embodiment, more than two turbulence pockets may be used. For example three or more turbulence pockets can be arranged concentrically. In other example plural minor turbulence pockets (914) can be stacked along the axial direction. The use of more than two turbulence pockets may increase seal efficacy, but the tradeoff of an increased number of turbulence pockets is space, fluid friction and manufacturing costs.

The flow pattern of fluid entering the minor turbulence pocket (914) will be turbulent. The relative motion between step-like feature (916) and the opposing shaft section (918) creates fluid turbulence. The fluid turbulence impedes the flow of fluid. Centrifugal forces acting on the fluid within the minor turbulence pocket (914) will concentrate the fluid on the larger diameter portion of the minor turbulence pocket (914), towards the seal housing (150) and away from the vertical gap (922) between the seal housing (150) and the shaft (530).

In order for the shaft to rotate without contact, there is a small gap between the seal housing (150) and the shaft (530) that is closest to the second bearings (508). In the exemplary embodiment, the gap is the vertical gap (922) between the seal housing (150) and the shaft (530).

Figure 9C:
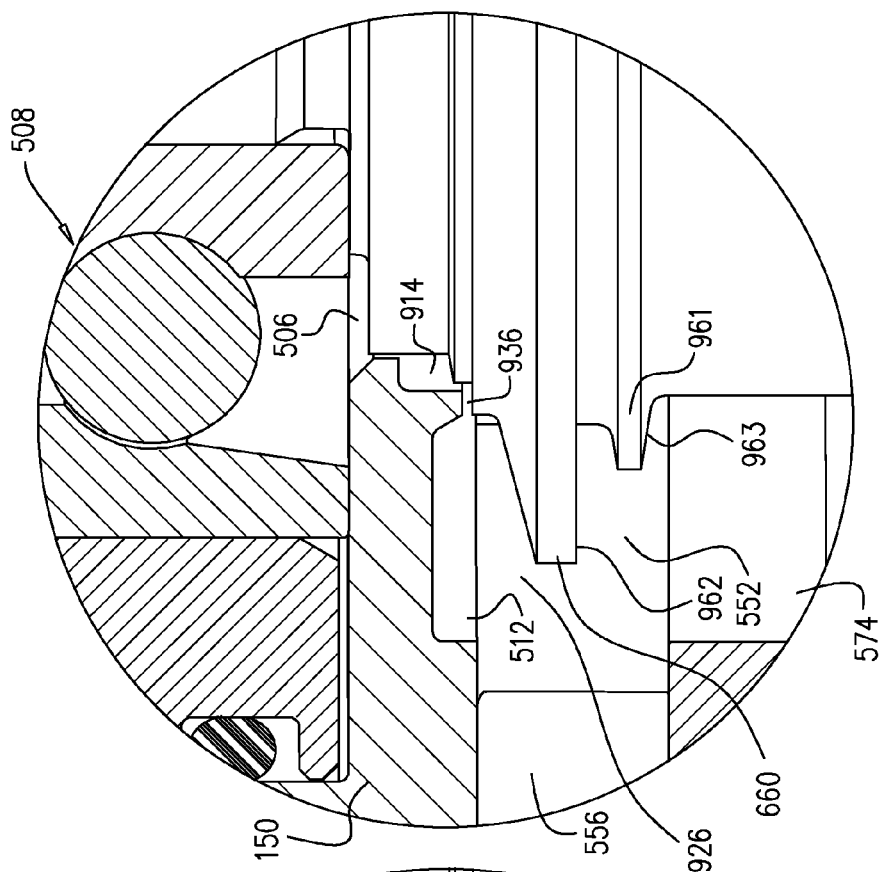
FIG. 9C shows the non-contact seal of FIG. 9B according to a second embodiment.

Referring to FIG. 9C, in this embodiment, the minor turbulence pocket (914) is further defined as a slot in the seal housing (150) having a flat upper surface (923) a slot wall (925) on the inner diameter of the slot. In the above configuration, the length of the vertical gap (922A) increases, while the gap width remains the same.

Figure 9D:
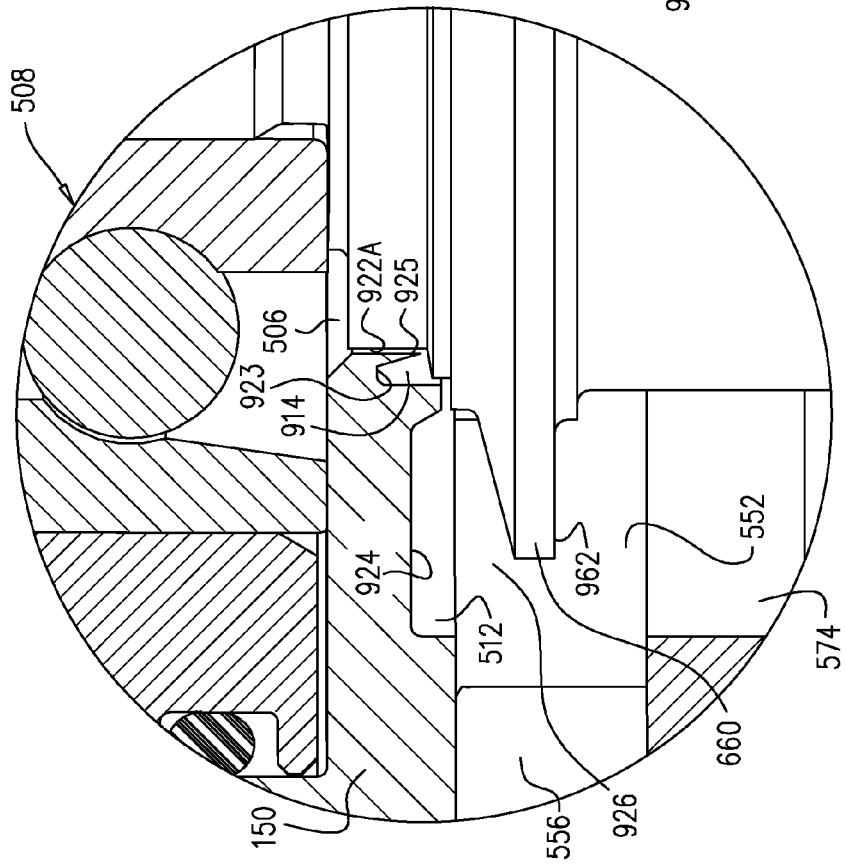
FIG. 9D shows the non-contact of FIG. 9B according to a third embodiment.

Referring to FIG. 9D, a second rotating flinger (961) is positioned below the rotating flinger (660). From the seal annular gap (574) under the rotating flinger, most of the fluid will flow toward the second-flinger lower surface (963) and will be diverted towards the stationary fluid exit channel (556) which is fluidly connected to the second annular fluid manifold (552).

A portion of the fluid that that is not diverted towards the stationary fluid exit channel (556) will flow toward the rotating flinger lower surface (962). Most of this portion of the fluid will be diverted towards the stationary fluid exit channel (556) which is fluidly connected to the second annular fluid manifold (552).

The flingers (660, 961) are effective at directing the fluid when the shaft is rotating. The rotating shaft and fluid rotation create centrifugal forces acting on the fluid in the radial direction, outwards. The flinger's cross-sectional shape may be primarily square, primarily rectangular, primarily triangular wherein the slope of the triangle is in the direction of the turbine or primarily triangular wherein the slope of the rectangular faces towards the second bearing.

Even if, a small amount of fluid, humidity or vapor does pass the non-contact seal into gap (506) below second bearing (508), the small amount of fluid, humidity or vapor is not sufficient to compromise a non-water based bearing lubricant or grease in the second bearing (508). In one test, the second bearing (508) retained most of the original grease after 500 hours of machining operations.

Optional Contact Seals

Turning to FIG. 10, a second sealing system for use in the spindle (100) is shown. The second sealing system can include a seal housing (150) defining a major turbulence pocket (512) and a minor turbulence pocket (914) like the non-contact seal (900) of the first sealing system discussed above. This second sealing system further comprises a contact seal located between the second bearing (508) and turbine (570). Preferably, the contact seal is positioned as close as possible to the second bearing (508).

The contact seal is designed to prevent fluid, droplets and contamination from reaching the second bearing (508) when the spindle is at rest, even if the high speed spindle is stored in an ATC, or other storage, after it has been used, where the storage position is vertical (i.e. wherein the cutting tool is facing up) or horizontal or at any other angle. In such cases there is a concern that residual fluid that remains on the cutting tool, on the turbine or in the seal housing, will flow toward the second bearing.

The contact seal is designed to prevent these residual fluids from reaching the second bearing (508).

The contact seal spans the gap between the seal housing (150) that is connected to the high speed spindle body (120) and the rotating shaft (530) when the spindle is at rest.

The contact seal is designed to maintain contact with the seal housing (150) and the rotating shaft (530) when the shaft is at rest or rotating at low RPM, no more than 10% of the high speed spindle unloaded rotation speed.

The contact seal is designed to break contact between the seal housing (150) and the rotating shaft (530) when the shaft is rotating at high RPM. When the shaft is rotating at high RPM, there is no contact or friction between stationary components and the rotating components. In an embodiment, when the shaft is rotating, there is no contact or friction between stationary components and the rotating components.

Figure 10B:
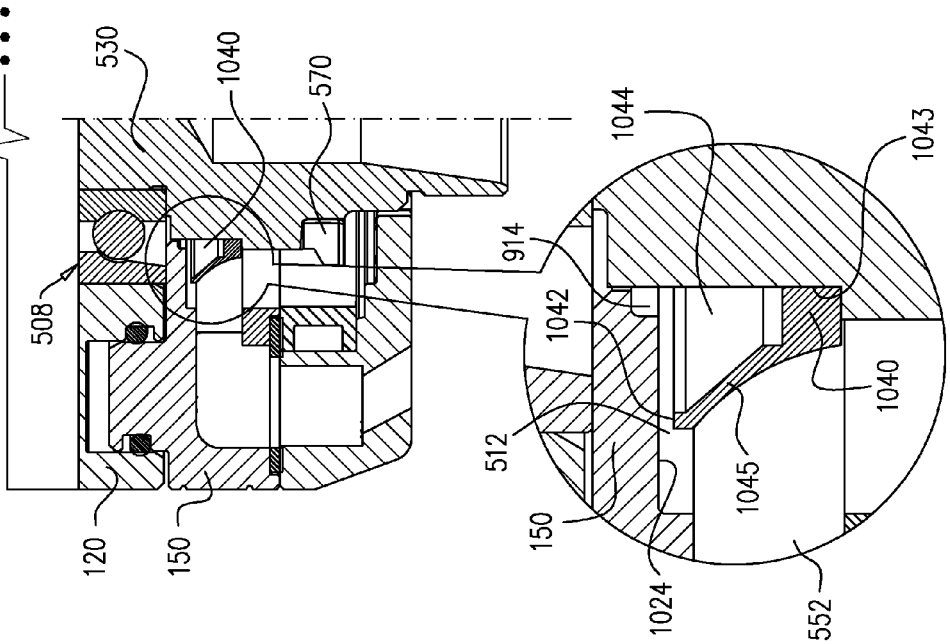
FIG. 10B shows a detailed cross sectional view of a spindle having a contact seal in a second position, according to the first embodiment.
Figure 10A:
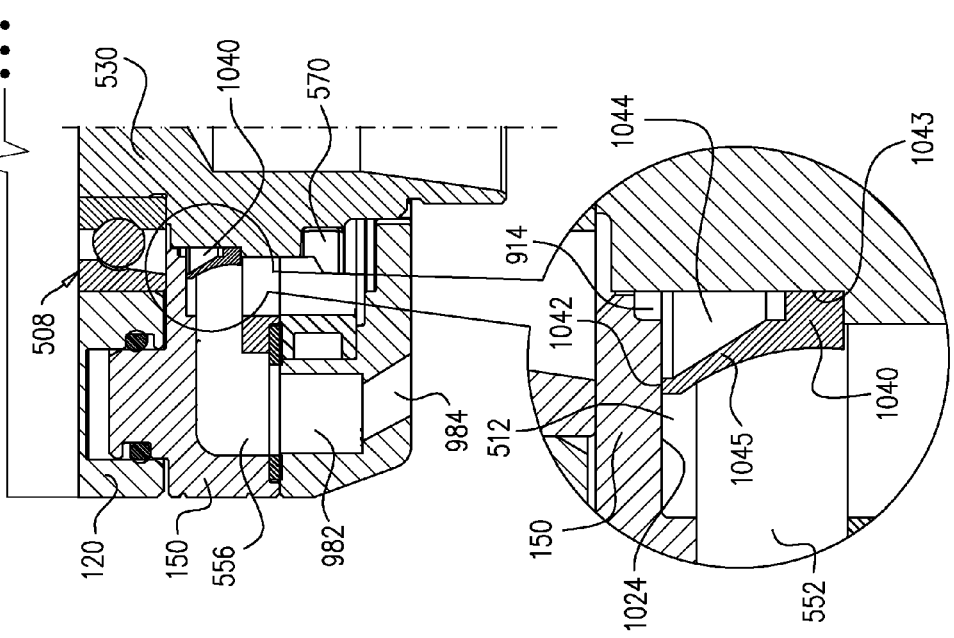
FIG. 10A shows a detailed cross sectional view of a spindle having a contact seal in a first position, according to a first embodiment.

Referring to FIG. 10A, a spring flinger (1040) is positioned on the rotating shaft (530) and rotates therewith. In this embodiment, the spring flinger may replace the relatively rigid flinger (660) found in the first sealing system embodiment. The spring flinger (1040) has the overall shape of an angular flap or skirt mounted on the shaft. Spring flinger (1040) includes flexible materials such as rubber or other elastomers or a shaped spring made of stiffer materials. The flexible materials allow the spring flinger to stretch and change shape when centrifugal forces are applied due to the shaft rotation.

In the illustrated embodiment, spring flinger (1040) has a spring flinger mounting surface (1043) that is used to mount the spring flinger on the shaft (530) and a flexible, thinner section (1044) with a spring flinger cross-section (1045). When the shaft (530) is not rotating, the flexible thinner section (1044) is positioned such that the spring flinger upper surface (1042) is in contact with seal housing (150). In the exemplified embodiment, spring flinger upper surface (1042) is in contact with stationary surface (1024). The contact line between spring flinger (1040) and seal housing (150) prevents fluid passage from one side of the contact line (area or ring) to the other.

Referring to FIG. 10B, during rotation of the shaft (530), centrifugal forces are applied on the spring flinger (1040) due to the shaft rotation. The flexible material allows the spring flinger (1040) to stretch such that spring flinger upper surface (1042) is relocated slightly away from stationary surface (1024) resulting in a lack of contact. The spring flinger (1040) functions as a flinger diverting fluid from the turbine area into second annular fluid manifold (552).

The spring flinger (1040) may include a heavier component (not shown), positioned on or within the flexible, thinner section (1044) that provides a weight for stretching the spring flinger (1040) during rotation. Where present, the heavier component may be ring or doughnut shaped or comprised of a plurality of sections. Where present, the heavier component may be molded to or within the spring flinger.

Turning to FIG. 11, a third embodiment of a sealing system, for use in a spindle (100), is shown. This third embodiment also includes a seal housing (150) partially defining a major turbulence pocket (512) and a minor turbulence pocket (914) between the seal housing (150) and portions of a flinger (660) to form a non-contact seal. The third embodiment further comprises a contact seal provided by flexible flap (1140) positioned on the seal housing (150). The flexible flap (1140) is shaped as an angular flap or skirt mounted on the seal housing (150). Flexible flap (1140) includes flexible materials such as rubber or other elastomers or a shaped spring made of stiffer materials. The flexible materials stretch and change shape due to fluid flow against them.

The flexible flap (1140) has a spring seal mounting surface (1143) that is used to mount the seal on the seal housing (150) and a flexible portion (1144) whose cross section is (1145). When the shaft (530) is not rotating, the flexible portion (1144) is positioned such that the flexible flap lower surface (1142) is in contact with the flinger (660). In the exemplified embodiment, flexible flap lower surface (1142) is in contact with flinger upper surface (966). The contact line (area or ring) between flexible flap (1140) and the shaft flinger (660) prevents fluid passage from one side of the contact line to the other.

Referring to FIG. 11B, during rotation of the shaft (530), fluid flows up from the turbine area, through the seal annular gap (574) between the rotating shaft (530) and the seal housing (150). Fluid that flows above the flinger (660) applies force on the bottom surface of flexible portion (1144), pushing it slightly toward stationary surface (1024) of the seal housing (150). The motion of the flexible portion (1144) toward the stationary surface (1024) of the seal housing (150) breaks the contact.

In some embodiments, flexible flap (1140) may include a heavier component (not shown), positioned on or within the flexible portion (1144) that creates a stronger seal. The relatively heavy component may comprise a ring or doughnut shaped element in one or more sections, that is attached to or molded with the flexible flap (1140) such as a metal ring molded into the rubber flexible flap (1140).

Figure 12B:
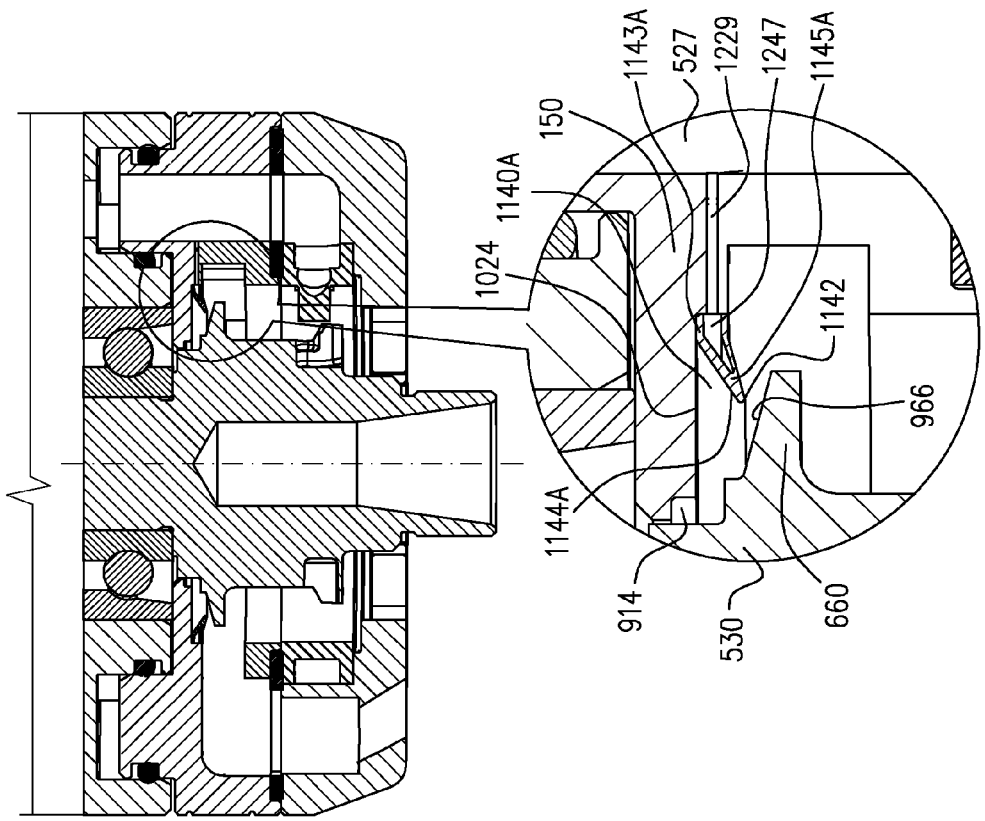
FIG. 12B shows a detailed cross sectional view of a spindle having a contact seal in a second position, according to the third embodiment.
Figure 12A:
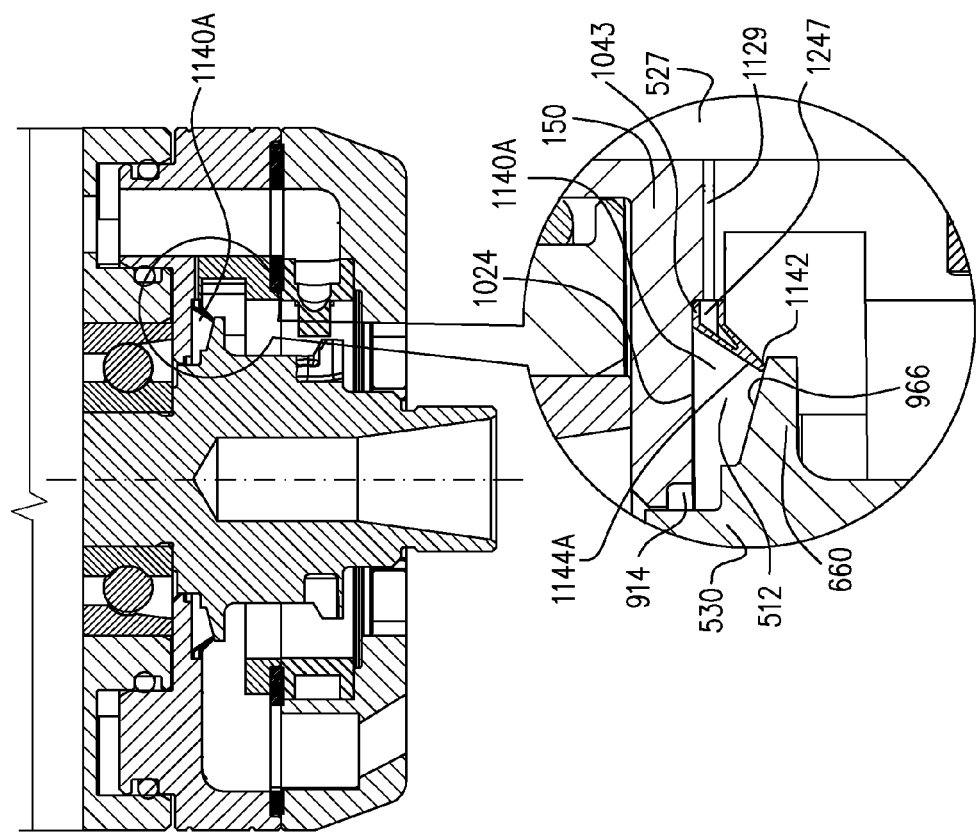
FIG. 12A shows a detailed cross sectional view of a spindle having a contact seal in a first position, according to a third embodiment.

Turning to FIGS. 12A and 12B, a fourth embodiment of a seal system, for use within spindle (100), is shown. This fourth embodiment also includes seal housing (150) defining a major turbulence pocket (512) and a minor turbulence pocket (914) above a flinger (660) to provide a non-contact seal as discussed in detail with respect to FIG. 9. This embodiment of the seal system further comprises a contact seal much like the third embodiment discussed with respect to FIG. 11. This embodiment includes a flexible flap (1140A) positioned on the seal housing (150). The flexible flap (1140A) is shaped as an annular flap or skirt mounted on the seal housing (150). The flexible flap (1140A) includes a flexible flap cavity (1247). An auxiliary fluid channel (1229) fluidly connects the flexible flap cavity (1247) with the high pressure secondary vertical fluid channel (527).

The flexible flap (1140A) includes flexible materials such as rubber or other elastomers or a shaped spring made of stiffer materials. The flexible materials stretch and change shape due to fluid pressure within the flexible flap cavity (1247).

The flexible flap (1140A) has a seal mounting surface (1143A) that is used to mount the seal on the seal housing (150) and a flexible portion (1144A) whose cross section is (1245). When the shaft (530) is not rotating, and the pressure in the high pressure secondary vertical fluid channel (527) is small or nil, the flexible flap (1140A) is positioned such that the flexible flap lower surface (1142) is in contact with the flinger (660). In the exemplified embodiment, the flexible flap lower surface (1142) is in contact with flinger upper surface (966). The contact line (area or ring) between flexible flap (1140A) and the shaft flinger (660) prevents fluid passage from one side of the contact line to the other.

Referring to FIG. 12B, during rotation of the shaft (530), high pressure fluid flows in the high pressure secondary vertical fluid channel (527) on route to the turbine. A portion of the high pressure fluid fills auxiliary fluid channel (1229) and flexible flap cavity (1247). The pressurized fluid within the flexible flap cavity (1247) applies a force on the flexible flap (1140A) and causes it to bend toward stationary surface (1024) of the seal housing (150).

The motion of the flexible portion (1144A) toward stationary surface (1024) breaks the contact between seal housing (150) and the rotating shaft (530).

In some embodiments, flexible flap (1140A) may include a heavier component (not shown), positioned on or within the flexible portion (1144A) that creates a stronger seal. The relatively heavy component may comprise a ring or doughnut shaped element in one or more sections, that is attached to or molded with the flexible flap (1140A) such as a metal ring molded into the rubber flexible flap (1140A).

Optional Flow Control Feature

Figure 13B:
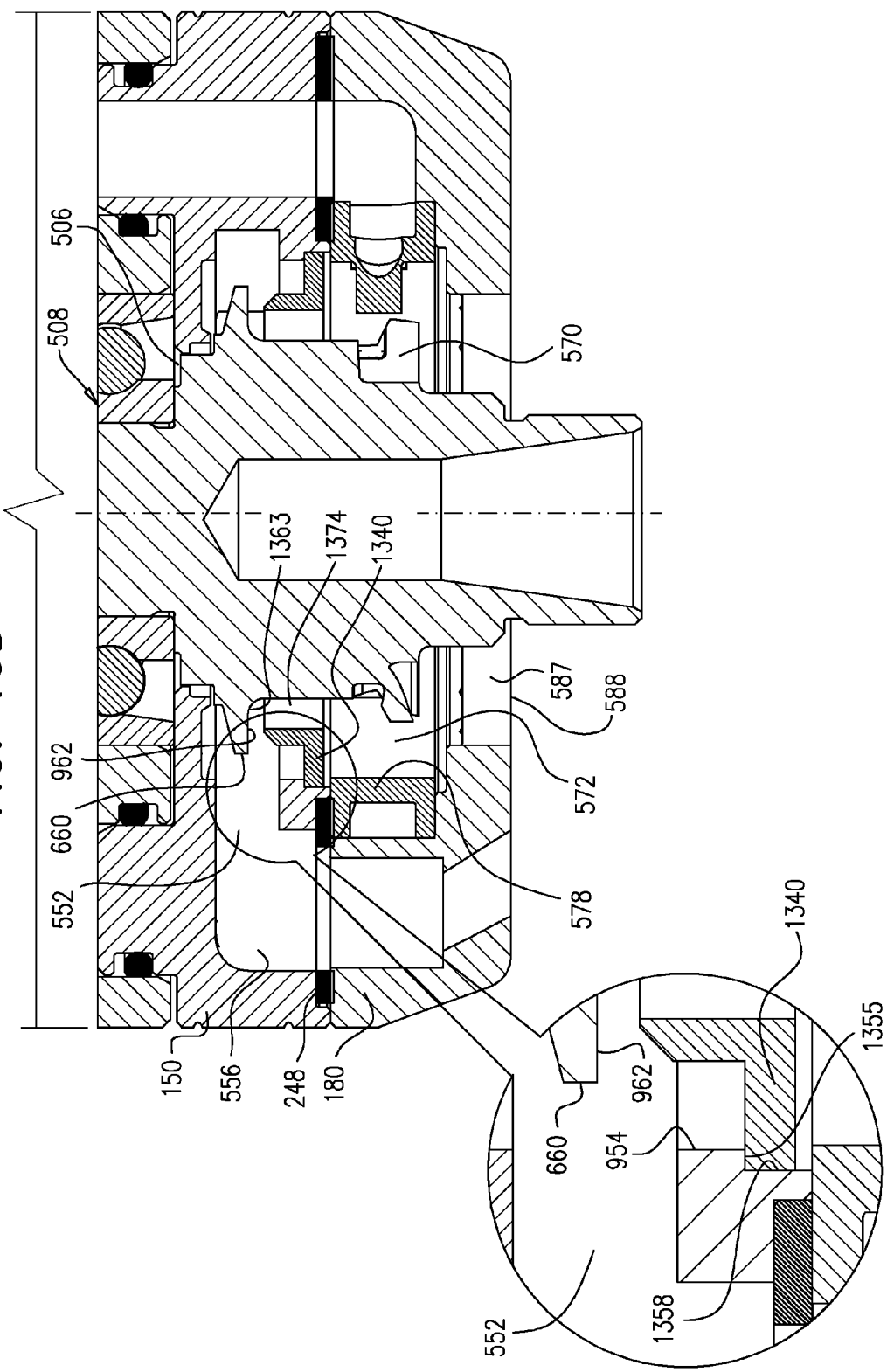
FIG. 13B shows a detailed view of the non-contact seal and cover portion according to another embodiment.

Referring to FIGS. 13A and 13B, the illustrated embodiment of the spindle includes a non-contact seal between spindle body (120) and cover (180) substantially similar to the non-contact seal (900), wherein the illustrated embodiment further comprises a second stationary element (1340) connected to the seal housing (150).

In the exemplified embodiment, the second stationary element (1340) is a stationary ring that is positioned on a corresponding feature in the seal housing (150). For example, the corresponding feature in the seal housing (150) is a step defined by the seal housing inner surface (954), a first surface (1355) which is primarily perpendicular to seal housing inner surface (954) and second surface (1358) which is primarily perpendicular to the first surface (1355). The dimensions of the outer diameter of the second stationary element (1340) and the diameter of the seal housing inner surface (954) are such that there is an interference fit between the second stationary element (1340) and seal housing (150). Alternatively the second stationary element (1340) is connected to the seal housing (150) with an adhesive or any other means.

The second stationary element (1340) forms a more narrow seal annular channel (1374) below flinger (660), than in the embodiment of FIG. 5. The narrow seal annular channel (1374) directs fluid coming from cover annular gap (572) to the root (1363) of the flinger lower surface (962). Due to fluid pressure and centrifugal forces acting on the fluid, fluid will flow towards the stationary fluid exit channel (556) through stationary second annular fluid manifold (552) and to a fluid opening in the cover (180) or to a fluid opening (see FIG. 14) in the seal housing (150).

Lateral Discharge Spindles (with Similar Non-Contact Seal)

Figure 14A:
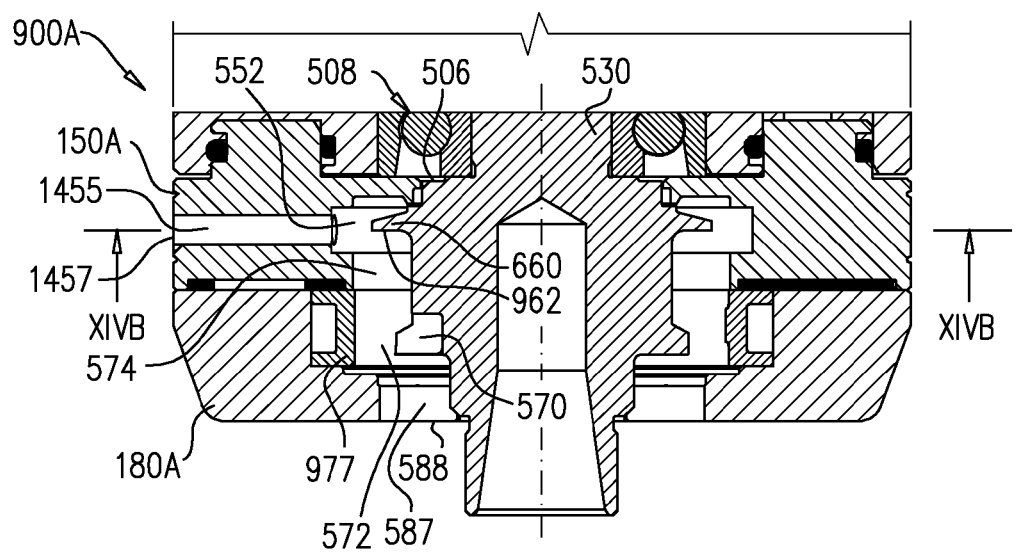
FIG. 14A shows a detailed view of the non-contact seal and cover portion according to yet another embodiment.

Turning to FIGS. 14A-14D, additional embodiments of the non-contact seal portion of the spindle are shown which have alternative fluid exit arrangements. Referring to FIG. 14A, the non-contact seal (900A) can include a flinger (660), a major turbulence pocket and a minor turbulence pocket as previously discussed with respect to FIGS. 5-9. The embodiments of FIG. 14A-14D can be distinguished from the embodiment of FIG. 9 due to changes the seal housing (150A) and the cover (180A) that alter the direction of fluid exit.

At least one lateral fluid exit channel (1455) may replace, or alternatively extend from the plurality of stationary exit channels (556) shown in FIG. 5, thereby having the lateral fluid exit channel (1455) directly or indirectly extending from the annular fluid manifold (552). The at least one lateral fluid exit channel (1455) extends along a plane generally perpendicular to the shaft.

The non-contact seal (900A) is positioned between the second bearing (508) which is mounted on the shaft (530) and turbine (570).

The non-contact seal (900A) includes: a seal housing (150A); the second annular fluid manifold (552), primarily within the seal housing; the first rotating flinger (660); and a lateral fluid exit channel (1455) within the seal housing (150). The lateral fluid exit channel (1455) is approximately on the same plane of the rotating flinger.

In other embodiments, there are multiple rotating flingers, on different planes. The planes being perpendicular to the rotating shaft. In such cases, there may be multiple lateral fluid exit channels (1455) approximately on the same planes as the rotating flingers.

The annular gap sections between the rotating components and the stationary components, through which, fluid flows, include: the cover annular gap (572) between the turbine (570) and nozzle ring (977) and the seal annular gap (574) under the rotating flinger.

The fluid leaves the high speed spindle through sidewall fluid exit opening (1457) in the seal housing (150).

High pressure fluid flowing through the at least one nozzle (not shown) and directed at the at least one turbine (570) causes the shaft to rotate at high speed.

The fluid impacting the turbine (570) is diverted into the cover annular gap (572). From the cover annular gap (572) the fluid flows into the seal annular gap (574) under the rotating flinger.

Most of the fluid flowing into seal annular gap (574) will flow through second annular fluid manifold (552) toward lateral fluid exit channel (1455) and exit the high speed spindle via sidewall fluid exit opening (1457).

A portion of the fluid in the cover annular gap (572) flows along the shaft through bottom annular cavity (587) and through first axial exit opening (588).

Figure 14B:
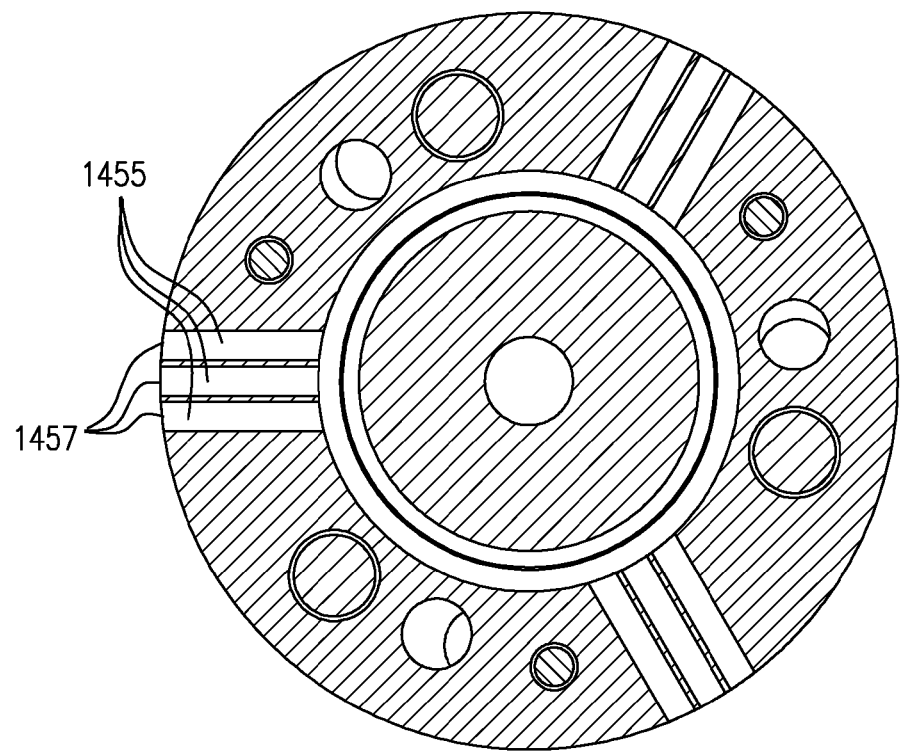
FIG. 14B shows a cross sectional view of the non-contact seal of FIG. 14A through plane XIVB-XIVB according to a first embodiment.

Referring to FIG. 14B, in one embodiment, the lateral fluid exit channels (1455) are positioned in the radial direction, exiting the seal housing (150) through sidewall fluid exit opening (1457). In the exemplified embodiment, there are three clusters of three parallel fluid exit openings spaced approximately at 120 degrees.

In some embodiments, the fluid flows from second annular fluid manifold (552) through multiple lateral fluid exit channels (1455) approximately equally spaced around the circumference of the seal housing (150).

The diameter of the lateral fluid exit channels (1455) is such that the total cross sectional area of the lateral fluid exit channels (1455) is approximately equal to the cross section of the second annular fluid manifold (552) in a plane that is perpendicular to the shaft at the location that the horizontal exit channels intersect with second annular fluid manifold (552).

The total cross sectional area of the lateral fluid exit channels (1455) is approximately equal to the cross sectional area of the bottom annular gap (587) at the plane of the first axial exit opening (588).

The cross section of each lateral fluid exit channel (1455) can be round or oval. The cross section of the lateral fluid exit channel (1455) may have only rounded features.

Figure 14C:
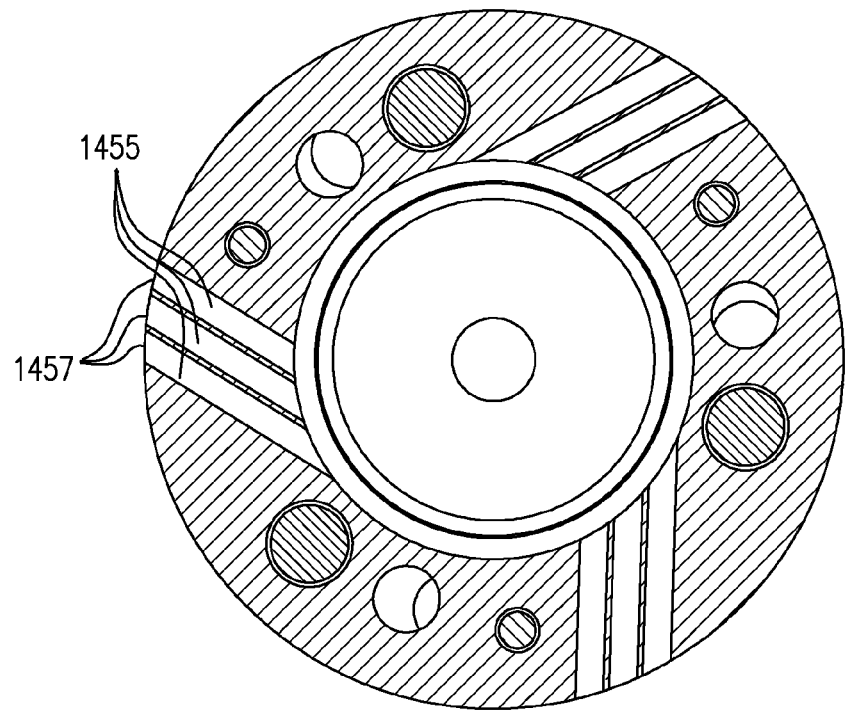
FIG. 14C shows a cross sectional view of the non-contact seal of FIG. 14A through plane XIVB-XIVB according to a second embodiment.

Referring now to FIG. 14C, another configuration of the lateral fluid exit channels (1455) is shown. The lateral fluid exit channels (1455) are positioned at an angle that is primarily tangential to the second annular fluid manifold (552) exiting the seal housing (150) through sidewall fluid exit opening (1457). In the exemplified embodiment, there are three groups of three parallel fluid exit openings.

Figure 14D:
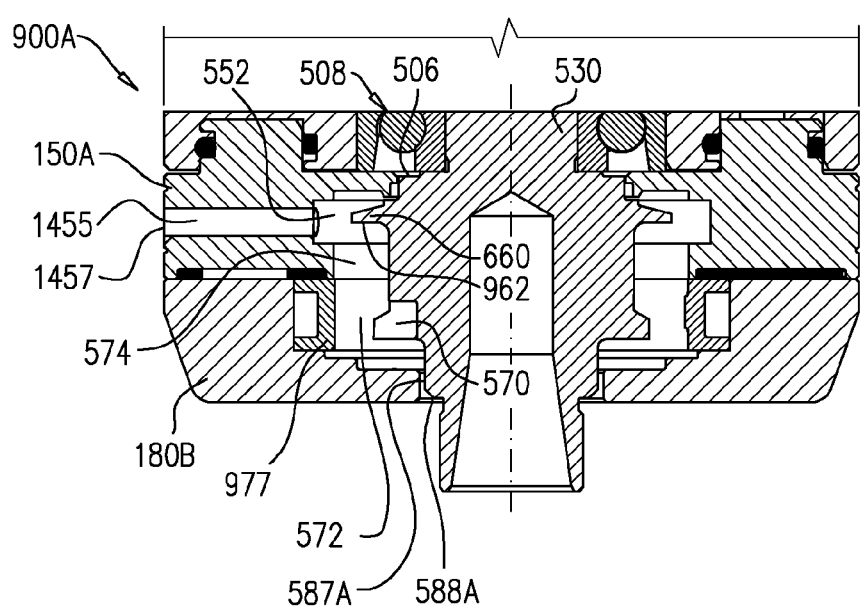
FIG. 14D shows a detailed view of the non-contact seal and the cover portion according to yet another embodiment.

Referring to FIG. 14D, another embodiment of the fluid exit structure is shown. The illustrated embodiment includes a seal housing (150A) substantially similar to the seal housing (150A) seen in FIG. 14A. The illustrated embodiment includes an alternative cover (180B) having the bottom annular gap (587A) and the first axial exit opening (588A) being significantly smaller, substantially restricting flow of fluid out of the first axial exit opening (588A), such that most of the fluid within the spindle will exit the sidewall fluid exit opening (1457). In the illustrated embodiment, the bottom annular gap (587A) is less than 0.5 mm wide, preferably less than 0.35 mm wide, more preferably less than 0.2 mm wide and most preferably less than 0.1 mm wide.

Figure 15:
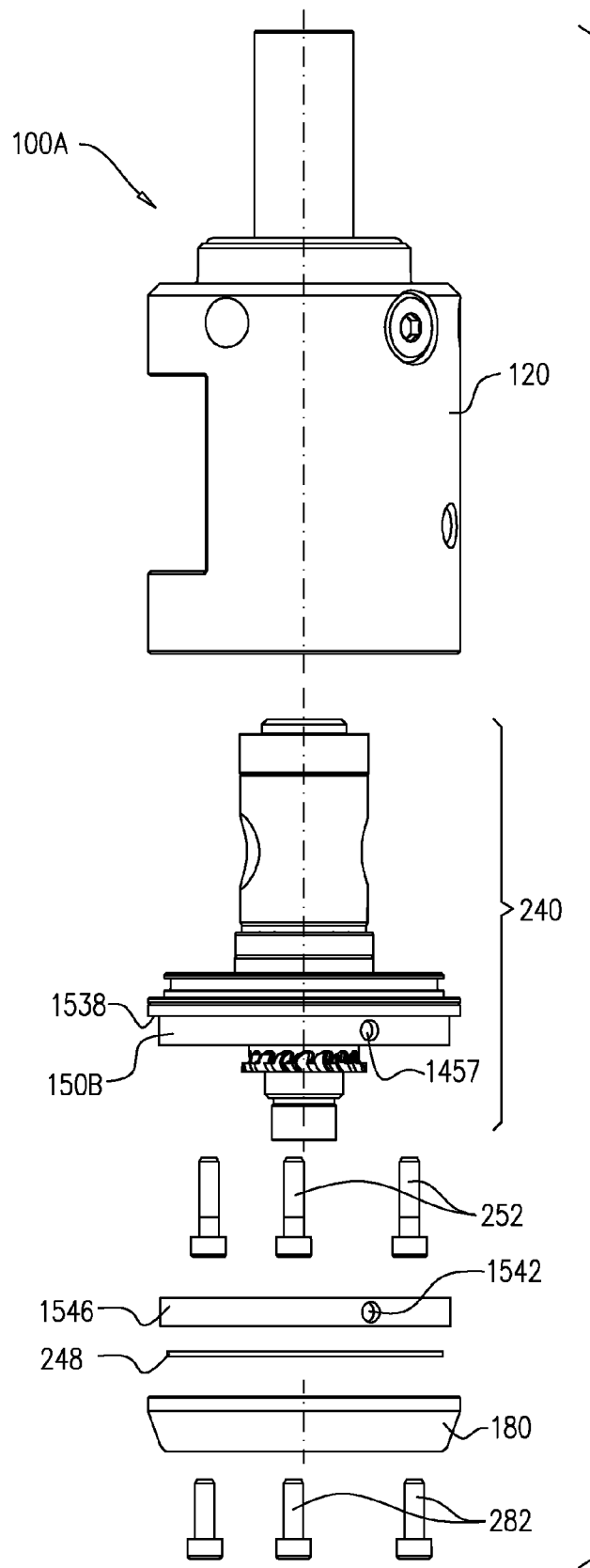
FIG. 15 shows an exploded view of the spindle having a side by-pass according to the embodiments of FIGS. 14A-14D with a control ring.

Turning to FIG. 15, an exploded view of spindle 100A is shown. The embodiment of the spindle shown in FIG. A is substantially similar to the exploded view shown in FIG. 2, with two main distinctions. One, the seal housing (150B) shown in FIG. 15 combines features of the seal housing (150) from FIG. 5 and seal housing (150A) from FIG. 14. This combination of features is best shown in FIG. 16. Second, the illustrated embodiment further comprises a rotatable ring (1546). The rotatable ring (1546) is positioned on the seal housing (150B) and benched against seal housing ledge (1538).

The rotatable ring (1546) is disposed around the body (120) generally coplanar with the at least one lateral fluid exit channel (1455). The rotatable ring (1546) has at least one ring opening (1542) therein, wherein the rotatable ring (1546) is capable of opening and closing an end of the at least one lateral fluid exit channel (1455) by selectively positioning the ring opening (1542) with respect thereto.

The rotatable ring (1546) includes a ring opening (1542) rotationally positionable relative to the more or more sidewall fluid exit openings (1457) in the seal housing (150B). The position of rotatable ring (1546) is adjustable such that the ring opening (1542) can be in line, partially in line, or full offset with the sidewall fluid exit opening (1457) such that the flow of fluid from the horizontal fluid exit opening is controlled by the position of the rotatable ring (1546). The rotatable ring (1546) may have a plurality of ring openings (1542) and the seal housing (150A) may have a plurality of sidewall fluid exit openings (1457) as discussed above. The number of ring openings (1542) may or may not equal the number of sidewall fluid exit openings (1457).

Spindles with Bottom and Side Fluid Discharge

Turning to FIGS. 16A and 16B, yet another embodiment of the non-contact seal is shown. FIGS. 16A and 16B reflect cross-sectional views of the spindle 100A shown in FIG. 15. The non-contact seal is substantially similar to the configuration of FIG. 9 with respect to the combination of a separate flinger (660A) combining with a seal housing (150B) to create a major turbulence pocket and a minor turbulence pocket (not labeled).

The illustrated non-contact seal also includes the exit channel structure of FIG. 9, but adds at least one lateral fluid exit channel (1455) and sidewall fluid exit opening (1457) to the seal housing (150B) as discussed with respect to FIG. 14. Further, the illustrated embodiment includes the rotatable ring (1546) having ring opening (1542) as discussed with respect to FIG. 15. FIG. 16A shows the ring opening (1542) aligned with the sidewall fluid exit opening (1457) and FIG. 16B shows the position where the ring opening is not aligned with the sidewall fluid exit opening (1457), i.e. the sidewall fluid exit opening (1457) is blocked by the rotatable ring (1546).

Figure 17:
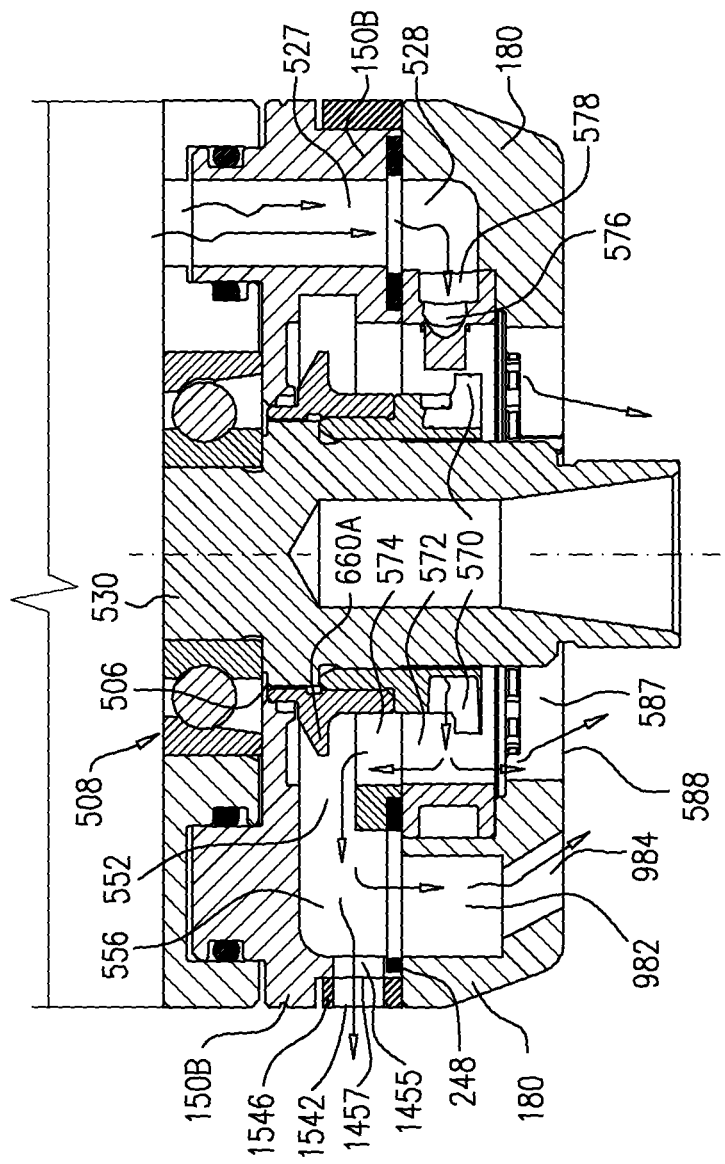
FIG. 17 is a cross section of the spindle of FIG. 15 schematically showing the fluid path.

Turning to FIG. 17, flow arrows are included to schematically represent the fluid flow within the non-contact seal embodiment from FIG. 16. Fluid enters the non-contact seal system through secondary vertical fluid channel (527) in the seal housing (150B) and through inlet channel (528) in the cover (180).

From the inlet channel (528) the fluid enters the nozzle fluid manifold (578) and to the at least one nozzle (576). The fluid exiting the at least one nozzle (576) is directed toward turbine (570) that causes the turbine to rotate at high speed. A portion of the fluid impacting the turbine is diverted from the turbine toward the shaft tool end into bottom annular cavity (587) and through first axial exit opening (588).

Due to the high centrifugal forces, the remaining fluid is diverted from the turbine, into the cover annular gap (572) between the rotating turbine and nozzle ring. From the cover annular gap (572) the fluid flows into the seal annular gap (574) under the rotating flinger (660A) and to the second annular fluid manifold (552).

From the second annular fluid manifold (552) in the seal housing (150B) the fluid continues to the stationary fluid exit channel (556).

In the illustrated embodiment, a ring opening (1542) is in line with sidewall fluid exit opening (1457) and a portion of the fluid flows through lateral fluid exit channel (1455) within seal housing (150B) and through the ring opening (1542) and exits the high speed spindle. The rest of the fluid flows from the stationary fluid exit channel (556) to axial fluid exit channels: section one (982) and section two (984), in the cover (180).

When the ring opening (1542) is not in line with sidewall fluid exit opening (1457) and sidewall fluid exit opening (1457) is blocked by the rotatable ring (1546). Fluid flows from the stationary fluid exit channel (556) to axial fluid exit channels: section one (982) and section two (984), in the cover (180).

In a third position, the ring opening (1542) is positioned such that it is partially in line with sidewall fluid exit opening (1457) and a controlled portion of the fluid flows through lateral fluid exit channel (1455) within the seal housing (150B) and through the ring opening (1542) and exits the high speed spindle. The rest of the fluid flows from the stationary fluid exit channel (556) to axial fluid exit channels: section one (982) and section two (984), in the cover (180).

In other embodiments, the cover (180) may be replaced by the cover (180A) of FIG. 14A, without section one (982) or section two (984). In other embodiments, the cover (180) may be replaced by cover (180B) as shown in FIG. 14D, providing only a minimal first axial exit opening (588A)

In different applications it is desired to control the amount of fluid in the vicinity of the work piece and the flow pattern with which it affects the machining process. In general, fluid existing in proximity to the rotating shaft and cutting tool will create a bigger splash and have less momentum upon reaching the work piece. Fluid directed at the work piece at an angle such that the jet of fluid is not affected by the rotational elements, will typically maintain a well-defined jet shape and reach the work piece with a higher momentum.

There are machining operations that require dry or semi dry machining conditions. Providing the sidewall fluid exits enables deploying the fluid driven high speed spindle also for dry and semi dry applications.

Cover and Nozzle Detail

Figure 18A:
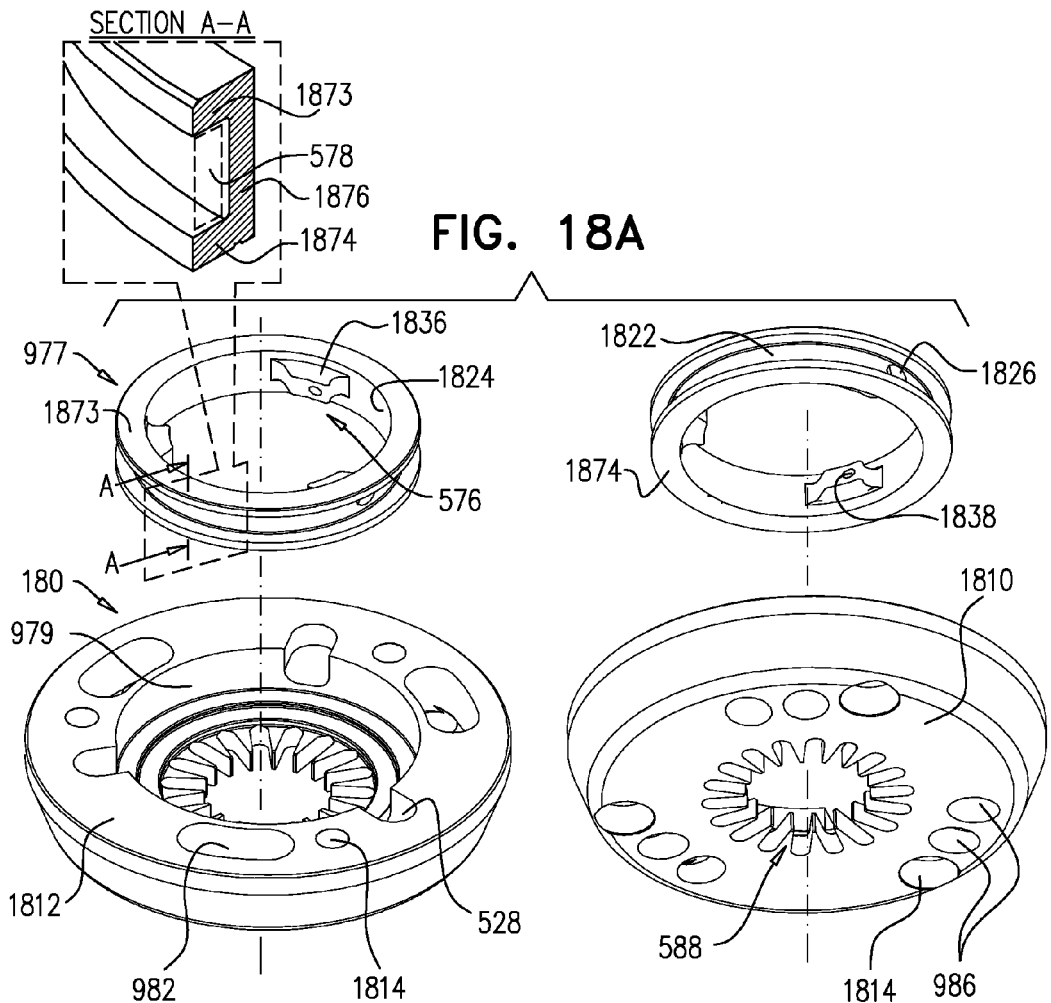
FIG. 18A is an exploded perspective view of the nozzle and cover shown in FIG. 2.
Figure 18B:
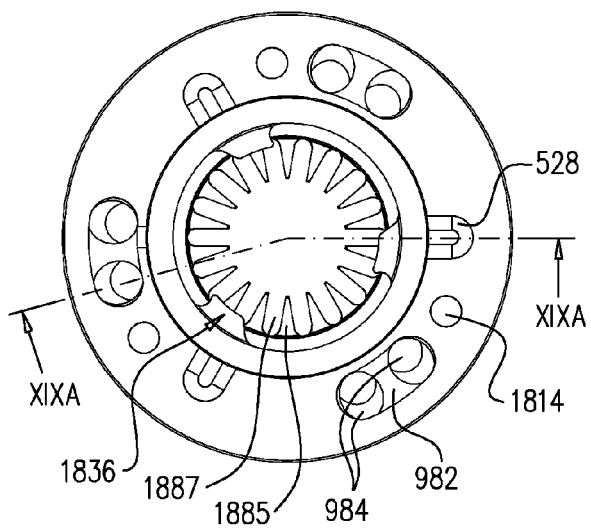
FIG. 18B is a top view of the nozzle assembled with cover shown in FIG. 2.

Turning to FIGS. 18A and 18B, detailed views of the cover (180) and nozzle (576) are shown. As discussed above, the spindle body comprises a channel system by which fluid can communicate from the shank to an end point of the system that is in proximity to the turbine. The channel system ends with a nozzle fluid manifold (578) and nozzles (576) that are in proximity to the turbine. The nozzle fluid manifold distributes fluid from at least one inlet channel (528) to the at least one nozzle (576). Preferably, the nozzle provides a relatively small opening, such that the fluid exiting the nozzle forms a fluid jet.

The direction of the fluid exiting the at least one nozzle and impacting the turbine has a component that is tangential to the turbine circumference and an additional inward radial vector component, toward the shaft. If the nozzles and turbine are not on the same plane and the direction of the fluid exiting the nozzles and impacting the turbine will also have a vertical component.

As understood from the exploded view of FIG. 18A, the nozzle ring (977) is inserted in the cover (180) of the high speed spindle. The nozzle ring (977) partially defines the nozzle fluid manifold (578) and the at least one nozzle covering (1836).

The at least one nozzle covering (1836), positioned on the nozzle ring internal surface (1824) houses the nozzle channel (see FIG. 19), including the nozzle fluid exit (1838). The at least one nozzle inlet (1826) is positioned within the nozzle ring external surface (1822). The nozzle covering (1836) may house multiple nozzle channels (not shown).

Turning to SECTION A-A, the nozzle fluid manifold (578) is defined by three sections of the nozzle ring (977): a first horizontal section (1873), a vertical section (1876) and a second horizontal section (1874), along with the cover inner surface (979).

The cover (180) includes two primary surfaces: the interface surface (1812) that interfaces with the gasket and the seal housing, and the external surface (1810).

The cover (180) includes: at least one axial fluid exit channel first section (982), at least one screw hole (1814), at least one inlet channel (528) that interfaces with the nozzle fluid manifold (578), at least one axial fluid exit channel second section (984) with a second axial exit opening (586) on the external surface (1810), and a first axial exit opening (588) in proximity of the turbine.

In the exemplified embodiment, the axial fluid exit channel first section (982) is oval shaped and fluidly connects with two axial fluid exit channel second sections (984). This configuration results in two fluid jets exiting the high speed spindle cover (180). In another embodiment, the first section of the fluid exit channel fluidly connects with at least one second section of the fluid exit channel. In another embodiment, the first section of the fluid exit channel fluidly connects with multiple second sections of the fluid exit channel.

Referring to FIG. 18B, a top view of the nozzle ring (977) assembled with the cover (180) is shown. Also visible is the axial fluid exit opening that includes at least two ribs (1885) and two rib-gaps (1887) between ribs (1885).

In the exemplified embodiment, inlet channel (528) is positioned opposite nozzle inlet (1826) and nozzle covering (1836).

In an embodiment, the number of nozzle fluid exits (1838) from the nozzle fluid manifold (578) is different than the number of inlet channels (528). In another embodiment, the position of at least one nozzle fluid exit (1838) is not approximately opposite at least one inlet channel (528). In another embodiment, the spacing of the nozzle fluid exits (1838) is different than the spacing of inlet channels (528). Preferably, the nozzle fluid exits (1838) are equally spaced.

Figure 19A:
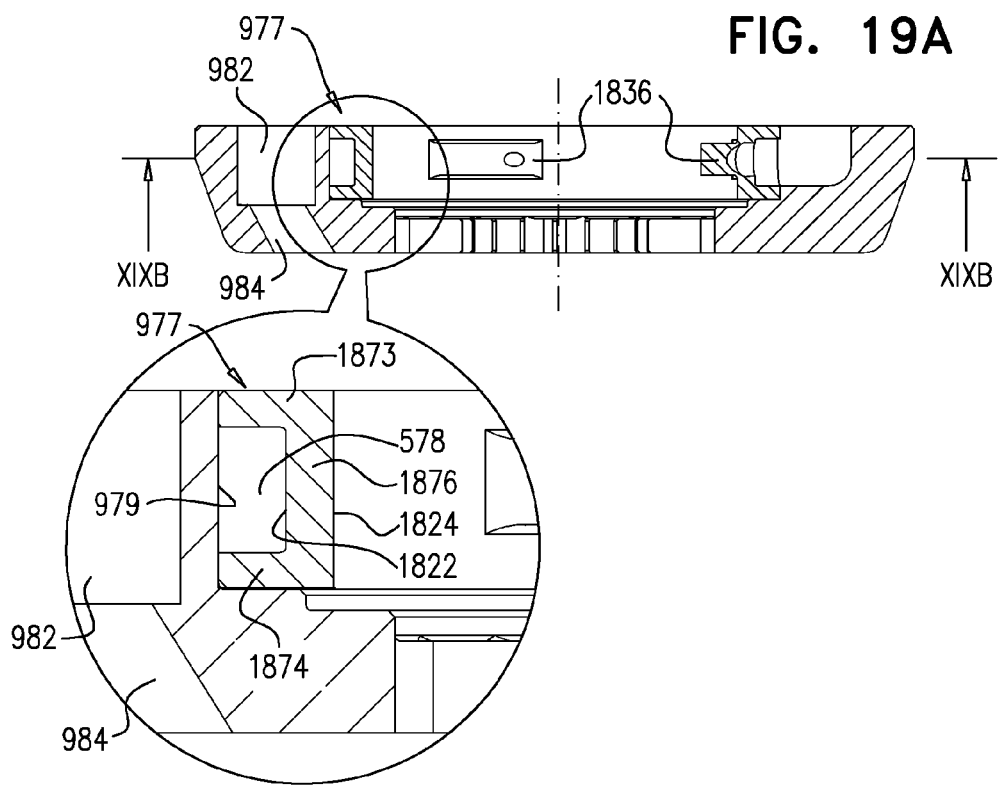
FIG. 19A is a vertical cross section of the nozzle and cover shown in FIGS. 18A and 18B.
Figure 19B:
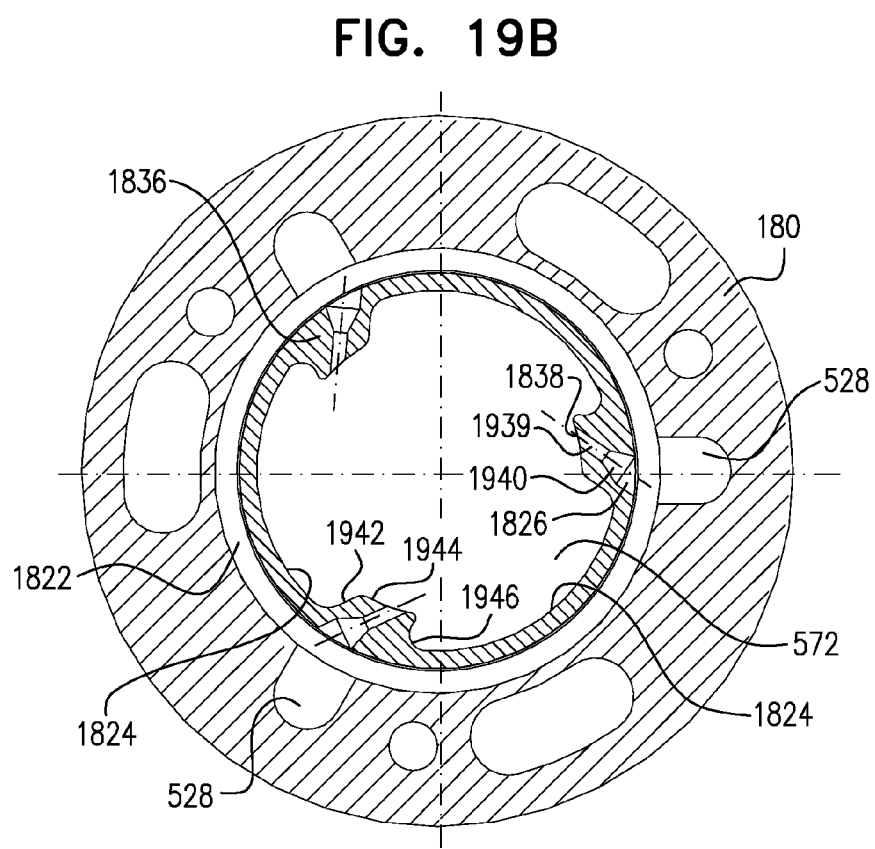
FIG. 19B is a horizontal cross section of the nozzle and cover shown in FIGS. 18A and 18B.

Referring to FIGS. 19A and 19B, horizontal and vertical cross sections of the nozzle/cover assembly from FIG. 18B are shown.

In the exemplified embodiment the axial fluid exit channel first section (982) fluidly connects at least one axial fluid exit channel second section (984) wherein the second section (984) is at an angle with respect to the axial fluid exit channel first section (982). The above configuration provides a means to direct the fluid jet exiting the at least one second section in a preferred direction, while maintaining design flexibility with respect to the location and diameter of the first section of the fluid exit channel. In one embodiment, the preferred direction is toward the tool end. In another embodiment, the preferred direction is away from the tool end, and in yet another embodiment, the preferred direction is adjustable. In other embodiments, multiple second sections of axial fluid exit channels are provided within the cover, the second sections (984) being directed at different angles.

In the exemplified embodiment the nozzle fluid manifold (578) is defined by three sections of the nozzle ring (977) sections: the first horizontal section (1873), the vertical section (1876) and the second horizontal section (1874), as well as the cover inner surface (979).

The cross section of the nozzle fluid manifold (578) may be rectangular, circular, doughnut shaped and/or divided into multiple sections.

In other embodiments, the nozzle ring can be L shaped, including only the first horizontal section (1873) and the vertical section (1876), wherein, the nozzle fluid manifold (578) is then defined by the cover inner surface (979) and a step on which the nozzle ring is benched. The nozzle fluid manifold (578) can be created by inserting the nozzle ring into a complimentary feature in the high speed spindle cover such that the two parts form a closed manifold, with opening to at least one inlet channel (528) and to at least one nozzle fluid exit (1838).

In the exemplified embodiment of FIG. 19B, the nozzle includes: a nozzle inlet (1826), a nozzle funnel (1940), a nozzle channel (1939) and a nozzle fluid exit (1838). The direction of the nozzle components are in line and at an angle to the radial direction. The angle is such that the fluid jet exiting the nozzle will impact at least one turbine blade. Preferably the angle is such that the fluid jet exiting the nozzle will impact the at least one turbine blade with the maximum tangential vector.

In another embodiment, the nozzle includes: a nozzle inlet (1826), a nozzle funnel (1940), a nozzle channel (1939) and a nozzle fluid exit (1838) that are housed within the nozzle covering (1836). In some embodiments, multiple nozzles are housed within each nozzle covering (1836).

The nozzle inlet (1826) on the nozzle ring external surface (1822) may be positioned approximately opposite inlet channel (528).

The cross section area of the nozzle channel (1939) is smaller than the nozzle inlet (1826) cross section such that the fluid velocity increases as it flows from the nozzle inlet (1826) and nozzle funnel (1940) to the nozzle channel (1939). The funnel (1940) fluidly connects nozzle inlet (1826) and the nozzle channel (1939) with a smooth couture. The design of the funnel (1940) is instrumental in drilling the nozzle channel (1939).

In one embodiment, the cross section area of the nozzle channel (1939) is round. The nozzle channel (1939) diameter to length ratio affects the shape and momentum of the fluid exiting the nozzle channel. In one example, the nozzle channel (1939) length to diameter ratio is smaller than 1.0. In another example, the nozzle channel (1939) length to diameter (length/diameter) ratio is equal to or larger than 1. In yet another example, the nozzle channel (1939) length to diameter ratio is equal to or larger than 2. In other embodiments, the nozzle channel (1939) length to diameter ratio is larger than 3. In further embodiments, the nozzle channel (1939) length to diameter ratio is larger than 4.

The shape of the nozzle fluid exit (1838) affects the shape and momentum of the fluid jet exiting the nozzle channel (1939). In an embodiment, the nozzle fluid exit (1838) is round. In an embodiment, the plane defined by the nozzle fluid exit (1838) is at an angle to the nozzle channel (1939) length axis, such that a nozzle with a round cross section along its length will have an elliptical opening. In an embodiment, the nozzle exit is elliptical. In an embodiment, the nozzle exit is primarily rectangular shaped. In an embodiment, the nozzle exit is primarily triangular shaped.

In the exemplified embodiment, the nozzle covering (1836) is not symmetrical. The nozzle covering (1836) includes: a first slope (1942), an apex (1944) and a second slope (1946). The first slope (1942) and second slope (1946) are angled in a similar direction as that of the nozzle channel (1939) while having rounded contours connected to the nozzle ring internal surface (1824). In some embodiments, the nozzle covering (1836) is symmetrically shaped. In some embodiments, the nozzle covering's first and second slopes are rounded such that the nozzle covering forms a semicircular feature.

In order to obtain high speed and significant power in small diameter turbines, the turbine blades must be impacted with a concentrated high momentum jet of fluid. In order to do so, the jets must be positioned as close possible to the turbine blades. However, the amount of fluid impacting the blades must be evacuated continuously, at the same pace that fresh fluid is being supplied. Fluid must be evacuated from within the turbine blade region as well as from the gap between the nozzle ring and the turbine blades. Fluid that is not evacuated in a timely manner slows down the turbine, and increases fluid friction, hence reducing turbine efficiency.

Nozzle ring internal surface (1824) and the adjacent nozzle coverings (1836) define a cover annular gap (572) in which fluid exiting the turbine fins can flow through. The cover annular gap (572) is designed to accommodate the volume of fluid exiting the turbine while maintaining sufficient pressure to flow effectively without slowing down the turbine. In one example, the nozzle channel (1939) length is designed such that the nozzle covering apex (1944) is as close as possible, within manufacturing tolerances, to the turbine. Preferable the distance between the nozzle covering apex (1944) and the turbine blades is smaller than 50 or 100 or 250 or 500 micrometers.

In the exemplified embodiment, the nozzle direction is such that the turbine rotates in a counter clock wise direction. In another embodiment, the nozzle direction is such that the turbine rotates in a clock wise direction.

Optional Cavity Vents

Turning to FIG. 20, the details of the vent (450) in the high speed spindle body (120) is shown. The vent (450) can be used in any of the embodiments of the spindles discussed above. The vent (450) reduces pressure fluctuations that may occur due to the high speed rotating elements within the spindle cavity (440). The vent connects the high speed spindle cavity (440) with the exterior (496) of the high speed spindle, through the high speed spindle body (120). The vent (450) is sealed with a vent gasket (2054) that remains closed at one atmosphere but will leak when the pressure differs between both sides of the gasket, allowing for pressure equalization.

Vent gasket (2054) will leak due to changes to its geometry, caused by an imbalance of pressure on both of its faces. The change in geometry provides a conduit for fluid to pass to and from the high speed spindle cavity (440) to and from the exterior to the high speed spindle.

For example, the vent gasket (2054) may leak when the pressure fluctuates by 0.05 atmospheres, 0.1 atmospheres or up to 0.17 atmosphere difference.

The vent gasket (2054) is made of a flexible material. In one example, the gasket is made of rubber. In some embodiments, the vent gasket (2054) is made of a flexible material with at least one slit. In one example, the gasket is made of a flexible material with more than one slit in different directions. In other examples, the gasket is made of a one part that includes at least one flexible feature. For example, the gasket may be made of a multi-part system that includes at least one flexible feature or spring.

The vent gasket (2054) can be positioned and held in place by two nuts: an internal nut (2052) and an external nut (2056). In this embodiment, the vent gasket (2054) can be assembled and tested prior to insertion into the vent channel.

In other embodiments, the vent gasket (2054) is positioned and held in place by at least one external nut (2056) and supported by a shoulder in the vent channel (not shown). The shoulder in the vent channel providing similar support as does the internal nut. In other embodiments, the vent gasket (2054) is positioned and held in place by at least one nut and a partial support in the vent channel (not shown). In other embodiments, the gasket may be positioned and held in place by a support in the vent channel such as a grove.

The vent (450) can be used as a conduit to insert a tool to lock the shaft in position by inserting the tool through the vent (450) in the spindle body (120) and the vent gasket (2054). The inserted tool connects to a corresponding feature on the shaft such that the shaft can be locked in place while torque is applied to the bottom of the shaft. In the exemplified embodiment, the feature on the shaft is a bore (not shown) whose diameter is larger than the diameter of the tool end. In the exemplified embodiment the shaft lock hole in the shaft traverses the shaft on a radial axis. In an embodiment, the feature on the shaft is a flat. In an embodiment, the feature on the shaft is a slot. In an embodiment, the vent gasket (2054) is flexible enough to return to its original shape.

Alternative 2-Part Spindle Body

Figure 21:
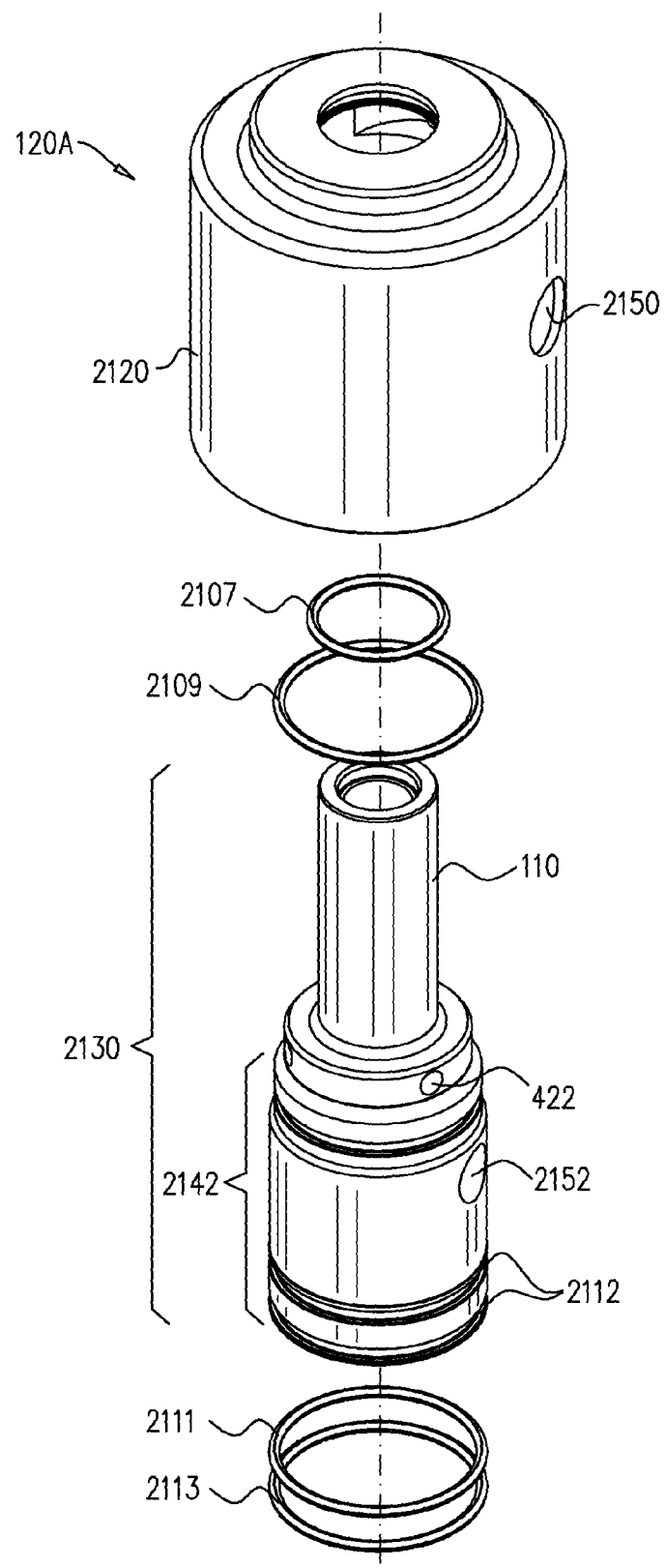
FIG. 21 shows a partial exploded perspective view of a spindle having a two-part body according to embodiments of the present disclosure.

Referring to FIG. 21, another embodiment of spindle body (120A) is shown in an exploded view, where the spindle body (120A) includes a shell (2120) and a core (2130). There are many advantages to dividing the high speed spindle body into multiple parts, such as reduction of material costs, design flexibility in production of multiple versions of similar products for different applications, and embedding of electronics for monitoring and/or communications in the shell. In an embodiment, the two part high speed spindle body (120A) is lighter than a comparable one part high speed spindle body.

In an embodiment, the shell (2120) and core (2130) are made from different materials. In an embodiment the core is made from hardened materials such as stainless steel or steel. The core materials must provide sufficient hardness in the bearing mounting areas and high stiffness for spindle accuracy. In an embodiment, the shell is made from lighter materials such as aluminum, composite materials, or plastic. The shell material has to have sufficient strength to support the high pressure fluid channels that are incorporated there.

In the exemplified embodiment, the two part high speed spindle body (120A) is interchangeable with a one part high speed spindle body (120, FIG. 4) such that minimal modifications, if any, need to be made to other system parts. In some embodiments, the shell can be modified to add functionality such as sensors and housings for monitoring and control components.

FIG. 21 shows a shell (2120), a core (2130), a first O-ring (2107), and a second O-ring (2109) that are positioned between the shell (2120) and the shank (110) portion of the core (2130). A third O-ring (2111) and a fourth O-ring (2113) are positioned around the core (2130) in second O-ring slots (2112).

The core (2130) includes a shank (110), a wider diameter portion that is the bearing cavity housing (2142), an opening of the primarily horizontal fluid channel (422) and a core vent opening (2152). The shell (2120) includes a shell vent opening (2150).

Figure 22A:
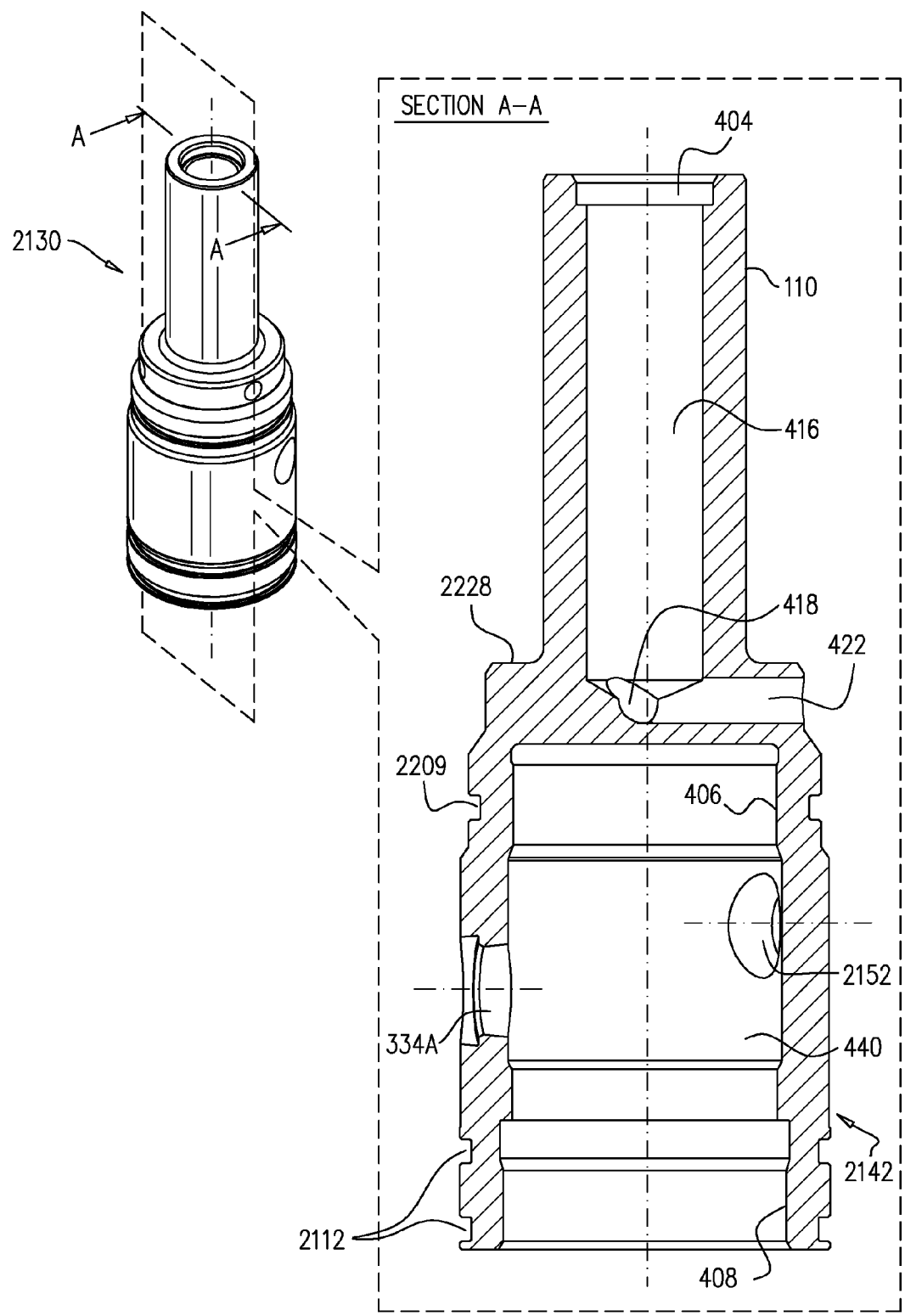
FIG. 22A shows a cross sectional view of the core portion of the body shown in FIG. 21.

Referring to FIG. 22A, section A-A is a cross section of the core (2130). FIG. 22A shows a portion of the fluid channel system within the two part high speed spindle body (120A). The fluid channel system consists of the shank channel (416) within the shank (110) that fluidly connects the fluid entrance (102) with the fluid channel junction (418). The fluid channel junction (418) fluidly connects with at least one primarily horizontal fluid channel (422).

The core (2130) also includes: a high speed spindle cavity housing (2142), the high speed spindle cavity (440), a core vent opening (2152), core surface (2228) which benches against the shell when the two parts are assembled, a first O-ring slot (2209) and second O-ring slots (2112) at the distal end of the core (2130), first bearing cavity-mounting surface (406), second bearing cavity-mounting surface (408) and a sensing aperture (334A) in the core. The sensing aperture (334A) in the core (2130) is substantially similar to the sensing aperture (334) in the entire body (120) as discussed above.

Figure 22B:
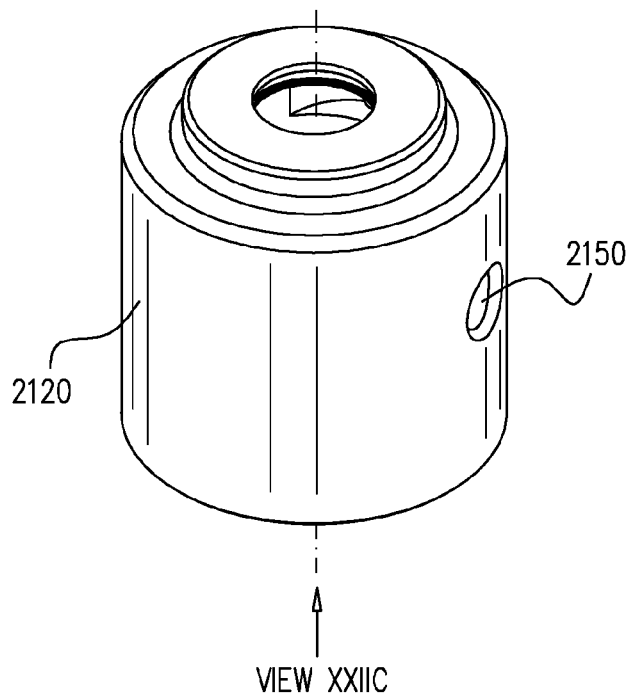
FIGS. 22B, 22C and 22D show perspective, bottom and cross sectional views respectively of the shell portion of the body shown in FIG. 21.

Referring to FIG. 22B, the shell (2120) includes a shell vent opening (2150). Although not shown, the shell (2120) can include a sensing aperture in communication the sensing aperture (334A) within the core (2130) in order to provide sensing access from the exterior through to the shaft (530).

Figure 22C:
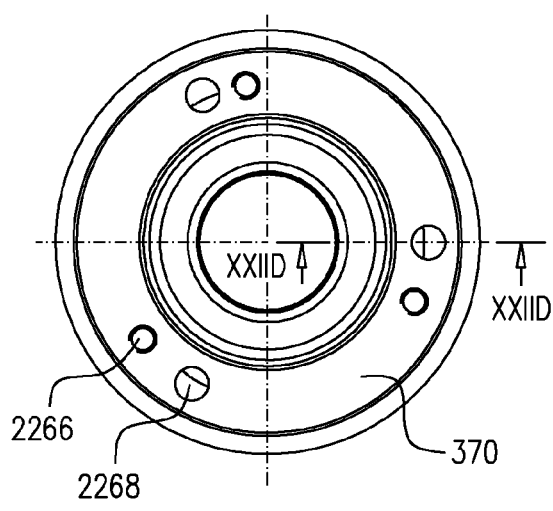

Referring to FIG. 22C, the shell bottom view includes vertical fluid channel openings (2268) the fluidly communicates with the first fluid manifold (370), and shell threaded holes (2266) that are used to connect a seal housing (not shown).

Figure 22D:
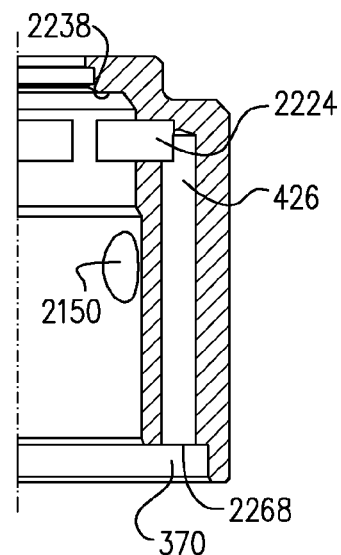

Referring to FIG. 22D, section XXIID is a cross section of the shell (2120). FIG. 22D shows a portion of the fluid channel system within the two part high speed spindle body (120A), including: at least one secondary horizontal fluid channel (2224) that fluidly connects to at least one primarily horizontal fluid channel (422) within the core, and to the primary vertical fluid channel (426) within the shell, that is further fluidly connected to the first fluid manifold (370).

FIG. 22D also includes: a shell vent opening (2150), shell surface (2238) which benches against core surface (2228) when the two parts are assembled.

Bearings

Many factors governing the selection of the optimal bearings for use with the spindles of this disclosure. These factors include the available space, the loads the bearing will encounter, the speeds (including acceleration and deceleration requirements), the required stiffness and precision, noise level, cost considerations and more.

The high speed rotation spindle may incorporate at least one contact bearing. Examples of suitable contact bearings may include radial contact bearings, an angular contact ball bearing, a deep groove ball bearing, a cylindrical roller bearing, a needle roller bearing, a spherical roller bearing, and a tapered roller bearing.

All of the above bearing types may be open, shielded or sealed designs.

Preferably, at least one bearing is a shielded type bearing. The shielding rings insulate the bearing race and rolling elements from their environment. However, the insulation of the shield is not 100% hermetic, that is, it does not completely prevent seepage of fluid, moisture, humidity etc., to spaces in proximity to the bearing rolling elements and the races, but it does reduce the amount that seeps through. Furthermore, it is very effective in blocking solid particles from entering spaces in proximity to the bearing rolling elements and the races.

In some embodiments, the shielded bearing includes two shields, one on each side of the rolling elements. The shields can be mounted in the grooves of the inner and outer bearing races or the shields can be mounted on the exterior portion of the races.

In some embodiments, one shield is mounted in either or both grooves of the inner and outer bearing races while one shield is mounted on the exterior portion of the races, in the direction from which insulation from the environment is most needed.

Preferably, at least two bearings are mounted on the shaft. In some embodiments the at least two bearings have the same radial dimensions. In some embodiments, the at least two bearings have the same height dimensions.

Alternatively, the at least two bearings may have different radial and/or height dimensions. In an embodiment, the bearing closer to the cutting tool end is designed to carrying a higher portion of the load during shaft rotation. In an embodiment, the bearing closer to the cutting tool end is the largest bearing mounted on the rotating shaft. In an embodiment, a second bearing is mounted further away from the cutting tool end than a first bearing. In an embodiment, the second bearing is designed to have axial expansion capabilities.

In an embodiment, the at least two bearing having different dimensions to reduce vibration in elements in which they are in contact. In an embodiment, the at least two bearing having different dimensions to reduce vibration in elements of the high speed spindle. In an embodiment, at least two bearing have different dimensions to reduce high frequency vibration in elements in which they are in contact with. In an embodiment, the at least two bearing having different dimensions reduce high frequency vibration in elements of the high speed spindle.

In an embodiment, the at least one bearing dimensions are (12, 28, 8). In an embodiment the at least second bearing dimensions are (10, 26, 8). Wherein bearing dimensions are provided in mm using the following convention: (inner diameter, outer diameter, bearing thickness or width).

In an embodiment, the at least one bearing dimensions are (15, 28, 7) or (17, 30, 7). In an embodiment the at least second bearing dimensions are (10, 22, 6) or (10, 24, 6) or (12, 24, 6) or (10, 30, 9).

In an embodiment, the at least one bearing inner diameter dimensions are smaller than 10, 11, 12, 13, 14, 15, or 16 mm. In an embodiment, the at least one bearing outer diameter dimensions are smaller than 19, 20, 21, 22, 22, 23, 24, 25, 26, 27, 28, 29, or 30 mm.

In an embodiment, more at least three bearings are mounted on the shaft. In an embodiment, at least four bearings are mounted on the shaft.

In an embodiment the fluid driven high speed spindle is cooled by the high pressure fluid flowing in the fluid channel system. In an embodiment the fluid channels are in sufficient proximity to the bearings to remove heat generated by the bearing during high speed rotation.

Alternative Internal Subsystem

Figure 23:
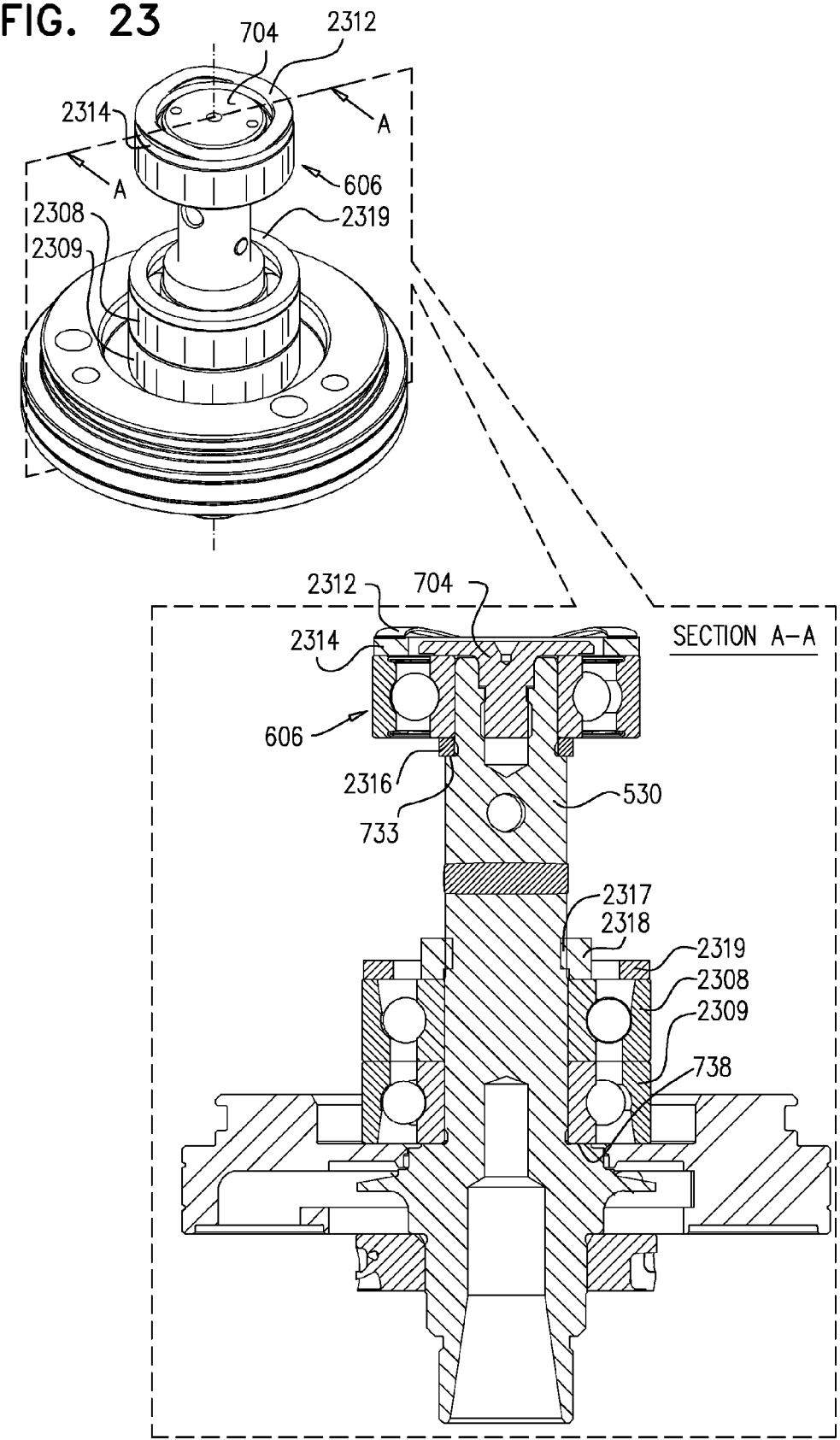
FIG. 23 provides a top perspective view and associated cross sectional view of an internal subsystem of the spindle of FIGS. 1A and 1B according to another embodiment.

Turning to FIG. 23, an alternative to the internal subsystem (240 of FIG. 2) is shown.

In the exemplified embodiment, first bearing (606) is a deep grove ball bearing, whose inner ring is mounted on a first washer (2316) which is further benched against a shoulder or similar feature in the shaft, first bearing mounting shoulder (733). On its other end, the first bearing (606) is secured by shaft top screw (704) that is in contact with the first bearing inner ring. Second washer (2314) is positioned on first bearing outer ring and spring (2312) is positioned above second washer (2314). When the system is assembled, spring (2312) is situated between the first bearing and the bearing cavity inner surface (not shown). When assembled, the spring (2312) applies a force on the first bearing outer ring (716) through second washer (2314). In an embodiment, the spring (2312) is positioned above first bearing outer ring (716)

In the illustrated embodiment, second bearing (508) includes a pair of angular bearings (2308, 2309). In an embodiment, the pair of angular bearings (2308, 2309) are assembled in a back to back configuration. In an embodiment, the pair of angular bearings (2308, 2309) are assembled in a front to front configuration. In an embodiment, the pair of angular bearings (2308, 2309) are assembled in a front to back configuration. The angular bearings (2308, 2309) function as a unit. When assembled, first angular bearing (2309) has an inner ring benched against a shoulder or similar feature in the shaft, such as second bearing mounting shoulder (738). On its other end, the second angular bearing (2308) has an inner ring secured by bearing nut (2318) that is located on shaft thread (2317). A third washer (2319) is positioned on the outer ring of the second angular bearing (2308). When assembled, third washer (2319) is benched against a shoulder or similar feature (not shown) in the bearing cavity inner surface.

In the exemplified embodiment high axial stiffness and system accuracy can be realized without a bearing spacer.

Bearing Lubrication

The choice of lubricant is important. Contact bearings are lubricated with numerous types of greases and oils. The choice of a lubricant depends primarily on the operating conditions, i.e. the temperature range and speeds as well as the influence of the surroundings. In fluid driven high speed spindle, the lubricant must support high speed rotation while being in insensitive to small amounts of fluid.

In an embodiment the bearing rolling elements and races are protected from fluid, vapors, moisture and solid particles by lubrication material. In an embodiment the lubrication material is grease.

In an embodiment the grease shall be a compound from synthetic oil and metal soap thickener and or additives. An example of possible synthetic oil also known base oil is PAO (poly-alpha-olefin).

Metal soap thickeners include lithium soap and lithium complex soap. Additives include rust inhibitors and or PFPE and or PTFE compounds. Greases containing PFPE and PTFE compounds are typically insoluble in water, acids, bases, and most organic solvents and can withstand extreme pressure and high mechanical stress. For example UniFlor PerFluoroPolyether (PFPE) lubricants, compounds: #8172; #8981; #8917; #8512; #8950 and others from the same and or other manufacturers.

In an embodiment space constraints are defined based on ATC requirements. In an embodiment, the maximum diameter of the high speed spindle is 80 mm.

Shaft

The shaft design includes conflicting considerations such as high stiffness dictating larger diameter and higher speeds requiring less mass and less friction dictating a smaller shaft diameter. The shaft design considerations also availability of space and volume in the system as well as cutting tool diameter.

In an embodiment, the maximum cutting tool diameter is 7 mm. In an embodiment, the maximum cutting tool diameter is 7 mm and the rotational speed is at least 25,000 revolutions per second. In an embodiment, the maximum cutting tool diameter is 6 mm and the rotational speed is at least 35,000 revolutions per second.

In an embodiment, the cutting tool is secured to the shaft by means adhering to requirements defined by the ER 11 standard.

In an embodiment, the shaft diameter varies along its length. In an embodiment, the shaft diameter is larger at the cutting tool end than at the mounting location of at least one bearing. In an embodiment, the shaft diameter is at least 12 mm in proximity to the collet and or at least 17 mm above the cutting tool end. In an embodiment the shaft diameter at the mounting location of at least one bearing is at least 10 mm. In an embodiment, the shaft diameter at the mounting location of at least a second bearing is larger than the shaft diameter at the mounting location of at least one bearing. In an embodiment, the shaft diameter at the mounting location of at least a second bearing is smaller than the shaft diameter at the mounting location of at least one bearing.

Fluid System Considerations

In an embodiment the fluid pressure entering the high speed spindle is more than 10 bar. In an embodiment the fluid pressure entering the high speed spindle is more than 17 bar. In an embodiment the fluid pressure entering the high speed spindle is more than 20 bar. In an embodiment the fluid pressure entering the high speed spindle is more than 25 bar. In an embodiment the fluid pressure entering the high speed spindle is more than 40 bar.

In an embodiment the fluid flow entering the high speed spindle is more than 5 liter per minute. In an embodiment the fluid flow entering the high speed spindle is more than 10 liter per minute. In an embodiment the fluid flow entering the high speed spindle is more than 17 liter per minute. In an embodiment the fluid flow entering the high speed spindle is more than 20 liter per minute In an embodiment the fluid pressure entering the high speed spindle is 17 bar and the flow is 12 Liter per minute. In an embodiment the fluid pressure entering the high speed spindle is 17 bar and the flow is 9 Liter per minute.

In an embodiment the fluid is primarily water based. In an embodiment the fluid is an emulsion used in machining processes. In an embodiment the fluid is primarily oil based.

Example Spindle Operation Characteristics

In an embodiment the axial load applied on the cutting tool tip is less than 25 N. In an embodiment the axial load applied on the cutting tool tip is less than 50 N. In an embodiment the axial load applied on the cutting tool tip is less than 75 N.

In an embodiment the perpendicular load applied on the cutting tool tip is less than 50 N. In an embodiment the perpendicular load applied on the cutting tool tip is less than 100 N. In an embodiment the perpendicular load applied on the cutting tool tip is less than 170 N. In an embodiment the perpendicular load applied on the cutting tool tip is less than 200 N.

In an embodiment the acceleration and deceleration of the high speed spindle rotational velocity is less than 1700 rad/sec$^2$. In an embodiment the acceleration and deceleration of the high speed spindle rotational velocity is less than 1700 rad/sec$^2$. In an embodiment the acceleration and deceleration of the high speed spindle rotational velocity is less than 2000 rad/sec$^2$. In an embodiment the acceleration and deceleration of the high speed spindle rotational velocity is less than 3000 rad/sec$^2$.

In an embodiment the precision of rotation between the shank and the shaft end is less than 2.5 micron. In an embodiment the precision of rotation between the shank and the shaft end is less than 5 micron. In an embodiment the precision of rotation between the shank and the shaft end is less than 10 micron. In an embodiment the precision of rotation between the shank and the shaft end is less than 17 micron.

PARTS LIST

| Number | Part Names |
| --- | --- |
| A | Longitudinal axis |
| 100 | Spindle |
| 101 | Shank extension |
| 102 | Entry port |
| 110 | Shank |
| 120, 120A | Body |
| 130 | Sensor module |
| 150, 150A, 150B | Seal housing |
| 180, 180A, 180B | Cover |
| 204 | Filtration unit nut |
| 206 | Mesh |
| 214 | Wrench grip |
| 218 | Seal slot |
| 232 | Mounting location |
| 240 | Internal subsystem |
| 248 | Gasket |
| 252 | First screws |
| 282 | Second screws |
| 290 | Collet |
| 292 | Collet nut |
| 312 | Cone shank |
| 324 | Access opening |
| 334 | Sensing aperture |
| 335 | Fluid aperture |
| 336 | Mounting threads |
| 338 | Mounting slots |
| 352 | Threaded holes |
| 354 | Bottom openings |
| 370 | First fluid manifold |
| 398 | Bottom end |
| 404 | Shank end |
| 406 | First bearing cavity mounting surface |
| 408 | Second bearing cavity mounting surface |
| 412 | Shank thread |
| 416 | Shank channel |
| 418 | Fluid channel junction |
| 422 | Primary horizontal fluid channel |
| 426 | Primary vertical fluid channel |
| 440 | Cavity |
| 442 | Spacer shoulder |
| 444 | Smaller-diameter section |
| 446 | Larger-diameter section |
| 450 | Vent |
| 496 | Exterior |
| 506 | Gap |
| 508 | Second bearing |
| 512 | Major turbulence pocket |
| 527 | Secondary vertical fluid channel |
| 528 | Inlet channel |
| 530 | Shaft |
| 552 | Second annular fluid manifold |
| 556 | Stationary fluid exit channel |
| 570, 570A | Turbine |
| 571 | Central fluid exit |
| 572A | Lower annular gap |
| 572B | Upper annular gap |
| 572 | Annular gap |
| 573 | Second fluid exit |
| 574 | Seal annular gap |
| 576 | Nozzle |
| 578 | Nozzle fluid manifold |
| 583 | Exit channel |
| 586 | Second axial exit opening |
| 587 | Bottom annular cavity |
| 588, 588A | First axial exit opening |
| 598 | Shaft tool end |
| 606 | First bearing |
| 610 | Bearing spacer |
| 612 | Bearing spacer opening |
| 622 | External shoulder |
| 623 | Internal shoulder |
| 651 | Bottom surface |
| 656 | Counter bores |
| 660, 660A | Flinger |
| 686 | Seal housing fluid exit holes |
| 704 | Shaft top screw |
| 711 | Positioning shoulder |
| 714 | Rotational position reference |
| 716 | First-bearing outer ring |
| 717 | First-bearing inner ring |
| 718 | Second-bearing outer ring |
| 719 | Second-bearing inner ring |
| 732 | First bearing shaft mounting surface |
| 733 | First bearing shaft mounting shoulder |
| 734 | Shaft lock hole |
| 736 | Second bearing mounting surface |
| 738 | Second bearing mounting shoulder |
| 774 | Turbine ring |
| 794 | Collet mounting surface |
| 795 | Thread |
| 900, 900A | Non-contact seal |
| 914 | Minor turbulence pocket |
| 916 | Step-like feature |
| 918 | Opposing shaft section |
| 922 | Vertical gap |
| 923 | Flat upper surface |
| 924 | Recess |
| 925 | Slot wall |
| 926 | Large opening |
| 932 | Shaft first section |

-continued

| Number | Part Names |
|---|---|
| 934 | Slot shoulder |
| 936 | Annular horizontal gap |
| 938 | Rotating ledge |
| 954 | Seal housing inner surface |
| 961 | Second flinger |
| 962 | Flinger lower surface |
| 963 | Second-flinger lower surface |
| 964 | Flinger edge surface |
| 966 | Flinger upper surface |
| 969 | Turbine area |
| 977 | Nozzle ring |
| 979 | Cover inner surface |
| 981 | Radial perimeter |
| 982 | Axial fluid exit channel first section |
| 984 | Axial fluid exit channel second section |
| 1024 | Stationary surface |
| 1040 | Spring flinger |
| 1042 | Spring flinger upper surface |
| 1043 | Spring flinger mounting surface |
| 1044 | Thinner section |
| 1045 | Spring flinger cross-section |
| 1140, 1140A | Flexible flap |
| 1142 | Flexible flap lower surface |
| 1143, 1143A | Flexible flap mounting surface |
| 1144, 1144A | Flexible portion |
| 1145, 1145A | Flexible flap cross section |
| 1229 | Auxiliary fluid channel |
| 1247 | Flexible flap cavity |
| 1340 | Stationary ring |
| 1355 | First surface |
| 1358 | Second surface |
| 1363 | Root |
| 1374 | Narrow seal annular channel |
| 1455 | Lateral fluid exit channel |
| 1457 | Sidewall fluid exit opening |
| 1538 | Seal housing ledge |
| 1542 | Ring opening |
| 1546 | Rotatable ring |
| 1810 | External surface |
| 1812 | Interface surface |
| 1814 | Screw holes |
| 1822 | Nozzle ring external surface |
| 1824 | Nozzle ring internal surface |
| 1826 | Nozzle inlet |
| 1836 | Nozzle coverings |
| 1838 | Nozzle fluid exit |
| 1873 | First horizontal section |
| 1874 | Second horizontal section |
| 1876 | Vertical section |
| 1885 | Ribs |
| 1887 | Rib-gaps |
| 1939 | Nozzle channel |
| 1940 | Funnel |
| 1942 | First slope |
| 1944 | Apex |
| 1946 | Second slope |
| 2052 | Internal nut |
| 2054 | Vent gasket |
| 2056 | External nut |
| 2107 | First O-ring |
| 2109 | Second O-ring |
| 2111 | Third O-ring |
| 2112 | Second O-ring slots |
| 2113 | Fourth O-ring |
| 2120 | Shell |
| 2130 | Core |
| 2142 | Cavity housing |
| 2150 | Shell vent opening |
| 2152 | Core vent opening |
| 2209 | First O-ring slot |
| 2224 | Secondary horizontal fluid channel |
| 2228 | Core surface |
| 2238 | Shell surface |
| 2266 | Shell threaded holes |
| 2268 | Vertical fluid channel openings |
| 2308 | Second angular bearings |
| 2309 | First angular bearings |
| 2312 | Spring |
| 2314 | Second washer |
| 2316 | First washer |
| 2317 | Shaft thread |
| 2318 | Bearing nut |
| 2319 | Third washer |

What is claimed is:

1. A liquid powered spindle (100) having a longitudinal axis (A) defining an upper, shank end (404) and a lower, shaft-tool end (598), comprising:
   a) a body (120) having a spindle cavity (440);
   b) at least one bearing (508) disposed in the cavity (440);
   c) a shaft (530) supported by the at least one bearing (508) within the cavity (440);
   d) a seal housing (150) connected to the body (120) at the lower end thereof;
   e) a cover (180) connected to the seal housing (150) at the lower end thereof;
   f) a fluid channel system for directing liquid from an entry port (102) to a nozzle (576);
   g) a turbine (570) attached to the shaft (530), the turbine in fluid communication with the at least one nozzle for rotating the shaft; and
   h) a flinger (660) attached to the shaft (530) and positioned above the turbine (570) such that the turbine (570) is between the flinger (660) and the lower, shaft-tool end (598);
   wherein the seal housing (150) defines an annular fluid manifold (552) surrounding the shaft (530) for distributing liquid, deflected upward by the turbine (570), into a plurality of stationary fluid exit channels (556);
   wherein the flinger (660) and the seal housing (150) combine to form a non-contact seal (900) configured to impede the flow of liquid toward the at least one bearing (508).

2. The spindle of claim 1, wherein the seal housing (150) further defines:
   a major turbulence pocket (512) is defined by a recess (924) within the seal housing, and positioned adjacent to the shaft (530), the major turbulence pocket being disposed above the annular fluid manifold (552) and the flinger (660).

3. The spindle of claim 2, wherein the recess (924) has a shoulder (934) extending from the radial inner portion thereof such that the recess is capable of retaining liquid when the spindle is inverted.

4. The spindle of claim 2, wherein the major turbulence pocket (512) includes a large opening (926) facing the annular fluid manifold (552) and a small opening (936) defined by a gap between the seal housing (150) and the flinger (660), wherein turbulence within the liquid, impedes flow of the liquid into the small opening (936).

5. The spindle of claim 4, wherein:
   the seal housing (150) further defines a minor turbulence pocket (914) radially inward of the major turbulence pocket (512) and in communication with the small opening (936), the minor turbulence pocket (914) defined by a step-like feature (916) adjacent to the inner diameter of the seal housing (150), and
   the minor turbulence pocket (914) further impedes flow of the liquid through a vertical gap (922) between the seal housing (150) and the shaft (530).

6. The spindle of claim 1, wherein the body (120) further comprises a vent (450) between the spindle cavity (440) and the exterior of the body, wherein the vent is sealed with a vent gasket (2054) capable of allowing flow in both directions.

7. The spindle of claim 1, wherein the at least one bearing (508) is lubricated with grease or oil, different from the fluid.

8. The spindle of claim 1, further comprising a sensor module (130) in communication with at least one aperture (334, 335) formed in the body (120), wherein the at least one aperture allows the sensor module to sense at least one internal characteristic of the spindle.

9. The spindle of claim 1, wherein the at least one bearing (508) is a shielded bearing.

10. The spindle of claim 1, wherein the fluid channel system comprises:
   i) the entry port (102) associated with a shank (110);
   ii) a shank channel (416);
   iii) at least one primarily horizontal fluid channel (422) extending from the end of the shank channel;
   iv) at least one primary vertical fluid channel (426) extending from the at least one primary horizontal fluid channel through the body; and
   v) the at least one nozzle (576) in fluid communication with the at least one primary vertical fluid channel.

11. The spindle of claim 1, wherein the spindle comprises a wrench grip (214) positioned between the body (120) and a shank (110) to accept a wrench and assist with mounting the spindle to a chuck.

12. The spindle of claim 1, wherein the at least one bearing (508) includes at least a pair of angular bearings (2308, 2309) contacting one another.

13. The spindle of claim 1, wherein the cover (180) comprises at least one first axial exit opening (588) at the bottom thereof, the at least one first axial exit opening (588) provides an exit for the liquid directed downward by the turbine (570).

14. The spindle of claim 13, wherein the cover (180) comprises at least one second axial exit opening (586) disposed radially outward with respect to the at least one first axial exit opening (588), the at least one second axial exit opening in fluid communication with the annular fluid manifold (552) in order to discharge the liquid deflected upward by the turbine (570).

15. The spindle of claim 14, wherein the cover (180) comprises at least one axial fluid exit channel (982, 984) communicating with the at least one second axial exit opening (586), the axis of the axial fluid exit channel being angled with respect to the shaft (530) such that liquid exiting the at least one second axial exit opening (586) will be directed toward the longitudinal axis (A).

16. The spindle of claim 1, wherein the at least one bearing is a plurality of bearings, and the plurality of bearings are of different types or dimensions.

17. The spindle of claim 1, further comprising a stationary ring (1340) disposed within the seal housing (150), the stationary ring (1340) configured to impinge upon a seal annular gap (574) positioned below the flinger (660).

18. The spindle of the claim 1, wherein:
   the at least one nozzle (576) is formed along the inner diameter of a nozzle ring (977), the nozzle ring (977) is disposed within the cover (180) to define a nozzle fluid manifold (578),
   the at least one nozzle (576) is angled relative to the radial direction of the shaft (530) in order to impact with maximum force of the fluid on the turbine (570).

19. The spindle of claim 1, wherein the body (102) comprises:
   a) a shell (2120); and
   b) a core (2130), the core comprising:
      i) a bearing housing cavity (2142) surrounding the spindle cavity (440); and
      ii) a shank (110); and
   wherein the fluid channel system further comprises:
      i) the entry port (102) associated with the shank (110);
      ii) a shank channel (216);
      iii) at least one primary horizontal fluid channel (422) extending from the end of the shank channel through the bearing housing cavity (2142);
      iv) at least one primary vertical fluid channel (426) in the shell, the at least one primary vertical fluid channel (426) in fluid communication with the at least one horizontal fluid channel through bearing housing cavity; and
      v) the at least one nozzle (576) in fluid communication with the at least one primary vertical fluid channel.

20. The spindle of claim 19, wherein:
   the shell (2120) has a first material having a first density and a first hardness and the core (2130) has a second material having a second density and second hardness, and
   the first density is less than the second density and the first hardness is less than the second hardness.

21. The spindle of claim 1, wherein:
   the flinger (660) is a spring flinger (1040), the spring flinger (1040) having a flexible section (1044), the spring flinger attached to the shaft (530) and positioned above the turbine (570); and wherein:
   when the shaft (530) is idle the flexible section (1044) has a first position relatively close to the shaft such that the flexible section contacts and seals with a portion of the seal housing (150), and
   when the shaft is rotating, the centrifugal forces generated by the rotating shaft cause the flexible section (1044) to flex away from the shaft, providing a flinger surface for deflecting the liquid, and removing contact with the seal housing (150).

* * * * *